US007780991B2

(12) United States Patent
Roser et al.

(10) Patent No.: US 7,780,991 B2
(45) Date of Patent: *Aug. 24, 2010

(54) SOLID DOSE DELIVERY VEHICLE AND METHODS OF MAKING SAME

(75) Inventors: Bruce J. Roser, Cambridge (GB); Jaap Kampinga, Groningen (NL); Camilo Colaco, Cambridge (GB); Julian Blair, Cambridgeshire (GB)

(73) Assignee: Quadrant Drug Delivery Limited (GB)

(*) Notice: Subject to any disclaimer, the term of this patent is extended or adjusted under 35 U.S.C. 154(b) by 0 days.

This patent is subject to a terminal disclaimer.

(21) Appl. No.: 11/134,701

(22) Filed: May 20, 2005

(65) Prior Publication Data

US 2005/0276759 A1 Dec. 15, 2005

Related U.S. Application Data

(63) Continuation of application No. 10/652,212, filed on Aug. 29, 2003, now Pat. No. 7,056,495, which is a continuation of application No. 10/376,136, filed on Feb. 27, 2003, now Pat. No. 6,893,657, which is a continuation of application No. 09/945,180, filed on Aug. 31, 2001, now Pat. No. 6,565,871, which is a continuation of application No. 09/628,380, filed on Aug. 1, 2000, now Pat. No. 6,331,310, which is a continuation of application No. 08/349,029, filed on Dec. 2, 1994, now Pat. No. 6,290,991.

(51) Int. Cl.
*A61K 9/50* (2006.01)

(52) U.S. Cl. ....................................... 424/499; 424/489

(58) Field of Classification Search ................. 424/489, 424/499

See application file for complete search history.

(56) References Cited

U.S. PATENT DOCUMENTS

| | | | |
|---|---|---|---|
| 125,714 | A | 4/1872 | Allen |
| 586,504 | A | 7/1897 | Marsch |
| 979,993 | A | 12/1910 | O'Byrne et al. |
| 1,855,591 | A | 4/1932 | Wallerstein |
| 2,457,036 | A | 12/1948 | Epstein |

(Continued)

FOREIGN PATENT DOCUMENTS

| | | |
|---|---|---|
| BE | 902 257 | 8/1985 |

(Continued)

OTHER PUBLICATIONS

Costantino, H. R. et al., (1994). "Moisture-Induced Aggregation of Lyophilized Insulin," *Pharmaceutical Research* 11(1):21-29.

(Continued)

*Primary Examiner*—Carlos A. Azpuru
(74) *Attorney, Agent, or Firm*—Morrison & Foerster LLP

(57) ABSTRACT

The present invention encompasses a solid dose delivery vehicle for ballistic administration of a bioactive material to subcutaneous and intradermal tissue, the delivery vehicle being sized and shaped for penetrating the epidermis. The delivery vehicle further comprises a stabilizing polyol glass loaded with the bioactive material and capable of releasing the bioactive material in situ. The present invention further includes methods of making and using the solid dose delivery vehicle of the invention.

39 Claims, 10 Drawing Sheets

U.S. PATENT DOCUMENTS

| | | |
|---|---|---|
| 2,549,303 A | 4/1951 | Friden |
| 2,648,609 A | 8/1953 | Wurster |
| 3,362,405 A | 1/1968 | Hazel |
| 3,456,050 A | 7/1969 | Rieckmannn et al. |
| 3,480,468 A | 11/1969 | Carletti et al. |
| 3,540,984 A | 11/1970 | Deutsch |
| 3,554,767 A | 1/1971 | Daum et al. |
| 3,557,717 A | 1/1971 | Chivers |
| 3,583,491 A | 6/1971 | Lindeberg |
| 3,608,066 A | 9/1971 | Illartein |
| 3,619,294 A | 11/1971 | Black et al. |
| 3,632,357 A | 1/1972 | Childs |
| 3,655,442 A | 4/1972 | Schwer et al. |
| 3,666,496 A | 5/1972 | Honey et al. |
| 3,674,901 A | 7/1972 | Shepherd et al. |
| 3,694,547 A | 9/1972 | Forsthoff |
| 3,745,682 A | 7/1973 | Waldeisen |
| 3,921,637 A | 11/1975 | Bennie et al. |
| 3,937,668 A | 2/1976 | Zolle |
| 3,948,263 A | 4/1976 | Drake, Jr. et al. |
| 3,964,483 A | 6/1976 | Mathes |
| 3,991,761 A | 11/1976 | Cocozza |
| 4,018,185 A | 4/1977 | Myers |
| 4,036,223 A | 7/1977 | Obert |
| 4,069,819 A | 1/1978 | Valentini et al. |
| 4,098,273 A | 7/1978 | Glenn |
| 4,102,999 A | 7/1978 | Umezawa et al. |
| 4,105,027 A | 8/1978 | Lundquist |
| 4,114,615 A | 9/1978 | Wetterlin |
| 4,127,502 A | 11/1978 | Li Mutti et al. |
| 4,127,622 A | 11/1978 | Watanabe et al. |
| 4,153,689 A | 5/1979 | Hirai et al. |
| 4,157,386 A | 6/1979 | La Rochelle |
| 4,158,544 A | 6/1979 | Louderback |
| 4,159,319 A | 6/1979 | Bachmann et al. |
| 4,180,593 A | 12/1979 | Cohan |
| 4,192,309 A | 3/1980 | Poulsen |
| 4,211,769 A | 7/1980 | Okada et al. |
| 4,227,522 A | 10/1980 | Carris |
| 4,244,949 A | 1/1981 | Gupta |
| 4,249,526 A | 2/1981 | Dean et al. |
| 4,253,468 A | 3/1981 | Lehmbeck |
| 4,294,829 A | 10/1981 | Suzuki et al. |
| 4,305,925 A | 12/1981 | Kapmeyer |
| 4,326,524 A | 4/1982 | Drake, Jr. et al. |
| 4,327,076 A | 4/1982 | Puglia et al. |
| 4,327,077 A | 4/1982 | Puglia et al. |
| 4,338,931 A | 7/1982 | Cavazza |
| 4,371,557 A | 2/1983 | Oppy et al. |
| 4,372,942 A | 2/1983 | Cimiluca |
| 4,407,786 A | 10/1983 | Drake et al. |
| 4,423,086 A | 12/1983 | Devos et al. |
| 4,446,862 A | 5/1984 | Baum et al. |
| 4,452,239 A | 6/1984 | Malem |
| 4,462,982 A | 7/1984 | Samejima et al. |
| 4,484,577 A | 11/1984 | Sackner et al. |
| 4,503,035 A | 3/1985 | Pestka et al. |
| 4,534,343 A | 8/1985 | Nowacki et al. |
| 4,551,329 A | 11/1985 | Harris et al. |
| 4,588,744 A | 5/1986 | McHugh |
| 4,590,206 A | 5/1986 | Forrester et al. |
| 4,591,552 A | 5/1986 | Neurath |
| 4,599,311 A | 7/1986 | Kawasaki |
| 4,613,500 A | 9/1986 | Suzuki et al. |
| 4,617,272 A | 10/1986 | Kirkwood et al. |
| 4,620,847 A | 11/1986 | Shishov et al. |
| 4,624,251 A | 11/1986 | Miller |
| 4,627,432 A | 12/1986 | Newell et al. |
| 4,656,250 A | 4/1987 | Morita et al. |
| 4,659,696 A | 4/1987 | Hirai et al. |
| 4,677,975 A | 7/1987 | Edgar et al. |
| 4,680,027 A | 7/1987 | Parsons et al. |
| 4,684,719 A | 8/1987 | Nishikawa et al. |
| 4,698,328 A | 10/1987 | Neer et al. |
| 4,698,917 A | 10/1987 | Debolini |
| 4,701,417 A | 10/1987 | Portenhauser et al. |
| 4,713,249 A | 12/1987 | Schröder |
| 4,721,709 A | 1/1988 | Seth et al. |
| 4,739,754 A | 4/1988 | Shaner |
| 4,741,872 A | 5/1988 | De Luca et al. |
| 4,743,554 A | 5/1988 | Boothroyd et al. |
| 4,749,575 A | 6/1988 | Rotman |
| 4,753,790 A | 6/1988 | Silva et al. |
| 4,758,583 A | 7/1988 | Cerami et al. |
| 4,761,400 A | 8/1988 | Doat et al. |
| 4,762,719 A | 8/1988 | Forester |
| 4,762,857 A | 8/1988 | Bollin, Jr. et al. |
| 4,778,054 A | 10/1988 | Newell et al. |
| 4,790,305 A | 12/1988 | Zoltan et al. |
| 4,790,824 A | 12/1988 | Morrow et al. |
| 4,793,997 A | 12/1988 | Drake et al. |
| 4,811,731 A | 3/1989 | Newell et al. |
| 4,812,444 A | 3/1989 | Mitsuhashi et al. |
| 4,814,436 A | 3/1989 | Shibata et al. |
| 4,818,542 A | 4/1989 | DeLuca et al. |
| 4,819,629 A | 4/1989 | Jonson |
| 4,824,938 A | 4/1989 | Koyama et al. |
| 4,830,858 A | 5/1989 | Payne et al. |
| 4,833,125 A | 5/1989 | Neer et al. |
| 4,847,079 A | 7/1989 | Kwan |
| 4,847,090 A | 7/1989 | Della Posta et al. |
| 4,849,225 A | 7/1989 | Mitsuhashi et al. |
| 4,855,326 A | 8/1989 | Fuisz |
| 4,861,627 A | 8/1989 | Mathiowitz et al. |
| 4,863,865 A | 9/1989 | Franks |
| 4,865,871 A | 9/1989 | Livesey et al. |
| 4,866,051 A | 9/1989 | Hunt |
| 4,873,085 A | 10/1989 | Fuisz |
| 4,883,762 A | 11/1989 | Hoskins |
| 4,884,565 A | 12/1989 | Cocozza |
| 4,888,398 A | 12/1989 | Bichon et al. |
| 4,889,114 A | 12/1989 | Kladders |
| 4,891,319 A | 1/1990 | Roser |
| 4,895,719 A | 1/1990 | Radhakrishnan et al. |
| 4,898,781 A | 2/1990 | Onouchi et al. |
| 4,906,463 A | 3/1990 | Cleary et al. |
| 4,907,583 A | 3/1990 | Wetterlin et al. |
| 4,926,852 A | 5/1990 | Zoltan et al. |
| 4,942,544 A | 7/1990 | McIntosh et al. |
| 4,946,828 A | 8/1990 | Markussen |
| 4,952,402 A | 8/1990 | Sparks et al. |
| 4,963,359 A | 10/1990 | Haslwanter et al. |
| 4,984,158 A | 1/1991 | Hillsman |
| 4,985,252 A | 1/1991 | Jung et al. |
| 4,988,683 A | 1/1991 | Corbiere |
| 4,995,385 A | 2/1991 | Valentini et al. |
| 4,997,654 A | 3/1991 | Corsello et al. |
| 5,006,343 A | 4/1991 | Benson et al. |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Roser |
| 5,026,772 A | 6/1991 | Kobayashi et al. |
| 5,027,806 A | 7/1991 | Zoltan et al. |
| 5,033,463 A | 7/1991 | Cocozza |
| 5,035,237 A | 7/1991 | Newell et al. |
| 5,042,975 A | 8/1991 | Chien et al. |
| 5,043,165 A | 8/1991 | Radhakrishnan |
| 5,048,514 A | 9/1991 | Ramella |
| 5,049,388 A | 9/1991 | Knight et al. |
| 5,049,389 A | 9/1991 | Radhakrishnan |
| 5,051,261 A | 9/1991 | McGinity et al. |
| 5,057,392 A | 10/1991 | McCabe et al. |
| 5,059,587 A | 10/1991 | Yamamoto et al. |

| | | | | | |
|---|---|---|---|---|---|
| 5,069,936 A | 12/1991 | Yen | 5,567,433 A | 10/1996 | Collins |
| 5,089,181 A | 2/1992 | Hauser | 5,567,439 A | 10/1996 | Myers et al. |
| 5,093,316 A | 3/1992 | Lezdey et al. | 5,571,499 A | 11/1996 | Hafler et al. |
| 5,098,893 A | 3/1992 | Franks et al. | 5,575,987 A | 11/1996 | Kamei et al. |
| 5,098,955 A | 3/1992 | Pettit | 5,578,567 A | 11/1996 | Cardinaux et al. |
| 5,112,596 A | 5/1992 | Malfroy-Camine | 5,580,856 A | 12/1996 | Prestrelski et al. |
| 5,112,598 A | 5/1992 | Biesalski | 5,580,859 A | 12/1996 | Felgner et al. |
| 5,113,855 A | 5/1992 | Newhouse | 5,589,167 A | 12/1996 | Cleland et al. |
| 5,120,643 A | 6/1992 | Ching et al. | 5,591,453 A | 1/1997 | Ducheyne et al. |
| 5,139,016 A | 8/1992 | Waser | 5,607,915 A | 3/1997 | Patton et al. |
| 5,149,653 A | 9/1992 | Roser | 5,611,344 A | 3/1997 | Bernstein et al. |
| 5,160,745 A | 11/1992 | DeLuca et al. | 5,618,786 A | 4/1997 | Roosdorp et al. |
| 5,173,298 A | 12/1992 | Meadows | 5,621,094 A | 4/1997 | Roser et al. |
| 5,175,179 A | 12/1992 | Larson | 5,626,871 A | 5/1997 | Makino et al. |
| 5,182,097 A | 1/1993 | Byron et al. | 5,631,225 A | 5/1997 | Sorensen |
| 5,186,166 A | 2/1993 | Riggs et al. | 5,642,728 A | 7/1997 | Andersson et al. |
| 5,192,528 A | 3/1993 | Radhakrishnan et al. | 5,654,278 A | 8/1997 | Sorensen |
| 5,200,399 A | 4/1993 | Wettlaufer et al. | 5,656,611 A | 8/1997 | Kabanov et al. |
| 5,202,333 A | 4/1993 | Berger et al. | 5,667,806 A | 9/1997 | Kantor |
| 5,204,108 A | 4/1993 | Illum | 5,672,581 A | 9/1997 | Rubsamen et al. |
| 5,207,217 A | 5/1993 | Cocozza et al. | 5,674,534 A | 10/1997 | Zale et al. |
| 5,215,079 A | 6/1993 | Fine et al. | 5,679,647 A | 10/1997 | Carson et al. |
| 5,225,183 A | 7/1993 | Purewal et al. | 5,681,746 A | 10/1997 | Bodner et al. |
| 5,230,884 A | 7/1993 | Evans et al. | 5,705,482 A | 1/1998 | Sorensen |
| 5,231,031 A | 7/1993 | Szwergold et al. | 5,707,644 A | 1/1998 | Illum et al. |
| 5,239,993 A | 8/1993 | Evans | 5,728,574 A | 3/1998 | Legg |
| 5,240,712 A | 8/1993 | Smith et al. | 5,733,555 A | 3/1998 | Chu |
| 5,240,843 A | 8/1993 | Gibson et al. | 5,766,520 A | 6/1998 | Bronshtein |
| 5,240,846 A | 8/1993 | Collins et al. | 5,775,320 A | 7/1998 | Patton et al. |
| 5,254,330 A | 10/1993 | Ganderton et al. | 5,780,014 A | 7/1998 | Eljamal et al. |
| 5,260,306 A | 11/1993 | Boardman et al. | 5,780,295 A | 7/1998 | Livesey et al. |
| 5,270,048 A | 12/1993 | Drake | 5,785,049 A | 7/1998 | Smith et al. |
| 5,284,656 A | 2/1994 | Platz et al. | 5,811,406 A | 9/1998 | Szoka, Jr. et al. |
| 5,287,850 A | 2/1994 | Haber et al. | 5,814,607 A | 9/1998 | Patton |
| 5,290,765 A | 3/1994 | Wettlaufer et al. | 5,849,700 A | 12/1998 | Sorensen et al. |
| 5,302,581 A | 4/1994 | Sarin et al. | 5,851,453 A | 12/1998 | Hanna et al. |
| 5,306,506 A | 4/1994 | Zema et al. | 5,855,913 A | 1/1999 | Hanes et al. |
| 5,309,900 A | 5/1994 | Knoch et al. | 5,881,719 A | 3/1999 | Gottenauer et al. |
| 5,312,335 A | 5/1994 | McKinnon et al. | 5,891,873 A | 4/1999 | Colaco et al. |
| 5,312,909 A | 5/1994 | Driessen et al. | 5,928,469 A | 7/1999 | Franks et al. |
| 5,320,094 A | 6/1994 | Laube et al. | 5,948,411 A | 9/1999 | Koyama et al. |
| 5,326,586 A | 7/1994 | Grabowski et al. | 5,952,008 A | 9/1999 | Backstrom et al. |
| 5,334,617 A | 8/1994 | Ulrich et al. | 5,955,448 A | 9/1999 | Colaco et al. |
| 5,337,740 A | 8/1994 | Armstrong et al. | 5,957,848 A | 9/1999 | Sutton et al. |
| 5,342,625 A | 8/1994 | Hauer et al. | 5,972,366 A | 10/1999 | Haynes et al. |
| 5,348,852 A | 9/1994 | Bonderman | 5,972,388 A | 10/1999 | Sakon et al. |
| 5,349,947 A | 9/1994 | Newhouse et al. | 5,976,436 A | 11/1999 | Livesley et al. |
| 5,354,562 A | 10/1994 | Platz et al. | 5,989,217 A | 11/1999 | Ohki et al. |
| 5,354,934 A | 10/1994 | Pitt et al. | 5,993,783 A | 11/1999 | Eljamal et al. |
| 5,355,872 A | 10/1994 | Riggs et al. | 5,993,805 A | 11/1999 | Sutton et al. |
| 5,364,838 A | 11/1994 | Rubsamen | 5,994,314 A | 11/1999 | Eljamal et al. |
| 5,366,734 A | 11/1994 | Hutchinson | 5,997,848 A | 12/1999 | Patton |
| 5,376,359 A | 12/1994 | Johnson | 6,013,638 A | 1/2000 | Crystal et al. |
| 5,376,386 A | 12/1994 | Ganderton et al. | 6,019,968 A | 2/2000 | Platz et al. |
| 5,380,473 A | 1/1995 | Bogue et al. | 6,034,080 A | 3/2000 | Colaco et al. |
| 5,384,133 A | 1/1995 | Boyes et al. | 6,051,256 A | 4/2000 | Platz et al. |
| 5,387,431 A | 2/1995 | Fuisz | 6,060,069 A | 5/2000 | Hill et al. |
| 5,403,861 A | 4/1995 | Goldwin et al. | 6,071,428 A | 6/2000 | Franks et al. |
| 5,404,871 A | 4/1995 | Goodman et al. | 6,077,543 A | 6/2000 | Gordon et al. |
| 5,422,360 A | 6/1995 | Miyajima et al. | 6,080,721 A | 6/2000 | Patton |
| 5,422,384 A | 6/1995 | Samuels et al. | 6,089,228 A | 7/2000 | Smith et al. |
| 5,425,951 A | 6/1995 | Goodrich, Jr. et al. | 6,099,517 A | 8/2000 | Daugherty |
| 5,453,514 A | 9/1995 | Niigata et al. | 6,123,924 A | 9/2000 | Mistry et al. |
| 5,458,135 A | 10/1995 | Patton et al. | 6,123,936 A | 9/2000 | Platz et al. |
| 5,466,701 A | 11/1995 | Hlasta et al. | 6,136,346 A | 10/2000 | Eljamal et al. |
| 5,482,927 A | 1/1996 | Maniar et al. | 6,138,668 A | 10/2000 | Patton et al. |
| 5,488,062 A | 1/1996 | Dunlap et al. | 6,138,673 A | 10/2000 | Shepherd |
| 5,506,203 A | 4/1996 | Backstrom et al. | 6,142,216 A | 11/2000 | Lannes |
| 5,512,547 A | 4/1996 | Johnson et al. | 6,165,463 A | 12/2000 | Platz et al. |
| 5,518,709 A | 5/1996 | Sutton et al. | 6,179,164 B1 | 1/2001 | Fuchs |
| 5,547,696 A | 8/1996 | Sorensen | 6,187,344 B1 | 2/2001 | Eljamal et al. |
| 5,554,382 A | 9/1996 | Castor | 6,190,859 B1 | 2/2001 | Putnak et al. |
| 5,563,122 A | 10/1996 | Endo et al. | 6,231,851 B1 | 5/2001 | Platz et al. |

| | | |
|---|---|---|
| 6,257,233 B1 | 7/2001 | Burr et al. |
| 6,258,341 B1 | 7/2001 | Foster et al. |
| 6,290,991 B1 * | 9/2001 | Roser et al. .................. 424/502 |
| 6,303,581 B2 | 10/2001 | Pearlman |
| 6,303,582 B1 | 10/2001 | Eljamal et al. |
| 6,309,671 B1 | 10/2001 | Foster et al. |
| 6,313,102 B1 | 11/2001 | Colaco et al. |
| 6,331,310 B1 | 12/2001 | Roser et al. |
| 6,344,182 B1 | 2/2002 | Sutton et al. |
| 6,358,530 B1 | 3/2002 | Eljamal et al. |
| 6,365,190 B1 | 4/2002 | Gordon et al. |
| 6,367,473 B1 | 4/2002 | Kafer |
| 6,372,258 B1 | 4/2002 | Platz et al. |
| 6,423,334 B1 | 7/2002 | Brayden et al. |
| 6,423,344 B1 | 7/2002 | Platz et al. |
| 6,426,210 B1 | 7/2002 | Franks et al. |
| RE37,872 E | 10/2002 | Franks et al. |
| 6,468,782 B1 | 10/2002 | Tunnacliffe et al. |
| 6,479,049 B1 | 11/2002 | Platz et al. |
| 6,484,715 B1 | 11/2002 | Ritsche et al. |
| 6,503,411 B1 | 1/2003 | Franks et al. |
| 6,509,006 B1 | 1/2003 | Platz et al. |
| 6,514,496 B1 | 2/2003 | Platz et al. |
| 6,518,239 B1 | 2/2003 | Kuo et al. |
| 6,543,448 B1 | 4/2003 | Smith et al. |
| 6,546,929 B2 | 4/2003 | Burr et al. |
| 6,565,841 B1 | 5/2003 | Niven et al. |
| 6,565,871 B2 | 5/2003 | Roser et al. |
| 6,569,406 B2 | 5/2003 | Stevenson et al. |
| 6,569,458 B1 | 5/2003 | Gombotz et al. |
| 6,572,893 B2 | 6/2003 | Gordon et al. |
| 6,582,728 B1 | 6/2003 | Platz et al. |
| 6,586,006 B2 | 7/2003 | Roser et al. |
| 6,589,560 B2 | 7/2003 | Foster et al. |
| 6,591,832 B1 | 7/2003 | DeJonge |
| 6,592,904 B2 | 7/2003 | Platz et al. |
| 6,630,169 B1 | 10/2003 | Bot et al. |
| 6,649,911 B2 | 11/2003 | Kawato |
| 6,655,379 B2 | 12/2003 | Clark et al. |
| RE38,385 E | 1/2004 | Franks et al. |
| 6,673,335 B1 | 1/2004 | Platz et al. |
| 6,681,767 B1 | 1/2004 | Patton et al. |
| 6,685,967 B1 | 2/2004 | Patton et al. |
| 6,737,045 B2 | 5/2004 | Patton et al. |
| 6,737,066 B1 | 5/2004 | Moss |
| 6,752,893 B2 | 6/2004 | Frieder, Jr. |
| 6,794,357 B1 | 9/2004 | Backstrom et al. |
| 6,797,258 B2 | 9/2004 | Platz et al. |
| 6,811,792 B2 | 11/2004 | Roser et al. |
| 6,825,031 B2 | 11/2004 | Franks et al. |
| 7,056,495 B2 | 6/2006 | Roser et al. |
| 2001/0038858 A1 | 11/2001 | Roser et al. |
| 2002/0071871 A1 | 6/2002 | Snyder et al. |
| 2002/0117170 A1 | 8/2002 | Platz et al. |
| 2002/0122827 A1 | 9/2002 | Platz et al. |
| 2002/0127188 A1 | 9/2002 | Platz et al. |
| 2002/0132787 A1 | 9/2002 | Eljamal et al. |
| 2002/0192164 A1 | 12/2002 | Patton et al. |
| 2003/0035778 A1 | 2/2003 | Platz et al. |
| 2003/0040462 A1 | 2/2003 | Franks et al. |
| 2003/0053959 A1 | 3/2003 | Patton et al. |
| 2003/0054040 A1 | 3/2003 | Roser et al. |
| 2003/0068279 A1 | 4/2003 | Platz et al. |
| 2003/0072718 A1 | 4/2003 | Platz et al. |
| 2003/0086877 A1 | 5/2003 | Platz et al. |
| 2003/0092666 A1 | 5/2003 | Eljamal et al. |
| 2003/0113273 A1 | 6/2003 | Patton et al. |
| 2003/0113900 A1 | 6/2003 | Tunnacliffe et al. |
| 2003/0129141 A1 | 7/2003 | Platz et al. |
| 2003/0147961 A1 | 8/2003 | Roser et al. |
| 2003/0171282 A1 | 9/2003 | Patton |
| 2003/0185765 A1 | 10/2003 | Platz et al. |
| 2003/0198601 A1 | 10/2003 | Platz et al. |
| 2003/0203036 A1 | 10/2003 | Gordon et al. |
| 2003/0215512 A1 | 11/2003 | Foster et al. |
| 2003/0215514 A1 | 11/2003 | Platz et al. |
| 2004/0052825 A1 | 3/2004 | Roser et al. |
| 2004/0096400 A1 | 5/2004 | Patton et al. |
| 2004/0096401 A1 | 5/2004 | Patton et al. |
| 2004/0219206 A1 | 11/2004 | Roser et al. |
| 2005/0147566 A1 | 7/2005 | Fleming et al. |
| 2005/0186143 A1 | 8/2005 | Stevenson et al. |
| 2005/0203002 A1 | 9/2005 | Tzannis et al. |

FOREIGN PATENT DOCUMENTS

| | | |
|---|---|---|
| DE | 471 490 | 8/1931 |
| DE | 1 080 265 | 4/1960 |
| DE | 1812574 | 6/1970 |
| DE | 1598326 | 3/1972 |
| DE | 2415159 | 10/1975 |
| DE | 3141498 | 4/1983 |
| DE | 0161072 | 9/1984 |
| DE | 3713326 | 10/1987 |
| EP | 0 015 123 | 3/1980 |
| EP | 0 072 046 | 2/1983 |
| EP | 0 090 356 | 10/1983 |
| EP | 0 111 216 | 6/1984 |
| EP | 0 122 036 | 10/1984 |
| EP | 0 129 985 | 1/1985 |
| EP | 0 136 030 | 4/1985 |
| EP | 0 139 286 | 5/1985 |
| EP | 0 140 489 | 5/1985 |
| EP | 0 222 313 | 5/1987 |
| EP | 0 223 221 | 5/1987 |
| EP | 0 229 810 | 7/1987 |
| EP | 0 244 771 | 11/1987 |
| EP | 0 251 631 | 1/1988 |
| EP | 0 252 750 | 1/1988 |
| EP | 0 257 915 | 3/1988 |
| EP | 0 257 956 | 3/1988 |
| EP | 0 282 179 | 9/1988 |
| EP | 0 297 887 | 1/1989 |
| EP | 0 315 875 | 5/1989 |
| EP | 0 325 936 | 8/1989 |
| EP | 0 356 154 | 2/1990 |
| EP | 0 357 665 | 3/1990 |
| EP | 0 360 340 | 3/1990 |
| EP | 0 364 235 | 4/1990 |
| EP | 0 366 303 | 5/1990 |
| EP | 0 383 569 | 8/1990 |
| EP | 0 407 028 | 1/1991 |
| EP | 0 415 567 | 3/1991 |
| EP | 0 430 045 | 6/1991 |
| EP | 0 433 679 | 6/1991 |
| EP | 0 237 507 | 12/1991 |
| EP | 0 463 653 | 1/1992 |
| EP | 0 469 814 | 2/1992 |
| EP | 0 473 965 | 3/1992 |
| EP | 0 474 874 | 3/1992 |
| EP | 0 289 336 | 9/1992 |
| EP | 0 520 748 | 12/1992 |
| EP | 0 524 748 | 1/1993 |
| EP | 0 582 459 | 2/1994 |
| EP | 0 467 172 | 4/1994 |
| EP | 0 347 779 | 5/1994 |
| EP | 0 600 730 | 6/1994 |
| EP | 0 601 965 | 6/1994 |
| EP | 0 606 486 | 7/1994 |
| EP | 0 611 567 | 8/1994 |
| EP | 0 611 567 A1 * | 8/1994 |
| EP | 0 616 524 | 9/1994 |
| EP | 0 655 237 | 5/1995 |
| EP | 0 714 905 | 6/1996 |
| EP | 0 755 249 | 1/1997 |
| EP | 0 773 781 | 5/1997 |

| | | |
|---|---|---|
| ES | 84-03520 | 6/1984 |
| ES | 2009704 | 1/1989 |
| FR | 2238476 | 3/1975 |
| FR | 2 666 987 | 3/1992 |
| FR | 2 700 279 | 7/1994 |
| GB | 0 821 036 | 8/1968 |
| GB | 1 122 284 | 3/1970 |
| GB | 1 182 779 | 3/1972 |
| GB | 1 288 094 | 9/1972 |
| GB | 1 381 588 | 1/1975 |
| GB | 1 477 775 | 6/1977 |
| GB | 1 527 605 | 10/1978 |
| GB | 1 533 012 | 11/1978 |
| GB | 2 105 189 | 3/1983 |
| GB | 2 126 588 | 3/1984 |
| GB | 2 187 191 | 1/1987 |
| GB | 2 206 273 | 1/1989 |
| GB | 1 265 615 | 3/1989 |
| GB | 2 248 550 | 4/1992 |
| JP | 52-139789 | 11/1977 |
| JP | 56-138110 | 10/1981 |
| JP | 57-21315 | 2/1982 |
| JP | 58-216695 | 12/1983 |
| JP | 59-095885 | 6/1984 |
| JP | 60-244288 | 12/1985 |
| JP | 62-228272 | 10/1987 |
| JP | 62-255434 | 11/1987 |
| JP | 62-267238 | 11/1987 |
| JP | 63-502592 | 9/1988 |
| JP | 2-000111 | 3/1990 |
| JP | 2-084401 | 3/1990 |
| JP | 3-264537 | 11/1991 |
| JP | 06-100464 | 4/1994 |
| WO | WO 92/18164 | 10/1982 |
| WO | WO 86/00336 | 1/1986 |
| WO | WO 86/04095 | 7/1986 |
| WO | WO 87/00196 | 1/1987 |
| WO | WO 87/02038 | 4/1987 |
| WO | WO 87/05300 | 9/1987 |
| WO | WO 87/07502 | 12/1987 |
| WO | WO 88/04556 | 6/1988 |
| WO | WO 88/08298 | 11/1988 |
| WO | WO 89/05158 | 6/1989 |
| WO | WO 89/06542 | 7/1989 |
| WO | WO 89/06976 | 8/1989 |
| WO | WO 89/09614 | 10/1989 |
| WO | WO 90/05182 | 5/1990 |
| WO | WO 90/07351 | 7/1990 |
| WO | WO 90/09780 | 9/1990 |
| WO | WO 90/09781 | 9/1990 |
| WO | WO 90/11756 | 10/1990 |
| WO | WO 90/13285 | 11/1990 |
| WO | WO 90/13328 | 11/1990 |
| WO | WO 90/15635 | 12/1990 |
| WO | WO 91/02545 | 3/1991 |
| WO | WO 91/02558 | 3/1991 |
| WO | WO 91/06282 | 5/1991 |
| WO | WO 91/16038 | 10/1991 |
| WO | WO 91/16882 | 11/1991 |
| WO | WO 91/18091 | 11/1991 |
| WO | WO 92/02133 | 2/1992 |
| WO | WO 92/10515 | 6/1992 |
| WO | WO 92/19243 | 11/1992 |
| WO | WO 92/20391 | 11/1992 |
| WO | WO 93/00951 | 1/1993 |
| WO | WO 93/02712 | 2/1993 |
| WO | WO 93/02834 | 2/1993 |
| WO | WO 93/09832 | 5/1993 |
| WO | WO 93/10758 | 6/1993 |
| WO | WO 93/11220 | 6/1993 |
| WO | WO 93/11746 | 6/1993 |
| WO | WO 93/12240 | 6/1993 |
| WO | WO 93/13752 | 7/1993 |
| WO | WO 93/17663 | 9/1993 |
| WO | WO 93/23065 | 11/1993 |
| WO | WO 93/23110 | 11/1993 |
| WO | WO 94/00291 | 1/1994 |
| WO | WO 94/02107 | 3/1994 |
| WO | WO 94/07514 | 4/1994 |
| WO | WO 94/08552 | 4/1994 |
| WO | WO 94/13271 | 6/1994 |
| WO | WO 94/16717 | 8/1994 |
| WO | WO 94/22423 | 10/1994 |
| WO | WO 94/24263 | 10/1994 |
| WO | WO 95/00127 | 1/1995 |
| WO | WO 95/00128 | 1/1995 |
| WO | WO 95/01324 | 1/1995 |
| WO | WO 95/03395 | 2/1995 |
| WO | WO 95/05805 | 3/1995 |
| WO | WO 95/06126 | 3/1995 |
| WO | WO 95/06491 | 3/1995 |
| WO | WO 95/11666 | 5/1995 |
| WO | WO 95/20979 | 8/1995 |
| WO | WO 95/23613 | 9/1995 |
| WO | WO 95/24183 | 9/1995 |
| WO | WO 95/28151 | 10/1995 |
| WO | WO 95/31479 | 11/1995 |
| WO | WO 95/33488 | 12/1995 |
| WO | WO 96/03978 | 2/1996 |
| WO | WO 96/05809 | 2/1996 |
| WO | WO 96/09085 | 3/1996 |
| WO | WO 96/27393 | 9/1996 |
| WO | WO 96/32096 | 10/1996 |
| WO | WO 96/32116 | 10/1996 |
| WO | WO 96/32149 | 10/1996 |
| WO | WO 96/32152 | 10/1996 |
| WO | WO 96/33744 | 10/1996 |
| WO | WO 96/40049 | 12/1996 |
| WO | WO 96/40077 | 12/1996 |
| WO | WO 97/34689 | 9/1997 |
| WO | WO 97/41031 | 11/1997 |
| WO | WO 97/41833 | 11/1997 |
| WO | WO 98/16205 | 4/1998 |
| WO | WO 98/24882 | 6/1998 |
| WO | WO 98/58989 | 12/1998 |
| WO | WO 99/16419 | 4/1999 |
| WO | WO 99/32083 | 7/1999 |
| WO | WO 01/87278 | 11/2001 |

OTHER PUBLICATIONS

Crowe, J. H. et al., (1988). "Interactions of Sugars With Membranes," *Biochimica et Biophysica Acta*, 947:367-384.

Crowe, J. H. et al., (1990). "Are Freezing And Dehydration Similar Stress Vectors? A Comparison of Modes of Interaction of Stabilizing Solutes With Biomolecules" (1990) *Cryobiol.* 27:219-231.

Daemen, A. L. H. et al., (1982). "The Destruction of Enzymes and Bacteria During the Spray-Drying of Milk and Whey, 2. The Effect of the Drying Conditions," *Neth. Milk Dairy J.* 36:211-229.

Dalby, R. N. et al., (2003). "Inhalation Therapy: Technological Milestones in Asthma Treatment," *Advanced Drug Delivery* 55:779-791.

Dalby, R. N. et al., (Oct. 1988). "Relationship Between Particles Morphology and Drug Release Properties After Hydration of Aerosols Properties After Hydration of Aerosols Containing Liposome Forming Ingredients," *Pharmaceutical Research* 5(10):S-94.

Darrington, R. T. et al., (Mar. 1995). "Evidence for a Common Intermediate in Insulin Deamidation and Covalent Dimer Formation: Effects of pH and Aniline Trapping in Dilute Acidic Solutions," *Journal of Pharmaceutical Sciences* 84(3):275-282.

*Development of a dry and thermostable oral polio vaccine*, Progress Report QHCL, RIVM and RUG, May 1993-Oct. 1993, (Apr. 22, 1994), 9 pages total.

*Development of a dry and thermostable oral polio vaccine*, Progress Report QHCL and RIVM Nov. 1993-Apr. 1994, (Apr. 22, 1994), 11 pages total.

Dialog® English Abstract of French Patent No. 2238476 (Mar. 28, 1975).

Dialog® English Abstract of Japanese Publication No. 58-216695 (Dec. 16, 1983), Japanese Patent Application No. 82-98125 filed Jun. 7, 1982.

Dialog® English Abstract of Japanese Publication No. 63-502592 (Sep. 29, 1988), Japanese Patent Application No. 87501509, national phase of PCT Publication No. WO 87/05300.

Edwards, A. D. et al., (Aug. 20010. Crystallization of Pure Anhydrous Polymorphs of Carbamazepine by Solution Enhanced Dispersion With Supercritical Fluids (SEDS™) *Journal of Pharmaceutical Sciences* 90(8):1115-1124.

Eleutherio, E.C.A. et al., (1993). "Role of the Trehalose Carrier in Dehydration Resistence of Saccharomyces Cerevisiae," *Biochimica et Biophysica Acta*, 1156:263-266.

Encyclopaedia Chimica, panel of Kagaku-Daijiten, Ed., vol. 7, pp. 310, 311 and English translation (1964).

Facsimile from Dr. D. L. Smith to Dr. B. Roser regarding product information of Stop'n Grow, (Jun. 26, 1997), 7 pages.

Fakes, M. G. et al, (Apr. 2000). "Moisture Sorption Behavior of Selected Bulking Agents Used in Lyophilized Products," *PDA J. Pharm Sci. Technol.* 54(2):144-149, Abstract only at http://www.ncbi.nlm.nih.gov.

Finnar, I. L. (1996). "§14. Trehalose, m.p. 203° C," under "Carbohydrate", *Organic Chemistry*, vol. 2, Stereochemistry and the Chemistry of Natural Products, $5^{th}$ edition, Longman, p. 323.

Forbes, R. T. et al., (Nov. 1998). "Water Vapor Sorption Studies on the Physical Stability of a Series of Spray-Dried Protein/Sugar Powders for Inhalation," *Journal of Pharmaceutical Sciences* 87(11):1316-1321.

Franks, F. (Apr. 1994). "Accelarated Stability Testing of Bioproducts: Attractions and Pitfalls," *TIBTECH* 12:114-117.

Green, J. L. et al., (1994). "The Protein-Glass Analogy: Some Insights from Homopeptide Comparisons," *J. Phys. Chem.* 98:13780-13790.

Green, J.L. et al., (1989). "Phase Relations and Vitrification in Saccharide-Water Solutions and the Trehalose Anomaly," *J. Phys. Chem.* 93:2880-2882.

Grounds of Decision for Opposition of Japanese Patent Application No. 63-505533, pp. 1-6 (Jul. 1996) with English translation.

Hahn, L. et al., (1989) "Solid Surfactant Solutions Of Active Ingredients In Sugar Esters," *Pharmaceutical Research* 6:958-960.

Jameel, F. et al., (2001). "Freeze Drying Properties of Some Oligonucleotides," *Pharmaceutical Development and Technology* 6(2):151-157.

Japanese Document Regarding Opposition To Japanese Patent Application No. 63-505533 (English Translation Included), Abridged Translation Of Specification For PCT Patent Publication No. WO 87/00196, 1 page.

Jovanovic-Peterson, L. et al. (1993). "Jet-injected insulin is associated with decreased antibody production and postprandial glucose variability when compared with needle-injected insulin in gestational diabetic women," *Diabetes Care* 16(11):1479-1484.

Kachura, (1985). "Method of Drying Lactic Acid Bacteria," *Vinodelie I Vinogradarstvo* SSSR 2:49-50, English Abtract only, one page.

Kanna, K. et al., (1974) "Denaturation of Fish Muscle Protein by Dehydration—V." *Bull. Tokai Reg. Fish. Res. Lab.* 77:1-17.

Karmas, R. et al., (1992). "Effect of Glass Transition on Rates of Nonenzymatic Browning in Food Systems," *J. Agric. Food Chem.* 40:873-879.

Khan, R. (1984). "Chemistry And New Uses of Sucrose: How Important?" *Pure & Appl. Chem.* 56(7):833-844.

Khan, R. et al. (1990). "Cyclic Acetals of 4,1',6'-Trichloro-4,1',6'-Trideoxy-Galacto-Sucrose And Their Conversion Into Methyl Ether Derivatives," *Carb. Res.* 198:275-283.

Klein, T. M. et al., (1987). "High Velocity Microprojectiles For Delivering Nucleic Acids Into Living Cells," *Nature* 327:70-73.

Labuza, T. et al., (Jan. 1992). "Glass Transition Temperatures of Food Systems," at http://faculty.che.umn.edu/fscn/Ted_Labuza/PDF_files/Isotherm_Folder/Tg%20compilation.pdf, visited on Sep. 2005.

Lai, M. C. et al., (May 1999). "Solid-State Chemical Stability of Proteins and Peptides," *Journal of Pharmaceutical Sciences* 88(5):489-500.

Laube, B. L. et al., (Oct. 2000). "Targeting Aerosol Deposition in Patients With Cystic Fibrosis, Effects of Alterations in Particle Size and Inspiratory Flow Rate," *Chest* 118(4):1069-1076.

Ledl, F., et al., (Jun. 1990). "New Aspects Of The Maillard Reaction In Foods And In The Human Body," *Ang. Chem. Int. Ed. Engl.* 29:565-594.

Lee, C. K. (1980). *Developments in Food Carbohydrate*—2nd edition Applied Science Publishers, London, Table of Contents, 4 pages.

Lee, G. (2002). "Chapter 6: Spray Drying of Proteins," in *Rational Design of Stable Protein Formulations, Theory and Practice*, J. F. Carpenter & M. Manning, pp. 1-39.

Leslie, S. B. et al., (Oct. 1995). "Trehalose and sucrose protect both membranes and proteins in intact bacteria during drying" *Appl. Env. Microbiol.* 61(10):3592-3597.

Leuner, C. et al. (2000). "Improving Drug Solubility for Oral Delivery Using Solid Dispersions," *European Journal of Pharmaceutics and Biopharmaceutics* 50:47-60.

Levine, Harry & Slade, Louise (May 1992). "Another View of Trehalose for Drying and Stabilizing Biological Materials," *Biopharm* 5:36-40.

Li, Z. et al., (2002). "Realistic In Vitro Assessment of Dry Powder Inhalers," *Respiratory Drug Delivery* VIII, pp. 687-689.

Lin, S.-Y. et al., (1989). "Solid Particles of Drug-β-Cyclodextrin Inclusion Complexes Directly Prepared by a Spray-Drying Technique," *Internation Journal of Pharmaceutics*, 56:249-259.

Louey, M. D. et al., (2004). "Controlled Release Products for Respiratory Delivery," This article was published in the Jul./Aug. 2004 issue of APR, vol. 7, Issue 4, on pp. 82-87, at http://www.americanpharmaceuticalreview.com/article.aspx?article=77, visited on Sep. 2005, 11 pages.

Louis, P. et al., (1994). "Survival Of *Escherichia coli* During Drying And Storage In The Presence Of Compatible Solutes" *Appl. Microbiol. Biotechnol.* 41:684-688.

Lueckel, B. et al., (1998). "Effects of Formulation and Process Variables on the Aggregation of Freeze-Dried Interleukin-6 (IL-6) After Lyophilization and on Storage," *Pharmaceutical Development and Technology* 3(3):337-346.

Matsuda, Y. et al., (Nov. 7, 1991). "Amorphism and Physicochemical Stability of Spray-Dried Frusemide," *J. Pharm. Pharmacol.* 44:627-633.

Miller, D. P. et al., (1998). "Stabilization of Lactate Dehydrogenase Following Freeze-Thawing and Vacuum-Drying in the Presence of Trehalose and Borate," *Pharmaceutical Research* 15(8):1215-1221.

Molina, M. C. et al., (Sep. 2004). "The Stability of Lyophilized Lipid/DNA Complexes During Prolonged Storage," *J. Pharm. Sci.* 93(9):2259-2273, abstract only, one page, at http://www.ncbi.nlm.nih.gov, visited on Sep. 2005.

Mouradian, R. et al., (1985). Degradation of Functional Integrity During Long-Term Storage of.

Pikal, M. J. (Oct. 1990). "Freeze-Drying of Proteins Part II: Formulation Selection," *Biopharm* 3(8):26-30.

Franks, F. (1990). "Freeze Drying: From Empiricism to Predicatability," *Cryo-Letters* 11:93-110.

Franks, F. (Oct. 1991). "Materials Science and the Production of Shelf-Stable Biologicals," *Pharmaceutical Technological International* 24:24-34.

Roser, R. *Trehalose Drying: A Novel Replacement for Freeze-Drying* 4(7) Biopharm 47-53 (Sep. 1991).

Labrude, P. et al., (1989). "Protective Effect of Sucrose on Spray Drying of Ocxyhemoglobin," *Journal of Pharmaceutical Sciences*, 78(3):223-229.

Broadhead, J. et al., *The Spray Drying of Pharmaceuticals*, 18 Drug Development and Industrial Pharmacy 1169-1206 (1992).

Whittier, E. *Lactose and its Utilization: A Review*, 27(7) J. Dairy Sci. 505-537 (Jul. 1944).

Makower, B. & W. Dye, (Jan. 1956) "Equilibrium Moisture Content and Crystallization of Amorphous Sucrose and Glucose, "*Agric. and Food Chem.* 4(1):72-77.

Bell, J. H. et al., *Dry Powder Aerosols I: A New Powder Inhalation Device*, 60(10) J. Pharm. Sci. 1559-1564 (Oct. 1971).

Hickey, A. J. (1992). "Methods of Aerosol Particle Size Characterization," Chapter 8,Hicke y, ed. *Pharmaceutical Inhalation Aerosol Technology*, pp. 219-253.

Bandara, G. et al., (Nov. 1993) "Interarticular Expression of Biologically Active Interleukin 1-Receptor-Antagonist Protein by Ex Vivo Gene Transfer," *Proc. Natl. Acad. Sci.*

Dose, K. et al. *Survival in Extreme Dryness and DNA-Single-Strand Breaks* 12(4) Advances in Space Research (4)221-(4)229 (1992).

Roser U.S. Appl. No. 08/349,029, filed Dec. 2, 1994, Paper No. 40, Amendment under 37 C.F.R. § 1.111, mailed on Dec. 29, 1999 (Patent No. 6,290,991).

Craig, I. D. et al., (2001). "Maillard Reaction Kinetics in Model Preservation Systems in the Vicinity of the Glass Transition: Experiment and Theory," *J. Agric. Food Chem.* 49(10):4706-4711.

Carpenter, John F. et al., *Rational Design of Stable Lyophilized Protein Formulations: Some Practical Advice*, 14:8 Pharmaceutical Res. 969-975 (1997).

Nektar U.S. Appl. No. 10/245,706, filed Sep. 18, 2002, Non-Final Office Action, Paper No. 6, mailed Feb. 26, 2003.

Nektar U.S. Appl. No. 10/245,706, filed Sep. 18, 2002, Reply to Office Action, mailed on May 27, 2003.

Preliminary Amendment, Paper No. 4, mailed Sep. 18, 2002 from the prosecution history of U.S. Appl. No. 10/245,722, Pub. No. US 2003/0092666 ("the '722 Application"), filed Sep. 18, 2002, (the Application-in-Interference).

Underwood, Stephen L. et al., *A Novel Technique for the Administration of Bronchodilator Drugs Formulated as Dry Powders to the Anaesthetized Guinea Pig*, 26 J. Pharm. Methods 203-210 (1991).

Stribling, Roscoe et al., *The Mouse as a Model for Cationic Liposome-Based Aerosolized Gene Delivery*, 3(1/2),J. Biopharm. Sci. 255-263 (1992).

Nektar U.S. Appl. No. 08/044,358 filed Apr. 7, 1993, Paper No. 5, Amendment dated Feb. 23, 1994 (Abandoned).

Crowe, Lois M. et al (Oct. 1996). "Is Trehalose Special for Preserving Dry Biomaterials?" *Biophysical Journal* 71:2087-2093.

Crowe, John H. et al., (1998). "The Role of Vitrification In Anhydrobiosis," *Annu. Rev. Physiol.* 60:73-103.

Singer, Mike A. & Lindquist, Susan (Nov. 1998) Thermotolerance in *Saccharomyces*.

Agrimi, U. et al., (Feb. 1993) *Med. Hypotheses* 40(2):113-116.

Akers, M. J. et al., (1995). "Glycine Crystallization During Freezing: The Effects of Salt Form, pH, and Ionic Strength," *Pharmaceutical Research* 12(10):1457-1461.

Akoh et al. (1987) "One-stage synthesis of raffinose fatty acid polyesters" *J. Food Sci.* 52:1570-1576.

Allison, S. D. et al., (Aug. 2001) "Lyophilization of Nonviral Gene Delivery Systems," *Methods in Molecular Medicine*, Series Methods in Molecular Medicine, vol. 65, pp. 225-252.

Allison, S. D. et al., (May 2000). "Mechanisms of Protection of Cationic Lipid-DNA Complexes During Lyophilization," *Journal of Pharmaceutical Sciences* 89(5):682-691.

Amal, A. et al., (20020. "Integrity of Crystalline Lysozyme Exceeds that of a Spray-Dried Form," *International Journal of Pharmaceutics* 247:79-90.

Anekwe, J. U. et al., (1998). "Relaxation Constants as a Predictor of Protein Stabilization," *Biocalorimetry: Applications of Calorimetry in the Biological Science*, J. E. Ladbury, and B.Z. Chowdhry (eds.), John Wiley & Sons, 243-251.

Banker, G. S. et al. (eds), (1996). "Drug Absorption and Availability," *Modern Pharmaceutics*, 3rd edition, Marcel Dekker, Inc,. p. 145.

Barnett, A. H. (Apr. 2004). "Exhubera Inhaled Insulin: A Review," *Int. J. Clin. Pract.* 58(4):394-401.

Bigsbee, D. R. (Oct. 1993). "Solid State Liability of Insulin: Comparison of Crystalline and Amorphous Forms," *Pharmaceutical Research* 10(10):Abstract No. PDD 7418, p. S-279.

Blakeley et al., (1990) "Dry instant blood typing plate for bedside use" *Lancet* 336:854-855.

Bögelein, J. et al., (2003). "Influence of Amorphous Mannitol on Powder Properties of Spray Dried Trehalose/Dextran Mixtures," at http://www.pharmtech.uni-erlangen.de/APV_03_abs/bogelein.pdf, visited on Sep. 2005, 2 pages.

Bootsma, H. P. R. et al., (1989). "β-Cyclodextrin as an Excipient in Solid Oral Dosage Forms: In Vitro and In Vivo Evaluation of Spray-Dried Diazepan-β-Cyclodextrin Products," *International Journal of Pharmaceutics* 51:213-223.

Bosquillon, C. et al., (2004). "Aerosolization Properties, Surface Composition and Physical State of Spray-Dried Protein Powders," *Journal of Controlled Release* 99:357-367.

Branchu, S. et al., (1998). "The Effect of Cyclodextrins on Monomeric Protein Unfolding," *Biocalorimetry: Applications of Calorimetry in the Biological Science*, J. E. Ladbury and B.Z. Chowdhry, John Wiley &Sons, Ltd., 297-301.

Branchu, S. et al., (1999). "Hydroxypropyl-β-Cyclodextrin Inhibits Spray-Drying-Induced Inactivation of β-Galactosidase," *Journal of Pharmaceutical Sciences* 88(9):905-911.

Brange, J. et al., (1992). "Chemical Stability of Insulin. 1. Hydrolytic Degradation During Storage of Pharmaceutical Preparations," *Pharmaceutical Research* 9(6):715-726.

Breitenbach, J. (2002). "Melt Extrusion: From Process to Drug Delivery Technology," *European Journal of Pharmaceutics and Biopharmaceutics* 54:107-117.

Broadhead, J. et al., *The Effect of Process and Formulation Variable on the Properties of Spray-Dried β-Galactosidase*, 46(6) J. Pharm. Pharmacol. 458-467 (Jun. 1994).

Brown, P. et al., (1990). "A Therapeutic Panorama of the Spongiform Encephalopaties," *Antiviral Chem. Chemother.* 1(2):75-84.

Burvall, A. et al., (1978). "Storage of Lactose-Hydrolised Dried Milk: Effect of Water Activity on the Protein Nutritional Value," *Journal of Dairy Research* 45:381-389.

Caughey, B. et al., (1993). "Sulphated Polyanion Inhibition of Scrapie-Associated PrP Accumulation in Cultured Cells," *J. Virol.* 67(2):643-650.

Chan, T. W. et al., (1988). "Formulation of Vaccine Adjuvant Muramyldipeptides (MDP). I. Characterization of Amorphous and Crystalline Forms of a Muramyldipeptide Analogue," *Pharmaceutical Research* 5(8):523-527.

Chavan, V. et al., (2000). "Effect of Rise in Simulated Inspiratory Flow Rate and Carrier Particle Size on Powder Emptying From Dry Powder Inhalers," *AAPS Pharmsci 2000*; 2(2) article 10 at http://www.pharmsci.org, 7 pages.

Chavan, V. et al., (2002). "Novel System to Investigate the Effects of Inhaled Volume and Rates of Rise in Simulated Inspiratory Air Flow on Fine Particle Output From a Dry Powder Inhaler," *AAPS Pharmasci 2002*; 4(2) article 6 at http://www.aapspharmsci.org, 6 pages.

Chavan, V. S. et al., (1999). "Effect of Particle Size and Rise in Simulated Inspiratory Flow Rate on Device Emptying in a Dry Powder Inhaler System," at htpp://www.aapspharmsci.org/abstracts/AM_1999/1001.htm, visited on Jan. 7, 2005, 1 page.

Chawla, A. et al., (1994). "Production of Spray Dried Salbutamol Sulphate for Use in Dry Powder Aerosol Formulation," *International Journal of Pharmaceutics* 108:233-240.

Chiou et al., (Sep. 1971) "Pharmaceutical Applications of Solid Dispersion Systems" *J. Pharm.* 60(9):1281-1302.

Cleland, J. F. et al., (1993). "The Development of Stable Protein Formulations: A Close Look at Protein Aggregation, Deamidation, and Oxidation," *Critical Reviews in Therapeutic Drug Carrier Systems*, 10(4):307-377.

Cline, D. et al., (2002). "Predicting the Quality of Powders for Inhalation From Surface Energy and Area," *Pharmaceutical Research* 19(9):1274-1277.

Cline, D. et al., (2002). "Predicting the Quality of Powders for Inhalation," *Respiratory Drug Delivery VIII* 683-685.

Colaco, C. et al., (1992) "Trehalose Stabilization of Biological Molecules" *Biotechnol. Internat.* pp. 345-350.

Colaco, C. et al., (1994). "Chapter 14: Chemistry of Protein Stabilization by Trehalose," *ACS Symposium Series 567, Formulation and Delivery of Proteins and Peptides*, J. L. Cleland & R. Langer, pp. 222-240.

Considine, G. D. et al., (2002). *Van Nostrand's Scientific Encyclopedia*, 9th edition, vol. 2, Wiley-Interscience, John Wiley & Sons, Inc., Definition of Vaccines: pp. 3591-3592.

Costantino, H. R. et al., (1994). "Moisture-Induced Aggregation of Lyophilized Insulin," *Pharmaceutical Research* 11(1):21-29.

Crowe, J. H. et al., (1988). "Interactions of Sugars With Membranes," *Biochimica et Biophysica Acta*, 947:367-384.

Crowe, J. H. et al., (1990). "Are Freezing And Dehydration Similar Stress Vectors? A Comparison of Modes of Interaction of Stabilizing Solutes With Biomolecules" (1990) *Cryobiol.* 27:219-231.

Daemen, A. L. H. et al., (1982). "The Destruction of Enzymes and Bacteria During the Spray-Drying of Milk and Whey, 2. The Effect of the Drying Conditions," *Neth. Milk Dairy J.* 36:211-229.

Dalby, R. N. et al., (2003). "Inhalation Therapy: Technological Milestones in Asthma Treatment," *Advanced Drug Delivery* 55:779-791.

Dalby, R. N. et al., (Oct. 1988). "Relationship Between Particles Morphology and Drug Release Properties After Hydration of Aerosols Properties After Hydration of Aerosols Containing Liposome Forming Ingredients," *Pharmaceutical Research* 5(10):S-94.

Darrington, R. T. et al., (Mar. 1995). "Evidence for a Common Intermediate in Insulin Deamidation and Covalent Dimer Formation: Effects of pH and Aniline Trapping in Dilute Acidic Solutions," *Journal of Pharmaceutical Sciences* 84(3):275-282.

Derwent® WPI File 351, English Abstract of Japanese Application No. 82-98125 filed (Jun. 7, 1982).

Derwent® WPI File 351, English Abstract of PCT Publication No. WO 87/05300 (Sep. 11, 1987), also Japanese Publication No. 63-502592.

*Development of a dry and thermostable oral polio vaccine*, Progress Report QHCL, RIVM and RUG, May-Oct. 1993, (Apr. 22, 1994), 9 pages total.

*Development of a dry and thermostable oral polio vaccine*, Progress Report QHCL and RIVM Nov. 1993-Apr. 1994, (Apr. 22, 1994), 11 pages total.

Dialog® English Abstract of French Patent No. 2238476 (Mar. 28, 1975).

Dialog® English Abstract of Japanese Publication No. 58-216695 (Dec. 16, 1983), Japanese Patent Application No. 82-98125 filed Jun. 7, 1982.

Dialog® English Abstract of Japanese Publication No. 63-502592 (Sep. 29, 1988), Japanese Patent Application No. 87501509, national phase of PCT Publication No. WO 87/05300.

Edwards, A. D. et al., (Aug. 20010. Crystallization of Pure Anhydrous Polymorphs of Carbamazepine by Solution Enhanced Dispersion With Supercritical Fluids (SEDS™) *Journal of Pharmaceutical Sciences* 90(8):1115-1124.

Eleutherio, E.C.A. et al., (1993). "Role of the Trehalose Carrier in Dehydration Resistence of *Saccharomyces cerevisiae,*" *Biochimica et Biophysica Acta*, 1156:263-266.

Encyclopaedia Chimica, panel of Kagaku-Daijiten, Ed., vol. 7, pp. 310, 311 and English translation (1964).

Facsimile from Dr. D. L. Smith to Dr. B. Roser regarding product information of Stop'n Grow, (Jun. 26, 1997), 7 pages.

Fakes, M. G. et al, (Apr. 2000). "Moisture Sorption Behavior of Selected Bulking Agents Used in Lyophilized Products," *PDA J. Pharm Sci. Technol.* 54(2):144-149, Abstract only at http://www.ncbi.nlm.nih.gov.

Finnar, I. L. (1996). "§14. Trehalose, m.p. 203° C.," under "Carbohydrate", *Organic Chemistry*, vol. 2, Stereochemistry and the Chemistry of Natural Products, 5th edition, Longman, p. 323.

Forbes, R. T. et al., (Nov. 1998). "Water Vapor Sorption Studies on the Physical Stability of a Series of Spray-Dried Protein/Sugar Powders for Inhalation," *Journal of Pharmaceutical Sciences* 87(11):1316-1321.

Franks, F. (Apr. 1994). "Accelarated Stability Testing of Bioproducts: Attractions and Pitfalls," *TIBTECH* 12:114-117.

Green, J. L. et al., (1994). "The Protein-Glass Analogy: Some Insights from Homopeptide Comparisons," *J. Phys. Chem.* 98:13780-13790.

Green, J.L. et al., (1989). "Phase Relations and Vitrification in Saccharide-Water Solutions and the Trehalose Anomaly," *J. Phys. Chem.* 93:2880-2882.

Hahn, L. et al., (1989) "Solid Surfactant Solutions Of Active Ingredients In Sugar Esters," *Pharmaceutical Research* 6:958-960.

Hancock, B. C. et al., (1993). "The Use of Solution Theories for Predicting Water Vapor Absorption by Amorphous Pharmaceutical Solids: A Test of The Flory-Huggins and Vrentas Models," *Pharmaceutical Research* 10(9):1262-1267.

Hancock, B. C. et al., (1995). "Molecular Mobility of Amorphous Pharmaceutical Solids Below Their Glass Transition Temperatures," *Pharmaceutical Research* 12(6):799-806.

Hancock, B. C. et al., (1999). "The Effect of Temperature on Water Vapor Sorption by Some Amorphous Pharmaceutical Sugars," *Pharmaceutical Development and Technology* 4(1):125-131.

Hancock, B. C. et al., (Jan. 1997). "Characteristics and Significance of the Amorphous State in Pharmaceutical Systems," *J. of Pharmaceutical Sciences* 86(1):12.

Hancock, B. C. et al., (Oct. 1993). "The Relationship Between the Glass Transition Temperature and Water Content of Amorphous and Partially Amorphous Pharmaceutical Solids," *Pharmaceutical Research*, 10(10):p. S-279, Abstract No. PDD 7419.

Hatley, R. H. M. et al., (1996). "Stabilization of Labile Materials by Amorphous Carbohydrates-Glass Fragility and the Physiochemical Properties that Make Trehalose a Superior Excipient," *Pharmaceutical Research* 13(9 Suppl.):S274.

Hawley's Condensed Chemical Dictionary, (1993). 12th Edition, Revised by J. Lewis, Sr., Von Nostrand Reinhold Company, pp. 16-17, 374, 938.

Heitefuss, R. et al., (1959). "The Stabilization of Extracts of Cabbage Leaf Proteins by Polyhydroxy Compounds for Electrophoretic and Immunological Studies," *Archives of Biochemistry and Biophysics* 85:200-208.

Herrington, T. M. et al., (1984). "Physico-Chemical Studies on Sugar Glasses. I. Rates of Crystallization," *Journal of Food Technology* 19:409-425.

Hickey, A. J. et al., (1993). "Behavior of Hygroscopic Pharmaceutical Aerosols and the Influence of Hydrophobic Additives," *Pharmaceutical Research* 10(1):1 -7.

Ibrahim, A. L. et al., (1983). "Spray Vaccination With an Improved F Newcastle Disease Vaccine. A Comparison of Efficacy With the B1 and La Sota Vaccines," *Br. Vet. J.* 139:213-219.

Igaki, N. et al., (1991). "The Inhibition of the Maillard Reaction by L Lysine In-Vitro," *J. Jpn. Diabetes Soc.* 34(5):403-407.

Mouradian, R. et al., (1985). "Degradation of Functional Integrity During Long-Term Storage of a Freeze-Dried Biological Membrane," *Cryobiology* 22:119-127.

Mumenthaler, M. et al., (1994). "Feasibility Study on Spray-Drying Protein Pharmaceuticals: Recombinant Human Growth Hormone and Tissue-Type Plasminogen Activator," *Clinical Research* 11(1):12-20.

Murphy, B. R. et al., (1990). "Chapter 19: Immunization Against Viruses," in *Fields of Virology*, 2nd edition, vol. 1, Raven Press, pp. 469-502.

Naini, V. et al., (1996). "Particles for Inhalation Produced by Spray Drying and Electrostatic Precipitation of Different Protein-Sugar Solutions," *Respiratory Drug Delivery V*, pp. 382-384.

Naini, V. et al., (1998). "Physicochemical Stability of Crystalline Sugars and Their Spray-Dried Forms: Dependence Upon Relative Humidity and Suitability for Use in Powder Inhalers," *Drug Development and Industrial Pharmacy* 24(10):895-909.

Niven, R. W. (19950. "Delivery of Biotherapeutics by Inhalation Aerosol," *Critical Reviews in Therapeutic Drug Carrier Systems*, 12(2&3):151-231.

Niven, R. W. (Jul. 1993). "Delivery of Biotherapeutics by Inhalation Aerosols," *Pharmaceutical Technology* 72:73-74, 80.

Norberg, J. et al., (Sep. 1996). "Glass Transition in DNA From Molecular Dynamics Simulation," *Proc. Natl. Acad. Sci. USA* 93:10173-10176.

Odegard, P. S. et al., (May 2005). "Inhaled Insulin: Exubera," *The Annals of Pharmacotherapy* 39:843-853.

Ohtake, S. et al., (Sep. 20040. "Effect of pH, Counter Ion and Phosphate Concentration on the Glass Transition Temperature of Freeze-Dried Sugar-Phosphate Mixtures," *Pharmaceutical Research* 21(9):1615-1621.

Okamoto, H. et al., (20020. "Dry Powders for Pulmonary Delivery of Peptides and Proteins," *Kona No.* 20:71-83.

Oksanen, C. A. et al., (1990). "The Relationship Between the Glass Transition Temperature and Water Vapor Absorption by Poly(Vinylpyrrolidone)," *Pharmaceutical Research* 7(6):654-657, and errata on p. 974.

Okumura, K. et al., (Jan. Feb. 1994). "Intratracheal Delivery of Calcitonin Dry Powder in Rats and Human Volunteers," *S.T.P. Pharmaceutical Sciences* 4(1):5 pages.

Owens, D. R. et al., (20030. "Alternative Routes of Insulin Delivery," *Diabetic Medicine* 20:886-898.

Palmer, K. J. et al. (Jan. 1956). "X-Ray Diffractometer and Microscopic Investigation of Crystallization of Amorphous Sucrose," *Agricultural and Food Chemistry* 4(1):76-81.

Patel, M. M. et al., (Oct. 2004). "Degradation Kinetics of High Molecular Weight Poly(L-Lactide) Microspheres and Release Mechanism of Lipid: DNA Complexes," *Journal of Pharmaceutical Sciences*, 93(10):2573-2584.

Phillips, E. et al., (1998). "Size Reduction of Peptides and Proteins by Jet-Milling," *Respiratory Drug Delivery VI*, pp. 161-167.

Pikal, M. J. et al., (1997). "The Stability of Insulin in Crystalline and Amorphous Solids: Observation of Greater Stability for the Amorphous Form," *Pharmaceutical Research* 14(10):1379-1387.

Pikal, M. J. et al., (1998). Errata of "The Stability of Insulin in Crystalline and Amorphous Solids: Observation of Greater Stability for the Amorphous Form," *Pharmaceutical Research* 15(2):362-363.

Pine, S. H. et al., (1980). "15-3 Oligosaccharides and Polysaccharides," *Organic Chemistry*, 4$^{th}$ edition, McGraw-Hill International Book Company, p. 763.

Pisecky, J. (1997). "2. Evaporation and Membrane Filtration," in *Handbook of Milk Powder Manufacture*, Niro A/S, Denmark, p. 3.

Pocchiari, M. et al. (1989). "Amphotericin B: A Novel Class of Antiscrapie Drugs," *J. Infect. Dis.* 160(5):795-802.

Prestrelski, S. J. et al., (1995). "Optimization of Lyophilization Conditions for Recombinant Human Interleukin-2 by Dried-State Conformational Analysis Using Fourrier-Transform Infrared Spectroscopy," *Pharmaceutical Research* 12(9):1250-1259.

Prestrelski, S. J. et al., (Jun. 1993). "Separation of Freezing and Drying-Induced Denaturation of Lyophilized Proteins Using Stress-Specific Stabilization," *Archives of Biochemistry and Biophysics* 303(2):465-473.

Quan, C. (Jul. 1995). *Protein Science* 4(2):p. 148, Abstract No. 490-T.

Ramanujam, R. et al., (193). "Ambient-Temperature-Stable Molecular Biology Reagents," *Biotechniques* 14(3):470-473.

Ringe, D. et al., (Sep. 2003). "The 'Glass Transition' in Protein Dynamics: What it is, Why it Occurs, and How to Exploit It," *Biophys. Chem.* 105(2-3):667-680, Abstract only, at http://www.ncbi.nlm.nih.gov, visited on Nov. 19, 2004.

Roser et al. (May 15, 1993) "A Sweeter Way To Fresher Food" *New Scientist* pp. 25-28.

Roser, B. (Jul. 1991) "Trehalose, A New Approach To Premium Dried Foods," *Trends in Food Sci. and Tech.* pp. 166-169.

Roser, B. (1991) "Trehalose Drying: A Novel Replacement For Freeze Drying" *Biopharm* 4:47-53.

Sakurai, Y. (ed) (1986) "Sogo Shokuhin Jiten" *Comprehensive Food Dictionary*, Sixth Edition, published by Dobun Shoin, Tokyo, Japan, pp. 203-204 (Dried Eggs), 208 (Dried Eggs, or Dehydrated Eggs), and 572 (Protein Denaturation), English transition provided pp. 1-9.

Saleki-Gerhardt, A. et al., (1994). "Non-Isothermal and Isothermal Crystallization of Sucrose From the Amorphous State," *Pharmaceutical Research* 11(8):1166-1173.

Saleki-Gerhardt, A. et al., (Mar. 1995). "Hydration and Dehydration of Crystalline and Amorphous Forms of Raffinose," *Journal of Pharmaceutical Sciences*, 84(3):318-323.

Sanchez, J. et al., (1989) "Recombinant System For Overexpression Of Cholera Toxin B Subunit in Vibrio Cholerae As A Basis For Vaccine Development" *Proc. Natl. Acad. Sci. USA* 86:481-485.

Schebor, C. et al., (1999). "Color Formation Due to Non-Enzymatic Browning in Amorphous, Glassy, Anhydrous, Model Systems," *Food Chemistry* 65:427-432.
Sebhatu, T. et al., (1994). "Assessment of the Degree of Disorder in Crystalline Solids by Isothermal Microcalorimetry," *International Journal of Pharmaceutics* 104:135-144.
Sellers, S. P. et al., (Jun. 2001). "Dry Powders of Stable Protein Formulations From Aqueous Solutions Prepared Using Supercritical $CO_2$-Assisted Aerosolization," *Journal of Pharmaceutical Sciences* 90(6):785-797.
Serajuddin, A. T. M. et al., (1986). "Effect of Thermal History on the Glassy State of Indapamide," *J. Pharm. Pharmacol.* 38:219-220.
Shalaev, E. Y. et al., (Nov. 1996). "How Does Residual Water Affect The Solid-State Degradation of Drugs in the Amorphous State," *Journal of Pharmaceutical Sciences*, 85(11):1137-1141.
Sharma, V. K. et al., (2004). "Effect of Vaccum Drying on Protein-Mannitol Interactions: The Physical State of Mannitol and Protein Structure in the Dried State," *AAPS PharmSciTech* 5(1) Article 10, pp. 1-12, at http://www.aapspharmscitech.org.
Skrabanja et al. (1994) "Lyophilization of Biotechnology Products" *PDA J. Pharm. Sci. Technol.* 48(6):311-317.
Sonner, C. et al., (Oct. 2002). "Spray-Freeze-Drying for Protein Powder Preparation: Particle Characterization and a Case Study With Trypsinogen Stability," *Journal of Pharmaceutical Sciences* 91(10):2122-2139.
Spi Polyols™ (2003). What are Polyols? What do Polyols do? What are Polyols' functionality? at http://www.spipolyols.com/whatarepolyols.html, visited on Jun. 25, 2004, one page.
Strickley, R. G. et al., (Jun. 1997). "Solid-State Stability of Human Insulin II. Effect of Water on Reactive Intermediate Partitioning in Lyophiles from pH 2-5 Solutions: Stabilization Against Covalent Dimer Formation," *Journal of Pharmaceutical Sciences* 86(6):645-653.
Strom, A. R. and Kaasen, I. (1993). "Trehalose Metabolism in *Escherichia coli*: Stress Protection and Stress Regulation of Gene Expression," *Molecular Microbiology* 8(2):205-210.
Stubberud, L. et al., (1998). "The Use of Gravimetry For The Study of the Effect of Additives on The Moisture-Induced Recrystallisation of Amorphous State," *International Journal of Pharmaceutics* 163:145-156.
Sussich, F. et al., (2001). "Reversible Dehydration of Trehalose and Anhydrobiosis: From Solution State to an Exotic Crystal?" *Carbohydrate Research* 334:165-176.
Takahashi et al., (1990) "Induction of $CD8^+$ cytotoxic T cells by immunization with purified HIV-1 envelope protein in ISCOMs" *Nature* 344:873-875.
Tarelli, E. et al., (1987). "Additives to Biological Substances. III. The Moisture Content and Moisture Uptake of Commonly Used Carrier Agents Undergoing Processing Conditions Similar to Those Used in the Preparation of International Biological Standards," *Journal of Biological Standardization* 15:331-340.
Timko et al. (1984) "Thermal Analysis Studies of Glass Dispersion Systems" *Drug Devel. Ind. Pharm.* 10:425-451.
Timsina, T. et al., (1994). "Drug Delivery to the Respiratory Tract Using Dry Powder Inhalers," *International Journal of Pharmaceutics* 101:1-13.
Toyama, A. (ed), (1986) *Handbook of Natural Product for food processing*, 9th Edition, Osaka, Japan, Shokuhin to Kagaku Sha, pp. 384 and 495 (ISBN4-87994-048-8).
Uritani, M. et al., (1995). "Protective Effect of Disaccharides on Restriction Endonucleases During Drying Under Vacuum," *J. Biochem.* 117:774-779.
Vain et al., (1993) "Development of the particle inflow gun" *Plant Cell, Tissue and Organ Culture* 33:237-246.
Vavelyuk, O.L. et al., (19990. "Thermostability of DNA and Its Association With Vitrification," *Tsitologiya* 41(11):958-965.
Vidgrén, M. T. et al., (1987). "Comparison of Physical and Inhalation Properties of Spray-Dried and Mechanically Micronized Disodium Cromoglycate," *International Journal of Pharmaceutics* 35:139-144.
Vromans, H. et al., (1987). "Studies on Tableting Properties of Lactose. VII. The Effect of Variations in Primary Particle Size and Percentage of Amorphous Lactose in Spray Dried Lactose Products," *International Journal of Pharmaceutics* 35:29-37.
Wang, et al. eds. (1993). *Stability and characterization of protein and peptide drugs*, Table of contents, 6 pages.
Welsh, D. T. (Aug. 1992). "The Role of Compatible Solutes In the Adaptation and Survival of *Escherichia coli*," Ph.D. Thesis Submitted to Department of Biological Sciences, University of Dundee. pp. 1-262.
Xi, Y. G. et al., (1992). "Amphotericin B Treatment Dissociates in Vivo Replication of the Scrapie Agent From PrP Acummulation," *Nature* 356:598-601.

Yoshida, H. et al., (May 1979). "Absorption of Insulin Delivered to Rabbit Trachea Using Aerosol Dosage Form," *Journal of Pharmaceutical Sciences* 68(5):670-671.

Yoshinari, T. et al., (2002). "Moisture Induced Polymorphic Transition of Mannitol and Its Morphological Transformation," *International Journal of Pharmaceutics*, 247:69-77.

Yoshioka, M. et al., (Dec. 1994). "Crystallisation of Indomethacin From the Amorphous State Below and Above Its Glass Transition Membrane," *Journal of Pharmaceutical Sciences* 83(12):1700-1705.

Nektar's U.S. Appl. No. 08/207,472, filed Mar. 7, 1994, abandoned.

Merriam Webster's Collegiate Dictionary, 346, 1119, (10th ed. 1994).

Susan Budavari et al., The Merck Index, ONR-57 (12th ed. 1996).

Nektar's U.S. Appl. No. 08/246,034, filed May 18, 1994.

Nektar U.S. Appl. No. 08/044,358, "Compositions and Methods For Nucleic Acid Delivery To The Lung" filed by Patton et al. on Apr. 7, 1993, assigned to Inhale Therapeutic Systems.

Pikal, M. J. (Oct. 1990). "Freeze-Drying of Proteins Part II: Formulation Selection," *Biopharm* 3(8):26-30.

Franks, F. (1990). "Freeze Drying: From Empiricism to Predicatability," *Cryo-Letters* 11:93-110.

Franks, F. (Oct. 1991). "Materials Science and the Production of Shelf-Stable Biologicals," *Pharmaceutical Technological International* 24:24-34.

Roser, R. *Trehalose Drying: A Novel Replacement for Freeze-Drying* 4(7) Biopharm 47-53 (Sep. 1991).

Labrude, P. et al., (1989). "Protective Effect of Sucrose on Spray Drying of Ocxyhemoglobin," *Journal of Pharmaceutical Sciences*, 78(3):223-229.

Broadhead, J. et al., *The Spray Drying of Pharmaceuticals*, 18 Drug Development and Industrial Pharmacy 1169-1206 (1992).

Whittier, E. *Lactose and its Utilization: A Review*, 27(7) J. Dairy Sci. 505-537 (Jul. 1944).

Makower, B. & W. Dye, (Jan. 1956) "Equilibrium Moisture Content and Crystallization of Amorphous Sucrose and Glucose," *Agric. and Food Chem.* 4(1):72-77.

Bell, J. H. et al., *Dry Powder Aerosols I: A New Powder Inhalation Device*, 60(10) J. Pharm. Sci. 1559-1564 (Oct. 1971).

Hickey, A. J. (1992). "Methods of Aerosol Particle Size Characterization," Chapter 8,Hicke y, ed. *Pharmaceutical Inhalation Aerosol Technology*, pp. 219-253.

Nektar's U.S. Appl. No. 10/245,722, filed Sep. 18, 2002.

*Quadrant Drug Delivery Ltd. v. Nektar Therapeutics Interference No. 105,219*, Paper No. 1 in Patent Interference No. 105,219 mailed Jun. 9, 2004, Notice Declaring Interference.

Bandara, G. et al., (Nov. 1993) "Interarticular Expression of Biologically Active Interleukin 1-Receptor-Antagonist Protein by Ex Vivo Gene Transfer," *Proc. Natl. Acad. Sci.* 90:10764-10768.

Wolff, J. A. et al., (Nov. 1989) "Grafting Fibroblasts Genetically Modified to Produce L-Dopa in a Rat Model of Parkinson Disease," *Proc. Natl. Acad. Sci.* 86:9011-9014.

During, M.J. et al., (Nov. 1994) "Long-Term Behavioral Recovery in Parkinsonian Rats by an HSV Vector Expressing Tyrosine Hydroxylase," *Science* 266(5189):856-857.

Nabel, G. J. et al., (Dec. 1993) "Direct Gene Transfer With DNA-Liposome Complexes in Melanoma," *Proc. Natl. Acad. Sci.* 90:11307-11311.

Nabel, G. J. et al., "Immunotherapy of Malignancy by In Vivo Gene Transfer Into Tumors," *Hum. Gene. Ther*. 3(4):399-410 (Aug. 1992).

Stribling, R. et al. (Dec. 1992) "Aerosol Gene Delivery in Vivo," *Proc. Natl. Acad. Sci.* 89:11277-11281.

Colaco, C. et al., (Sep. 1992) "Extraordinary Stability of Enzymes Dried in Trehalose: Simplified Molecular Biology" *Bio/Technology* 10(9):1007-1011.

Roser et al. U.S. Appl. No. 09/945,180 filed Aug. 31, 2001, (now Patent No. 6,565,871) non final Office Action dated Jul. 24, 2002.

Roser et al., U.S. Appl. No. 09/945,180 filed Aug. 31, 2001, (now Patent No. 6,545,871) Amendment Under 37 CFR §1.111 dated Nov. 25, 2002.

Roser U.S. Appl. No. 08/349,029, Specification, as filed Dec. 2, 1994 (Patent No. 6,290,991).

Roser U.S. Appl. No. 08/349,029, Office Action dated May 15, 1995 (Patent No. 6,290,991).

Masters, K. Spray Drying Handbook, England; Longman Scientific & Technical, 5$^{th}$ ed., Chapters 13 and 15. (1991).

Allen, D. J. et al., Determination of the Degree of Crystallinity in Solid-Solid Equilibria, *J. Pharm. Sci.* 58:1190-1193 (1969).

Gold, V. et al., (1987). *International Union of Pure and Applied Chemistry (IUPAC) Compendium of Chemical Terminology*, 1$^{st}$ edition, Blackwell Scientific Publications, V. Gold et al., "Definition of Solid Solution And Mixed Crystal", p. 258 and p. 385.

Pekarek et al. (1994) "Double-walled polymer microspheres for controlled drug release" *Nature* 367:258-260.

New Shorter Oxford English Dictionary on Historical Principles, 1993, p. 68, definition of *amorphous*.

Roser U.S. Appl. No. 08/349,029, Notice of Allowability dated Nov. 9, 1998 (Patent No. 6,290,991).

Roser U.S. Appl. No. 08/349,029, Petition for Withdrawal from Issue Pursuant to 37 C.F.R. § 1.313 (Patent No. 6,290,991).

Dalby, R. N. et al. (1992). "Droplets Drying and Electrostatic Collection a Novel Alternative to Conventional Comminution Techniques," *Journal of Biopharmaceutical Sciences* 3(½):091-099.

Remington's Pharmaceutical Sciences, 18th edition., Alphonso R. Gennaro (Ed), Mack Publishing Company, "Chapter 88: Powders", pp. 1615-1632 (1990).

Merriam Webster's Collegiate Dictionary, 10th ed. 568, 717 (1994).

Dorland's Illustrated Medical Dictionary, 26th ed., p. 666 (1985).

Sambrook, et al., Molecular Cloning: A Laboratory Manual, 2nd. ed., pp. E.10-E.17 (1989).

Nektar U.S. Appl. No. 10/245,722, Preliminary Amendment, Paper No. 4, mailed Sep. 18, 2002 from the prosecution history of U.S. Appl. No. 10/245,722, Pub. No. US 2003/0092666 ("the '722 Application"), filed Sep. 18, 2002, (the Application-in-Interference).

Merriam Webster's Third International Dictionary, 433 (1993).

Monnier et al., Mechanisms of Protection Against Damage Mediated by the Maillard Reaction in Aging Gerontology 37:152-165 (1991).

Dorland's Illustrated Medical Dictionary, 28th ed., pp. 36, 507, 1272, 1330 (1994).

Roser U.S. Appl. No: 08/349,029, Paper No. 24, Amendment dated Nov. 19, 1997 (Patent No. 6,290,991).

Roser U.S. Appl. No. 08/349,029, Paper No. 26, Office Action dated Feb. 10, 1998 (Patent No. 6,290,991).

Roser U.S. Appl. No. 08/349,029, Paper No. 28, Amendment under 37 CFR § 1.111 dated Aug. 14, 1998 (Patent No. 6,290,991).

Roser U.S. Appl. No. 08/349,029, Paper No. 36, Preliminary Amendment dated Aug. 17, 1999 (Patent No. 6,290,991).

Roser U.S. Appl. No. 08/349,029, Paper No. 4, Office Action dated May 15, 1995 (Patent No. 6,290,991).

Merriam Webster's Collegiate Dictionary, 10th ed., 335 (1994).

Belopol'skaya, T. V. et al., *The Effect of Water as Natural Plasticizer on Thermal Properties of Denaturated DNA Studied by Calorimetry* 4 Vestnik Sankt-Petersburgkogo Universiteta Seriya 16-22 (1999).

Buitink, Julia et al., *High Critical Temperature above Tg May Contribute to the Stability of Biological Systems* 79 Biophysical Journal 1119-1128 (Aug. 2000).

Byron, Peter R. et al., *Drug Carrier Selection—Important Physicochemical Characteristics* Respiratory Drug Delivery, 5th Edition, Interpharm Press, 103-113 (1996).

Casselyn, M. et al., *Time-Resolved Scattering Investigations of Brome Mosaic Virus Microcrystals Appearance* D58 Acta Cryst. 1568-1570 (2002).

Chan, Hak-Kim et al., *Physical Stability of Salmon Calcitonin Spray-Dried Powders for Inhalation* 93(3) Journal of Pharmaceutical Sciences 792-804 (Mar. 2004).

Costantino, H. R. et al., (Nov. 1998). "Effect of Mannitol Crystallization on the Stability and Aerosol Performance of a Spray-Dried Pharmaceutical Protein, Recombinant Humanized Anti-IgE Monoclonal Antibody," *Journal of Pharmaceutical Sciences* 87(11):1406-1411.

Crommelin, Daan, J. A. & Schreier, H. *Liposomes* J. Kreuter ed., Colloidal Drug Delivery Systems, Marcel Dekker, 73-190 (1994).

D'Cruz, N. *Relationship Between Protein Thermal Stability and Glass Transition in Gelatin-Polyol and Gelatin-Water Mixtures* Proceedings of 2004 Meeting IFT, Jul. 12-16, 2004, Las Vegas, NV, Session 17E, Food Chemistry: Proteins, at http://ift.confex.com/ift/2004/techprogram/paper_23006.htm, 17-EA (2004).

Dorland's Illustrated Medical Dictionary, 28th Edition, W. B. Saunders Company, p. 1330, Definition of Polyol (1994).
Gupta, A. et al., (Mar. 15, 2004). "Single Virus Particle Mass Detection Using Microresonators With Nanoscale Thickness," *Applied Physics Letters* 84(11):1976-1978.
Hancock, B. C. et al., (1994). "The Relationship Between the Glass Transition Temperature and the Water Content of Amorphous Pharmaceutical Solids," *Pharmaceutical Research* 11(4):471-477.
Heller, Martin C. et al., *Protein Formulation and Lyophilization Cycle Design: Prevention of Damage Due to Freeze-Concentration Induced Phase Separation* 63 Biotechnology & Bioengineering 166-174 (1999).
Hoener, Betty-Ann et al., (1996). "Factors Influencing Drug Absorption and Availability," Gilbert S. Banker et al. eds., *Modern Pharmaceutics*, Marcel Dekker Inc., Chapter 4, pp. 121-153.
Slade, Louise & Levine, Harry, *The Glassy State Phenomenon in Food Molecules* J. M. V. Blanshard and P. J. Lillford eds., The Glassy State in Foods, Nottingham University Press, 35-101.(1993).
Liu, Jinsong et al., (Aug. 2002). "Dynamics of Pharmaceutical Amorphous Solids: The Study of Enthalpy Relaxation by Isothermal Microcalorimetry," *Journal of Pharmaceutical Sciences* 91(8):1853-1862.
MacKenzie, A.P. (1975) *Collapse During Freeze Drying—Qualitative and Quantitative Aspects* Freeze Drying and Advanced Food Technology, Academic Press, London, Chapter 19, pp. 277-307.
Masters, K. Spray Drying Handbook, England; Longman Scientific & Technical, $5^{th}$ ed., pp. 640-642(1991).
Mattern, Markus et al., *Formulation of Proteins in Vacuum—Dried Glasses. II. Process and Storage Stability in Sugar-Free Amino Acid Systems* 4(2) Pharmaceutical Development & Technology 199-208 (1999).
New Shorter Oxford English Dictionary on History Principles, Lesley Brown ed., Clarendon Press Oxford, p. 3592, Definition of "Vitreous" (1993).
Roempp's Encyclopedia of Chemistry, Definition of Polyol, 9th Expanded and Revised Edition, 3558-3559, with certified English Translation.
Roos, Yrjö & Karel, Marcus, *Phase Transitions of Mixtures of Amorphous Polysaccharides And Sugars* 7(1) Biotechnology Progress 49-53 (Jan./Feb. 1991).
Slade, Louise & Levine, Harry, *Non-Equilibrium Behavior of Small Carbohydrate-Water Systems* 60(12) Pure and Applied Chemistry 1841-1864 (1988).
Sokolov, A. P. et al., *Glassy Dynamics in DNA: Ruled by Water of Hydration* 110(14) Journal of Chemical Physics 7053-7057 (Apr. 8, 1999).
Stedman'S Medical Dictionary, William & Wilkins, 26th ed., p. 1405, Definition of Polyol (1995).
Ulrich, Anne A. *Biophysical Aspects of Using Liposomes as Delivery Vehicles* 22(2) DNA-Lipid Structures 129-150 (Apr. 2002).
Natarajan, Padmaja (Jan. 3, 2002), *Crystallization Conditions for VIPER Entries* at http://www.xtal.tsinghua.edu.cn/research/group5/web/material/Virus%20Crystallization%20Page.htm visited on Nov. 4, 2004, 5 pages (last updated Jan. 3, 2002).
Thatcher, E. (Jan. 5, 2002), *Quantitation of Virus* at http://www.sonoma.edu/users/t/thatcher/biol383/lab.htm visited on Nov. 1, 2004, 4 pages (last updated Jan. 5, 2002).
Nektar U.S. Appl. No. 08/422,563, filed Apr. 14, 1995, Paper No. 8, Amendment, mailed Dec. 10, 1996 (Patent No. 5,994,314).
Nektar U.S. Appl. No. 08/422,563, filed Apr. 14, 1995, Paper No. 16, Response under 37 C.R.F. § 1.129, mailed Feb. 5, 1998 (Patent No. 5,994,314).
Nektar U.S. Appl. No. 08/422,563, filed Apr. 14, 1995, Paper No. 17, Office Communication mailed Apr. 3, 1998 (Patent No. 5,994,314).
Nektar Therapeutics' Request for Interference Pursuant to 37 C.F.R. § 1.607, mailed Jan. 8, 2004, from the prosecution history of Nektar U.S. Appl. No. 10/245,722, filed Sep. 18, 2002 (published as U.S. Publication No. 2003/0092666).
Lehninger, Albert L. *The Molecular Basis of Cell Structure and Function* Biochemistry, Chapter 31, 859-890 (Worth Publishers Inc., 2nd edition, 1975).

Dean Allison, S. & Anchordoquy, Thomas J., *Lyophilization of Nonviral Gene Delivery Systems*, 65 Methods in Molecular Medicine, Nonviral Vectors for Gene Therapy, Ch. 18, 225-252 (Mark A. Findeis ed., Humana Press, 2001).
Anchordoquy, Thomas J. et al., *Physical Stabilization of DNA Based Therapeutics*, 6(9) DDT 463-470 (May 2001).
Martin, A. et al., *States of Matter and Phase Equilibria* Physical Pharmacy, Physical Chemical Principles in the Pharmaceutical Sciences, 3rd. ed., Chapter 4, 62-91 (1983).
York, Peter, *Powdered Raw Materials: Characterizing Batch Uniformity* Respiratory Drug Delivery IV 83-91 (1994).
Byström, Katarina & Briggner, Lars-Erik, *Microcalorimetry—A Novel Technique for Characterization of Powders*, Respiratory Drug Delivery IV 297-302 (1994).
Ahlneck, Claes and Zografi, George, *The Molecular Basis of Moisture Effects on the Physical and Chemical Stability of Drugs in the Solid State*, 62 Int's J. Pharm. 87-95 (1990).
Nektar U.S. Appl. No. 08/417,507 filed Apr. 4, 1995, with the File Wrapper Continuation's Request.
Nektar U.S. Appl. No. 08/422,563 filed Apr. 14, 1995.
Roser U.S. Appl. No. 08/349,029 filed Dec. 2, 1994, Paper No. 9, Amendment under 37 C.F.R. § 1.111, mailed on Nov. 15, 1995, (Patent No. 6,290,991).
Chan, Hak-Kim and Gonda, Igor, *Solid State Characterization of Spray-Dried Powders of Recombinant Human Deoxyribonuclease (RhDNase)* 87(5) Journal of Pharmaceutical Sciences, 647-65 (May 1998).
Dose, K. et al. *Survival in Extreme Dryness and DNA-Single-Strand Breaks* 12(4) Advances in Space Research (4)221-(4)229 (1992).
Roser U.S. Appl. No. 08/349,029, filed Dec. 2, 1994, Paper No. 40, Amendment under 37 C.F.R. § 1.111, mailed on Dec. 29, 1999 (Patent No. 6,290,991).
Craig, I. D. et al., (2001). "Maillard Reaction Kinetics in Model Preservation Systems in the Vicinity of the Glass Transition: Experiment and Theory," *J. Agric. Food Chem.* 49(10):4706-4711.
Carpenter, John F. et al., *Rational Design of Stable Lyophilized Protein Formulations: Some Practical Advice*, 14:8 Pharmaceutical Res. 969-975 (1997).
Underwood, Stephen L. et al., *A Novel Technique for the Administration of Bronchodilator Drugs Formulated as Dry Powders to the Anaesthetized Guinea Pig*, 26 J. Pharm. Methods 203-210(1991).
Stribling, Roscoe et al., *The Mouse as a Model for Cationic Liposome-Based Aerosolized Gene Delivery*, 3(½) J. Biopharm. Sci. 255-263 (1992).
Nektar U.S. Appl. No. 08/044,358 filed Apr. 7, 1993, Paper No. 5, Amendment dated Feb. 23, 1994 (Abandoned).
Crowe, Lois M. et al. (Oct. 1996). "Is Trehalose Special for Preserving Dry Biomaterials?" *Biophysical Journal* 71:2087-2093.
Crowe, John H. et al., (1998). "The Role of Vitrification in Anhydrobiosis," Annu. Rev. Physiol. 60:73-103.
Singer, Mike A. & Lindquist, Susan (Nov. 1998) "Thermotolerance in *Saccharomyces cerevisiae*: the Yin and Yang of Trahalose," TIBTECH 16:460-468.
Sola-Penna, Mauro et al., *Stabilization Against Thermal Inactivation Promoted by Sugars on Enzyme Structure and Function: Why Is Trehalose More Effective Than Other Sugars?* 360(1) Archives of Biochemistry and Biophysics 10-14, Article No. BB980906, (Dec. 1998).
De Carlo, S. et al., *Unexpected Property of Trehalose as Observed by Cryo-Electron Microscopy* 196(1) Journal of Microscopy 40-45 (Oct. 1999).
Branca, C. et al., *Destructuring effect of trehalose on the tetrahedral network of water: a Raman and neutron diffraction comparison*, 304 Physica A 314-318(2002).
Zubay, G. Biochemistry, Second Edition, p. 169, Table 5-6 Major Steroid Hormones (1988).
The Merck Index, under Section entitled "Organism Name Reactions," p. ONR-57, at "Maillard Reaction" (10th ed. 1983).
Zubay, G. Biochemistry, Second Edition, pp. 216-232 "Structural Properties of DNA" (1988).
Albert, B. et al., Molecular Biology of the Cell, 2nd ed., Garland Publishing, Inc., Ch. 2, p. 58, (1989).

Murphy, Brian R. and Chanock, Robert M. Fields Virology, vol. 1, Chapter 16 entitled *Immunization Against Virus Disease*, 467, at p. 468, first full paragraph, first column, lines 26-33 (Bernard N. Fields et al. eds., Lippincott-Raven Publishers, 3rd ed. 1996).

D'Hondt, Eric *Possible Approches to Develop Vaccines Against Hepatitis A*, 10(Suppl. 1) Vaccine, S48, Abstract, lines 6-9 (1992).

Sarkar, Nurul H. and Moore, Dan H. *Immunization of Mice Against Murine Mammary Tumor Virus Infection and Mammary Tumor Development*, 38, Cancer Research, 1468, Abstract, lines 12-15 (May 1978).

McGraw-Hill Encyclopedia of Science & Technology, 6th ed., vol. Nos. 7, 12, 14, pp. 637, 395, and 405 (1987).

Zubay, G. Biochemistry, 2nd ed., pp. 39, 169 (1988).

Merriam Webster's Collegiate Dictionary, Merriam-Webster, Incorporated, Springfield, Massachusetts, USA, $10^{th}$ edition, p. 334 (2002).

Remington: The Science and Practice of Pharmacy, A. R. Gennaro, $19^{th}$ edition, Mack Publishing Company, Easton, Pennsylvania 18042, pp. 1517-1518 (1995).

Allison, S. D. and Thomas J. Anchodorquy, *Mechanisms of Protection of Cationic Lipid-DNA Complexes During Lyophilization*, Journal of Pharmaceutical Sciences, 89(5):682-691 (May 2000).

Brochure on Ready-to-Go™ Molecular Biology Reagents: "PurePrep™ *Macro* Plasmid Purification Kit," "Overview: Ready-to-Go™ Technology," and "Ready-to-Go™ Lambda Packaging Kit," by Pharmacia Biotech, *Analects for Molecular and Cell Biology* 22(2):1-7 (Spring 1994).

*Theory*, Sec. 14.1 entitled "Psychrometric Chart (10-20° C based on Barometric Pressure of 101.325 kPa,") p. 283.

Ablett, S., et al., (1992). "Differential Scanning Calorimetric Study Of Frozen Sucrose And Glycerol Solutions" *J. Chem. Soc. Faraday Trans.* 88(6):789-794.

Adler, M. et al., (Feb. 1999). "Stability and Surface Activity of Lactate Dehydrogenase in Spray-Dried Trehalose," *Journal of Pharmaceutical Sciences*, 88(2):199-208.

Adler, M. et al., (2000). "Surface Composition of Spray-Dried Particles of Bovine Serum Albumin/Trehalose/Surfactant," *Pharmaceutical Research* 17(7):863-870.

Adjei, A. et al. (1994). "Pulmonary Delivery of Therapeutic Peptides and Proteins," *J. Controlled Release* 29:361-373.

Akers, M.J., et al., (Aug. 1994) "Top 10 current technical issues in parenteral science" *Pharm. Tech.* 18(8):26, 28, 30-33, 36.

Aldrich, J. E. et al. (1974). "Use of the Spinning Disk Technique to Produce Monodisperse Microspheres of Human Serum Albumin for Labeling With Readioisotopes," *The International Journal of Applied Radiation and Isotopes* 25:15-18.

Allison, D. et al., (1999). "[Abstract] Preservation of Lipid/DNA Complexes During Acute Lyophilization Stress by Excipients in the Crystalline, Amorphous, and Rubber Phases,"*1999 AAPS Annual Meeting*, at http://www.aapspharmsci.org/abstracts/AM_1999/2095.htm, visited on Nov. 16, 2004, one page.

Allison, S. D. et al. (2000). "Stabilization of Lipid/DNA Complexes During The Freezing Step Of The Lyophilization Process: The Particle Isolation Hypothesis," *Biochimica et Biophysica Acta* 1468:127-138.

Anchordoquy T. et al. (1998). "Cryopreservation of Sperm from the Marine Shrimp *Sicyonia ingentis,*" *Cryobiology* 25:238-243.

Anchordoquy, T. J. et al. (1998). "[Abstract] Stabilization of Lipid/DNA Complexes During Acute Lyophilization and Rehydration Stress: A Comparison of Different Excipients," *1998 AAPS Annual Meeting*, at http://www.aapspharmsci.org/abstracts/AM_1998/2520.html, visited on Nov. 16, 2004, one page.

Anchordoquy, T. J. et al. (Sep. 1998). "Stability of Lipid/DNA Complexes during Agitation and Freeze-Thawing,"*Journal of Pharmaceutical Sciences* 87(9):1046-1051.

Anchordoquy, T.J. et al. (Mar. 2000). "Physical Stability of Nonviral Plasmid-Based Therapeutics,"*Journal of Pharmaceutical Sciences* 89(3):289-296.

Anchordoquy, T. J. (2001). "Physical Stabilization of DNA-Based Therapeutics During Freezing and Drying," *American Pharmaceutical Review* 4(4):34-41.

Anchordoquy, T. J. et al. (May 2001). "Physical Stabilization of DNA-Based Therapeutics," *Drug Discovery Today* 6(9):463-470.

Anchordoquy, T.J. (2004). "Lyophilization and Storage Stability of Colloidal Gene Delivery Systems," Presentation given at conference regarding Freeze-Drying of Pharmaceuticals and Biologicals, Jul. 28-31, 2004, at http://www.ipph.purdue.edu/~nsf/freeze/presentations2004.html, visited on Nov. 10, 2004, 3 pages and PowerPoint® presentation of 32 pages, total of 35 pages.

Andrews, A. T. (Aug. 1991). "Partial Denaturation and Renaturation of β-Lactoglobulin at Air-water Interfaces," *Biochem Soc. Trans* 19(3):272 S (one page).

Angell, C. A. (Mar. 21, 1995). "Formation of Glasses From Liquids and Biopolymers," *Science* 267:1924-1935.

Arakawa, T. et al., (1991). "Protein-Solvent Interactions in Pharmaceutical Formulations," *Pharmaceutical Res.* 8(3):285-291.

Beaucage, S. L. et al. (1981). "Deoxynucleoside Phosphoramidites—A New Class of Key Intermediates for Deoxypolynucleotide Synthesis," *Tett. Lett.* 22(20):1859-1862.

Bone, S. et al., (1985). "Dielectric Studies of Protein Hydration and Hydration-Induced Flexibility," *J. Mol. Biol.* 181:323-326.

Brown, D. (Friday, Dec. 8, 1995). "Gene Therapy 'Oversold' by Researchers, Journalists, NIH Advisers Cite Nearly Uniform Failure," *Washington Post*, A1, A22, Col. 1.

Burke, M. (1986). "Appendix D, The Glassy State and Survival of Anhydrous Biological Systems," in *Membranes, Metabolism, and Dry Organisms*, A. Carl Leopold, ed., Comstock Publishing Associates, pp. 358-363.

Carjaval, M. T. et al., (Oct. 1994). "Spray-Drying Optimization to Produce Powder for Inhalation," *Pharmaceutical Research* 11(10):S-140, Abstract No. PT6037.

Carpenter, J. et al., (1988). "Modes of Stabilization of a Protein by Organic Solute," *Cryobiology* 25:459-470.

Carpenter, J. F. et al., (1987). "Stabilization of Phosphofrucktokinase During Air-Drying with Sugars and Sugar/Transition Metal Mixtures," *Cryobiology* 24:455-464.

Carpenter, J.F., et al., (1988). "The Mechanism Of Cryoprotection Of Proteins By Solutes" *Cryobiology* 25:244-255.

Carpenter, J. F. et al. (1994). "Chapter 9: Interactions of Stabilizers With Protein During Freezing and Drying," *ACS Symposium Series 567, Formulation and Delivery of Proteins and Peptides*, J. L. Cleland & R. Langer (eds) 134-147.

Chan, H.-K. et al. (1997). "Spray Dried Powders and Powder Blends of Recombinant Human Deoxyribonuclease (rhDNase) for Aerosol Delivery," *Pharmaceutical Research* 14(4):431-437.

Charm, S. E. et al., (Nov. 1970). "Enzyme Inactivation With Shearing," *Biotechnol. Bioeng.* 12:1103-1109.

Chiou, W. L. et al., (Sep. 1971). "Pharmaceutical Applications of Solid Dispersion Systems," *Journal of Pharmaceutical Sciences* 60(9):1281-1302.

Clark, A. R. et al. (1996). "The Balance Between Biochemical and Physical Stability For Inhalation Protein Powders: rhDNASE As An Example," *Respiratory Drug Delivery V*, pp. 167-174.

Clegg, J.S., (1985). "Chapter 10: The Physical Properties And Metabolic Status Of *Artemia* Cysts At Low Water Contents: The 'Water Replacement Hypothesis'" *Membranes, Metabolism and Dry Organisms*, A. C. Leopold, ed., Comstock Publishing Associates, pp. 169-187.

Colaco, C. et al., (1993). *Chemical Abstracts*, vol. 118, 1992, No. 164103, CAPLUS on STN, one page.

Colthorpe, P. et al., (1992). "The Pharmacokinetics of Pulmonary-Delivered Insulin: A Comparison of Intratracheal and Aerosol Administration to the Rabbit," *Pharmaceutical Research* 9(6):764-768.

Crowe, J.H., et al., (Apr. 1993). "Preserving Dry Biomaterials: The Water Replacement Hypothesis, Part 1" *BioPharm* 6(3):28-29, 32-33, 37.

Dinnbier, U. et al., (1988). "Transient Accumulation Of Potassium Glutamate And Its Replacement By Trehalose During Adaptation Of Growing Cells Of *Escherichia coli* K-12 To Elevated Sodium Chloride Concentrations" *Arch. Microbiol.* 150:348-357.

Elliott, R. B. et al. (1987). "Parenteral Absorption of Insulin From the Lung in Diabetic Children," *Aust. Paediatr. J.* 23:293-297.

Fäldt, P. et al. (1994). "The Surface Composition of Spray-Dried Protein-Lactose Powders," *Colloids and Surfaces A: Physiochemical and Engineering Aspects*, 90:183-190.

Farhood, H. et al., (1992). "Effect of Cationic Cholesterol Derivatives on Gene Transfer and Protein Kinase C Activity," *Biochimica et Biophysica Acta*, 1111:239-246.

Felgner, P. L. et al., (Jan. 26, 1989). "Cationic Liposome-Mediated Transfection," *Nature* 337(6205): 387-388.

Finney, J.S. et al, (1984). "Protein Hydration and Enzyme Activity: The Role of Hydration-Induced Conformation and Dynamic Changes in the Activity of Lysozyme," *Comments on Molecular and Cellular Biophysics, Part A*, 2(¾):129-151.

Finot, P.A., et al., eds., (1990). *The Maillard Reaction in Food Processing, Human Nutrition and Physiology*, Birkhäuser Verlag, Basel, title page and table of contents are included herewith, pp. 1-6.

Flink, J. M. (1983). "Chapter 17: Structure and Structure Transitions in Dried Carbohydrate Materials," in *Physical Properties of Foods*, M. Peleg and E.B. Bogley (editors), Aui Publishing, pp. 473-521.

Fox, K. C. (Mar. 31, 1995). "Putting Proteins Under Glass," *Science* 267:1922-1923.

Franks, F., et al., (Oct. 1991). "Materials Science And The Production of Shelf-Stable Biologicals," *BioPharm* 4(9):38-55.

Franks, F. et al. (1992). "Nucleation and Crystallization in Aqueous Systems During Drying: Theory and Practice," *Pure & Appl. Chem.* 64(11):1667-1672.

Franks, F., et al., (1993). "Stable Enzymes by Water Removal" in *Stability and Stabilization of Enzymes*, Proceedings of an International Symposium Held in Maastricht, The Netherlands, Nov. 22-25, 1992, van den Tweel, W.J.J., et al., eds., Elsevier, Amsterdam, pp. 45-54.

Franks, F. (1993). "Solid Aqueous Solutions," *Pure & Appl. Chem.* 65(12):2527-2537.

Franks, F., (Mar. 1994). "Long-Term Stabilization Of Biologicals" *Bio/Tech*. 12:253-256.

French, D. L. et al., (1995). "Moisture Induced State Changes in Spray-Dried Trehalose/Protein Formulation," *Pharmaceutical Res.* 12(9 Suppl.):S83, Abstract No. BIOTEC 2019.

French, D. L. et al., (1995). "FTIR Investigation of Hydration-Induced Conformational Changes in Spray-Dried Protein, Trehalose Powders," *Pharmaceutical Res.* 12(9 Suppl.):S83, Abstract No. BIOTEC 2020.

Friedmann, T. (Jun. 16, 1989). "Progress Toward Human Gene Therapy," *Science* 244(4910):1275-1281.

Giæver, H. M. et al., (Jun. 1988). "Biochemical And Genetic Characterization Of Osmoregulatory Trehalose Synthesis In *Escherichia coli*" *J. Bacteriol*. 170(6):2841-2849.

Gänsslen, M. (1925). "On the Inhalation of Insulin," English translation including the original article "Uber Inhalation von Insulin" *Klin. Wochenschr*. 4:71 and attached article by Heubner et al., (1924). "Kurze Wissenschaftliche Mitteilungen," *Klin. Wochenschrift* 51:2342-2343.

Gershon, H. et al., (1993). "Mode of Formation and Structural Features of DNA-Cationic Liposome Complexes Used for Transfection," *Biochemistry* 32:7143-7151.

Gibbs, J. H. et al., (Mar. 1958). "Nature of the Glass Transition and the Glassy State," *The Journal of Chemical Physics* 28(3):373-383.

Gilardi, P. et al., (Jul. 1990). "Expression of Human α-Antitrypsin Using a Recombinant Adenovirus Vector," *FEBS* 267(1):60-62.

Gorman, C. M. et al., (Nov. 1982). "The Rous Sarcoma Virus Long Terminal Repeat is a Strong Promoter When Introduced into a Variety of Eukaryotic Cells by DNA-Mediated Transfection," *Proc. Natl. Acad. Sci. USA* 79:6777-6781.

Govinda Rao, A. R. (1959). "Aerosol Insulin Inhalation Enquiry," *Indian J. Physiol. Pharmacol*. 3:161-167.

Graham, D. T. et al., (1984). "An In-Vitro Test for the Duration of Insulin Suspension," *J. Pharm. Pharmacol*. 36:427-430.

Habener, J. F. et al., (1971). "Parathyroid Hormone: Secretion and Metabolism In Vivo," *Proc. Natl. Acad. Sci. USA* 68(12):2986-2991.

Harms, H. et al., (1987). "The Pulse Amplitude and Frequency Modulation of Parathyroid Hormone Secretion in Man," *Int. Symp. On Osteoporosis, Aalborg*, Abstract 232:723-724.

Harrington, C.R., et al., (1994). "A Glycation Connection" *Nature* 370:247-248.

Hastings, R. H. et al., (1992). "Clearance of Different-Sized Proteins From the Alveolar Space in Human and Rabbits," *Journal of Applied Physiology*, 73(4):1310-1316.

Hatley, R. H. M. (1991). "The Effective Use of Differential Scanning Calorimetry in the Optimisation of Freeze-Drying Processes and Formulations," *Development Biol. Standard* 74:105-122.

Herrington, D. L. (1934). "Some Physico-Chemical Properties of Lactose," *J. Dairy Science* 17:501-518.

Hesch, R. D. et al., (1984). "First Clinical Observations with hPTH(1-38), a More Potent Human Parathyroid Hormone," *Hormone Metabol. Res*. 16(10):559-560.

Hesch, R. D. et al., (1988). "Pulsatile Secretion of Parathyroid Hormone and Its Action on a Type I and Type II PTH Receptor: A Hypothesis for Understanding Osteoporosis," *Calcif. Tissue Int.* 42:341-344.

Hodsman, A. B. et al., (May 1990). "Biochemical Responses to Sequential Human Parathyroid Hormone (1-38) and Calcitonin in Osteoporotic Patients," *Bone & Mineral* 9(2):137-152.

Hodsman et al., (Jul. 1991). "Bone Densitometric and Histomorphometric Responses to Sequential Human Parathyroid Hormone (1-38) and Salmon Calcitonin in Osteoporotic Patients," *Bone & Mineral* 14(1):67-83.

Israeli, E. et al., (1993). "Protection Of Freeze-Dried *Escherichia coli* By Trehalose Upon Exposure To Environmental Conditions," *Cryobiol*. 30:519-523.

Kaneda, Y. et al., (Jan. 20, 1989). "Increased Expression of DNA Cointroduced With Nuclear Protein in Adult Rat Liver," *Science* 243:375-378.

Karel, M. (1975). "IV—Non-Equilibrium Situations in Water Sorption," and "V—Depression of Water Activity by Solutes," under Section 34 entitled "Physico-Chemical Modification of the State of Water in foods—A Speculative Survey," in *Proceedings of an International Symposium on Water Relations of Foods held in Glasgow in Sep. 1974*, edited by R. B. Duckworth, Academic Press, pp. 648-651.

Kauzmann, W. (1948). "The Nature of the Glassy State and the Behavior of Liquids at Low Temperatures," in *Chemical Reviews*, vol. 43, W. Albert Noyes, Jr. et al., eds., The American Chemical Society & The Williams & Wilkins Company, pp. 219-256.

Kahn, R. et al., (1992). "Optimization of Retroviral Vector-Mediated Gene Transfer Into Endothelial Cells in Vitro," *Circulation Research* 71(6):1508-1517.

Khan, R. et al. (1993) "Enzymic Regioselective Hydrolysis Of Peracetylated Reducing Disaccharides, Specifically At The Anomeric Centre: Intermediates For The Synthesis Of Oligosaccharides," *Tetra. Letts* 34(48):7767-7770.

Köhler, D (1987). "Nicht Radioaktives Verfahren Zur Messung der Lungenpermeabilität: Inhalation von Insulin," *Atemw Lungenkrkh* 13:230-232, with English abstract.

Köhler, D. (1990). "Aerosols for Systemic Treatment," *Lung*. (Suppl.):677-684.

Köhler, D. (1993). "Systemic Therapy With Aerosol," in *Aerosols in Medicine, Principles, Diagnosis, and Therapy*, $2^{nd}$ revised edition, edited by F. Morén et al., Elsevier Science Publishers B.V., pp. 303.

Larsen, P. I. et al., (1987). "Osmoregulation In *Escherichia coli* By Accumulation Of Organic Osmolytes: Betaines, Glutamic Acid, And Trehalose," *Arch. Microbiol*. 147:1-7.

Laube, B. L.et al. (Apr. 28, 1993). "Preliminary Study of the Efficacy of Insulin Aerosols Delivered by Oral Inhalation in Diabetic Patients," *JAMA* 269(16):2106-2109.

Lechuga-Ballesteros, D. et al., (2000). "Aerosol Drug Development Of A Spray Dried Liquid Crystalline Formulation Of Cyclosporine", *Respiratory Drug Delivery VII*, Serentec Press, Inc. Raleigh, North Carolina, pp. 247-255.

Lechuga-Ballesteros, D. et al., (2002). "Residual Water In Amorphous Solids, Measurement And Effect On Stability" in *Amorphous Food and Pharmaceutical Systems*, H. Levine, (Ed.) The Royal Society of Chemistry, London, pp. 275-316.

Lechuga-Ballesteros, D. et al. (Feb. 2003). "Microcalorimetric Measurement of the Interactions between Water Vapor and Amorphous Pharmaceutical Solids", *Pharmaceutical Research*, 20(2):308-318. Chosen as a highlight of the Pharm. Res. February issue in the AAPS Newsmagazine vol. 6 No. 2.

Lechuga-Ballesteros, D. et al., (Sep. 2003). "Properties and Stability of a Liquid Crystal Form of Cyclosporine—The First Reported Naturally Occurring Peptide That Exists as a Thermotropic Liquid Crystal", *Journal of Pharmaceutical Sciences*, 92 (9):1821-1831.

Lechuga-Ballesteros, D. (2003). "Administración Sistématica de Proteínas en Polvos Inhalables," *Informaceutico*, 10(2):44, 46-47, in Spanish.

Lee, S.-W. et al. (Apr. 1976). "Development of an Aerosol Dosage Form Containing Insulin," *J. Pharmaceutical Sci*.65(4):567-572.

Lee, G. et al., (May 1985). "Rheological Properties of Non-Modified and n-Alkyl Surface-Modified Colloidal Silica Sols," *Journal of Colloid and Interface Science*, 105(1):257-266.

Lee, G. et al., (Jan. 1996). "Stabilisierung von Peptidarzneistoffen durch Gefriertrocknung," *Prisma*, 3(2):105-116.

Levine, H. et al., (1986). "A Polymer Physico-Chemical Approach to the Study of Commercial Starch Hydrolysis Products (SHPs)," *Carbohydrate Polymers* 6:213-244.

Levine, H. et al., (1988). "Chapter 9: Collapse Phenomena—A Unifying Concept For Interpreting The Behaviour of Low Moisture Foods," in *Food Structure—Its Creation and Evaluation*, J.M. Blanshard et al., (editors), pp. 149.180.

Levine, H. et al., (1988). "Principles of 'Cryostabilization' Technology from Structure/Property Relationships of Carbohydrate/Water Systems, A Review," *Cryo-Letters* 9:21-63.

Lindberg, J. (1993) "Creating the Future for Portable Inhalers," *Summary of Lecture at Management Forum* Dec. 6-7, 1993, 2 pages total.

Maa, Y.-F. et al., (1997). "The Effect of Operating and Formulation Variables on the Morphology of Spray-Dried Protein Particles," *Pharmaceutical Development and Technology* 2(3):213-223.

Meisner, D. et al. (Oct. 1994). "Evaluation of a New Breath-Actuated Dry Powder Inhaler Prototype," *Pharmaceutical Research* 11(10):S140, Abstract No. PT6038.

Michelson, J. (1976). "Chapter 22: Pilot Plant Scale-Up Techniques," in *The Theory and Practice of Industrial Pharmacy*, $2^{nd}$ edition, Lega & Febiger, pp. 626-649.

Mumenthaler, M. et al., (May 27, 1991). "Atmospheric Spray-Freeze Drying: A Suitable Alternative in Freeze-Drying Technology," *International Journal of Pharmaceutics* 72(2):97-110.

Nagai, T. (1984). "Powder Dosage Form of Insulin for Nasal Administration," *Journal of Controlled Release*, pp. 15-22, see abstract, Tables and discussion.

Nagano, M. et al., (1985). "New Method of Insulin Therapy: Transpulmonary Absorption of Insulin,"*Jikeikai Med. J.* 32:503-506.

Naini, V. et al., (1994). "Physical Characterization of Spray Dried Sugars Suitable as Carriers in Inhalation Systems," *Presented at a poster at $10^{th}$ Annual AAPS*, Miami, Florida, PT6180, 14 pages.

Naini, V. et al., (Sep. 1995). "Physical Characterization of Spray Dried Sugars Suitable as Carriers in Inhalation Systems," *Pharmaceutical Research* 12(9):S181, Abstract No. PT6180.

Neer, R. M. et al., (1987). "The Use of Parathyroid Hormone Plus 1,25-Dihydroxyvitamin D to Increase Trabecular Bone in Osteoporotic Men and Postmenopausal Women," *Osteoporosis* 53:829-835.

Nursten, H.E., (1986). "Maillard Browning Reactions In Dried Foods" in *Concentration and Drying of Foods*, McCarthy, D. ed., Elsevier Applied Science, London, pp. 53-68.

O'Connor, R. E. (1990). "Powders," in *Remington's Pharmaceutical Sciences*, $18^{th}$ edition, A. R. Gennaro, ed., Mack Publishing Co. Chapter 88, pp. 1615-1632.

Patton, J. S. et al. (1994). "Bioavailability of Pulmonary Delivered Peptides and Proteins,: α-Interferon, Calcitonins and Parathyroid Hormones," *J. Controlled Release* 28:79-85.

Patton, J. S. (Oct. 1998). "Deep-Lung Delivery of Proteins," *Modern Drug Discovery* pp. 19-28.

Patton, J. S. et al., (1992). "Routes of Delivery: Case Studies, Pulmonary Delivery of Peptides and Proteins for Systemic Action," *Adv. Drug Delivery Reviews* 8:179-196.

Patton, J. S. (1993). "Chapter 16: Alternatives to Injections: Pulmonary Delivery of Peptides and Proteins," in *Therapeutic Proteins Pharmacokinetics and Pharmacodynamics*, King, et al., (eds), pp. 329-347.

Pearlman, R. et al. (Feb. 1992). "Pharmaceutics of Protein Drugs," *J. Pharm. Pharmacol.* 44(Suppl. 1):178-185.

Pikal, M. J. et al., (1990). "Moisture Transfer from Stopper to Product and Resulting Stability Implications," *International Symposium on Biological Product Freeze-Drying and Formulation*, Bethesda, USA, in *Developments in Biological Standardization*, (International Association of Biological Standardization, J. C. May and F. Brown, Acting Ed.) 74:165-179.

Pikal, M.J., (Sep. 1990). "Freeze-Drying of Proteins. Part I: Process Design" *BioPharm* 3(8):18-20, 22-23, 26-27.

Pikal, M. J. (Sep. 1995). "Modulated DSC Studies," *Pharmaceutical Research* 12(9):S-139, Abtract No. PT 6011.

Poole, P.L. et al., (1983). "Hydration-Induced Conformational and Flexibility Changes Inlysozyme at Low Water Content," *Int. J. Biol. Macromol.* 5:308-310.

Poole, P.L. et al., (1983). "Sequential Hydration of a Dry Globular Protein," *Biopolymers* 22:255-260.

Potts, M. (1994). "Desiccation Tolerance of Prokaryotes," *Micro. Rev.* 58(4):755-805.

Reynolds, T.M., (1965). "Chemistry of Nonenzymic Browning II," *Adv. Food Res.* 14:167-283.

Roos, Y. et al. (1990). "Differential Scanning Calorimetry Study of Phase Transitions Affecting the Quality of Dehydrated Materials," *Biotechnol. Prog.* 6(2):159-163.

Roos, Y. (1993). "Melting and Glass Transitions of Low Molecular Weight Carbohydrates," *Carbohydrate Research*, 238:39-48.

Rosenfeld, M. A. et al., (Apr. 19, 1991). "Adenovirus-Mediated Transfer of a Recombinant α-1 Antitrypsin Gene to the Lung Epithelium in Vivo," *Science* 252(5004):431-434.

Roser, B. J. (1987). *Chemical Abstracts*, CAPLUS, STN, vol. 107, No. 20354, one page.

Roser, B. J. (1990). *Chemical Abstracts*, CAPLUS, STN, vol. 113, No. 29245, one page.

Roser, B. J. (1991). *Chemical Abstracts*, CAPLUS, STN, vol. 115, No. 142247, one page.

Roser, B. J. et al. (1992). *Chemical Abstracts*, CAPLUS, STN, vol. 116, No. 124367, one page.

Roser, B. J. (1992). *Chemical Abstracts*, CAPLUS, STN, vol. 116, No. 127053, one page.

Roser, B. J. (1992). CAPLUS, STN, vol. 116, No. 54989, one page.

Roth, C. et al., (Sep. 2001). "Continuous Measurement of Drying Rate of Crystalline and Amorphous Systems During Freeze-Drying Using an In Situ Microbalance Technique," *Journal of Pharmaceutical Sciences*, 90(9):1345.1355.

Rydén, L. et al., (1992). "Effect of Polymers and Microspheres on the Nasal Absorption of Insulin in Rats," *International Journal of Pharmaceutics* 83:1-10.

Sakr, F. M. (Oct. 1992). "A New Approach for Insulin Delivery Via the Pulmonary Route: Design and Pharmacokinetics in Non-Diabetic Rabbits," *International Journal of Pharmaceutics* 86:1-7.

Schneider, Z.A. et al., (1968). "Thermostability of Enzyme in the Three-Dimensional Network of Polysaccharide Chains," *Bulletin de l'Académie Polonaise des Sciences*, Varsovie, CL. II, vol. XVI, No. 4, pp. 203-204.

Schluter, K. J. et al., (1984). "Pulmonary Administration of Human Insulin in Volunteers and Type 1-Diabetics," *Abstract submitted to the Diabetes: A Journal of the American Diabetes Association*, one page.

Schulter, K. J. et al., (1984). "Pulmonary Administration of Human Insulin in Volunteers and Type-1 Diabetics," *Diabetes* 33 (Suppl.):75A, Abstract No. 298.

Smith, M. A. et al., (Jun. 1994). "Advanced Maillard Reaction End Products are Associated with Alzheimer Disease Pathology," *Proc. Natl. Acad. Sci. USA* 91(12):5710-5714.

Sperling, L. H. (1986). "Chapter 6: Glass-Rubber Transition Behavior," in *Introduction to Physical Polymer Science*, New York, John Wiley & Sons, pp. 224-300.

SpiPHarma™, Mannogem™ Mannitol, Products at http://www.spipharma.com/ProductsFolder/112MannogemManitol/112MannogemPowders.html, visited on Oct. 25, 2005, 3 pages.

Cynthia L. Stevenson, et al., (Sep. 2003). "Secondary Structure Of Cyclosporine Spray-Dried Liquid Crystal by FTIR", *Journal of Pharmaceutical Sciences* 92 (9):1832-1843.

The Condensed Chemical Dictionary, (1966). "Definition of 'Glass'," $7^{th}$ edition, (1966) revised by A. Rose, State College, Pa., Reinhold Publishing Corporation, New York, p. 448.

The New Encyclopaedia Britannica (1985). "Atmospheric Humidity and Precipitation," under "Climate and Weather," vol. 16, 15th edition, Encyclopaedia Britannica, Inc., pp. 476-479.
Takiff, H. E. et al., (Jul. 1984). "Cloning and Physical Mapping of Enteric Adenoviruses (Candidate Types 40 and 41)," *Journal of Virology* 51(1):131-136.
To, E. et al., (1978). "'Collapse', a Structural Transition in Freeze Dried Carbohydrates," *J. Fd. Technol.* 13:567-581.
Townsend, M. W. et al., (1988) "Use of Lyoprotectants in the Freeze-Drying of a Model Protein, Ribonuclease A," *Journal of Parenteral Science & Technology* 42(6):190-199.
Uedaira, H. et al., (1980). "The Effect of Sugars on the Thermal Denaturation of Lyzozyme," *The Chemical Society of Japan* 53:2451-2455.
van de Beek, M. J. et al., (1969). "Preservation of the Enzymatic Activity of Rennin During Spray Drying and During Storage and The Effect of Sugars and Certain Other Activities," *Neth. Milk Dairy J.* 23(1):46-54.
Vidgren, M. et al., (1988). "In Vitro and in Vivo Deposition of Drug Particles From Pressurized Aerosol and Dry Powder Inhaler," *Drug. Devel. Indust. Pharm.* 14(15-17):2649-2665.
Vitek, M.P., et al., (May 1994). "Advanced Glycation End Products Contribute to Amyloidosis In Alzheimer Disease," *Proc. Natl. Acad. Sci. USA* 91:4766-4770.
Welsh, D. T. et al., (1991). "The Role of Trehalose in the Osmoadaptation of *Escherichia coli* NCIB 9484: Interaction of Trehalose, $K^+$ and Glutamate During Osmoadaptation in Continuous Culture" (1991)*J. Gen. Microbiol.* 137:745-750.
White, G. W. et al., (1966). "The Glassy State in Certain Sugar-Containing Food Products," *J. Food Technol.* 1:73-82.
Wigley, F. M. et al., (1971). "Insulin Across Respiratory Mucosae by Aerosol Delivery," *Diabetes* 20(8):552-556.
Williams, M. L. et al., (Jul. 20, 1955). "The Temperature Dependence of Relaxation Mechanisms in Amorphous Polymers and Other Glass-Forming Liquids," *Journal of the American Chemical Society* 77:3701-3707.
Wolanczyk, (Jan./Feb. 1989). "Differential Scanning Calorimetry Analysis of Glass Transitions," *Cryo-Letters* 10(1):73-76.
Wyde, P. R. (Jun. 1984). "Pulmonary Deposition and Clearance of Aerosolized Interferon," *Antimicrob. Agents Chem.* 25(6):729-734.
Yamazaki, S. et al., (1989). "Highly Sensitive Enzyme Immunoassay of Human Interferon-β1." *Journal of Immunoassay* 10(1):57-73.
Yoshioka, S. et al., (1999). "The Effect of Excipients on the Molecular Mobility of Lyophilized Formulations, as Measured by Glass Transition Temperature and NMR Relaxation-Based Critical Mobility Temperature," *Pharmaceutical Research* 16(1):135-140.
Nektar Motion No. 2 filed on Nov. 15, 2004, submitted in the ongoing interference proceeding involving U.S. Patent No. 6,290,991 (Roser et al.), to which the instant application claims priority, 109 pages.
Quadrant Opposition to Nektar Substantive Motion No. 2 filed on Feb. 6, 2005, submitted in the ongoing interference proceeding involving U.S. Patent No. 6,290,991 (Roser et al.), to which the instant application claims priority, 159 pages.
Nektar Reply in Support Of its Motion No. 2 filed on Mar. 11, 2005, submitted in the ongoing interference proceeding involving U.S. Patent No. 6,290,991 (Roser et al.), to which the instant application claims priority, 20 pages.
Nektar Motion No. 3 filed on Nov. 15, 2004, submitted in the ongoing interference proceeding involving U.S. Patent No. 6,290,991 (Roser et al.), to which the instant application claims priority, 94 pages.
Quadrant Opposition to Nektar Substantive Motion No. 3 filed on Feb. 6, 2005, submitted in the ongoing interference proceeding involving U.S. Patent No. 6,290,991 (Roser et al.), to which the instant application claims priority, 158 pages.
Nektar Reply In Support Of its Motion No. 3 filed on Mar. 11, 2005, submitted in the ongoing interference proceeding involving U.S. Patent No. 6,290,991 (Roser et al.), to which the instant application claims priority, 20 pages.
Nektar Motion No. 4 filed on Nov. 15, 2004, submitted in the ongoing interference proceeding involving U.S. Patent No. 6,290,991 (Roser et al.), to which the instant application claims priority, 112 pages.
Quadrant Opposition to Nektar Substantive Motion No. 4 filed on Feb. 6, 2005, submitted in the ongoing interference proceeding involving U.S. Patent No. 6,290,991 (Roser et al.), to which the instant application claims priority, 91 pages.
Nektar Reply In Support Of its Motion No. 4 filed on Mar. 11, 2005, submitted in the ongoing interference proceeding involving U.S. Patent Bo. 6,290,991 (Roser et al.), to which the instant application claims priority, 17 pages.
Nektar Motion No. 5 filed on Nov. 15, 2004, submitted in the ongoing interference proceeding involving U.S. Patent No. 6,290,991 (Roser et al.), to which the instant application claims priority, 59 pages.
Quadrant Opposition to Nektar Substantive Motion No. 5 filed on Feb. 6, 2005, submitted in the ongoing interference proceeding involving U.S. Patent No. 6,290,991 (Roser et al.), to which the instant application claims priority, 73 pages.
Nektar Reply in Support Of its Motion No. 5 filed on Mar. 11, 2005, submitted in the ongoing interference proceeding involving U.S. Patent No. 6,290,991 (Roser et al.), to which the instant application claims priority, 14 pages.
Nektar Motion No. 6 filed on Nov. 15, 2004, submitted in the ongoing interference proceeding involving U.S. Patent No. 6,290,991 (Roser et al.), to which the instant application claims priority, 63 pages.
Quadrant Opposition to Nektar Substantive Motion No. 6 filed on Feb. 6, 2005, submitted in the ongoing interference proceeding involving U.S. Patent No. 6,290,991 (Roser et al.), to which the instant application claims priority, 103 pages.
Nektar Reply In Support Of its Motion No. 6 filed on Mar. 11, 2005, submitted in the ongoing interference proceeding involving U.S. Patent No. 6,290,991 (Roser et al.), to which the instant application claims priority, 14 pages.
Nektar Motion No. 7 filed on Nov. 15, 2004, submitted in the ongoing interference proceeding involving U.S. Patent No. 6,290,991 (Roser et al.), to which the instant application claims priority, 114 pages.
Quadrant Opposition to Nektar Substantive Motion No. 7 filed on Feb. 6, 2005, submitted in the ongoing interference proceeding involving U.S. Patent No. 6,290,991 (Roser et al.), to which the instant application claims priority, 185 pages.
Nektar Reply In Support Of its Motion No. 7 filed on Mar. 11, 2005, submitted in the ongoing interference proceeding involving U.S. Patent No. 6,290,991 (Roser et al.), to which the instant application claims priority, 20 pages.
Nektar Motion No. 8 filed on Dec. 10, 2004, submitted in the ongoing interference proceeding involving U.S. Patent No. 6,290,991 (Roser et al.), to which the instant application claims priority, 25 pages.
Quadrant Opposition to Nektar Responsive Motion No. 8 filed on Feb. 6, 2005, submitted in the ongoing interference proceeding involving U.S. Patent No. 6,290,991 (Roser et al.), to which the instant application claims priority, 41 pages.
Nektar Reply In Support Of its Motion No. 8 filed on Mar. 11, 2005, submitted in the ongoing interference proceeding involving U.S. Patent No. 6,290,991 (Roser et al.), to which the instant application claims priority, 14 pages.
Nektar Motion No. 9 filed on Dec. 10, 2004, submitted in the ongoing interference proceeding involving U.S. Patent No. 6,290,991 (Roser et al.), to which the instant application claims priority, 24 pages.
Quadrant Opposition to Nektar Responsive Motion No. 9 filed on Feb. 6, 2005, submitted in the ongoing interference proceeding involving U.S. Patent No. 6,290,991 (Roser et al.), to which the instant application claims priority, 116 pages.
Nektar Reply In Support Of its Motion No. 9 filed on Mar. 11, 2005, submitted in the ongoing interference proceeding involving U.S. Patent No. 6,290,991 (Roser et al.), to which the instant application claims priority, 27 pages.
Quadrant Motion No. 1 on Nov. 15, 2004, submitted in the ongoing interference proceeding involving U.S. Patent No. 6,290,991 (Roser et al.), to which the instant application claims priority, 28 pages.
Nektar Opposition to Quadrant Substantive Motion No. 1 filed on Feb. 4, 2005, submitted in the ongoing interference proceeding involving U.S. Patent No. 6,290,991 (Roser et al.), to which the instant application claims priority, 33 pages.
Quadrant Reply on Substantive Motion No. 1 filed on Mar. 13, 2005, submitted in the ongoing interference proceeding involving U.S. Patent No. 6,290,991 (Roser et al.), to which the instant application claims priority, 14 pages.

Quadrant Motion No. 2 filed on Nov. 15, 2004, submitted in the ongoing interference proceeding involving U.S. Patent No. 6,290,991 (Roser et al.), to which the instant application claims priority, 30 pages.
Nektar Opposition to Quadrant Substantive Motion No. 2 filed on Feb. 4, 2005, submitted in the ongoing interference proceeding involving U.S. Patent No. 6,290,991 (Roser et al.), to which the instant application claims priority, 30 pages.
Quadrant Reply on Substantive Motion No. 2 filed on Mar. 13, 2005, submitted in the ongoing interference proceeding involving U.S. Patent No. 6,290,991 (Roser et al.), to which the instant application claims priority, 15 pages.
Quadrant Motion No. 3 filed on Nov. 15, 2004, submitted in the ongoing interference proceeding involving U.S. Patent No. 6,290,991 (Roser et al.), to which the instant application claims priority, 18 pages.
Nektar Opposition to Quadrant Substantive Motion No. 3 filed on Feb. 4, 2005, submitted in the ongoing interference proceeding involving U.S. Patent No. 6,290,991 (Roser et al.), to which the instant application claims priority, 28 pages.
Quadrant Reply on Substantive Motion No. 3 filed on Mar. 13, 2005, submitted in the ongoing interference proceeding involving U.S. Patent No. 6,290,991 (Roser et al.), to which the instant application claims priority, 4 pages.
Quadrant Motion No. 4 filed on Nov. 15, 2004, submitted in the ongoing interference proceeding involving U.S. Patent No. 6,290,991 (Roser et al.), to which the instant application claims priority, 30 pages.
Nektar Opposition to Quadrant Substantive Motion No. 4 filed on Feb. 4, 2005, submitted in the ongoing interference proceeding involving U.S. Patent No. 6,290,991 (Roser et al.), to which the instant application claims priority, 29 pages.
Quadrant Reply on Substantive Motion No. 4 filed on Mar. 13, 2005, submitted in the ongoing interference proceeding involving U.S. Patent No. 6,290,991 (Roser et al.), to which the instant application claims priority, 14 pages.
Quadrant Motion No. 5 filed on Nov. 15, 2004, submitted in the ongoing interference proceeding involving U.S. Patent No. 6,290,991 (Roser et al.), to which the instant application claims priority, 53 pages.
Nektar Opposition to Quadrant Substantive Motion No. 5 filed on Feb. 4, 2005, submitted in the ongoing interference proceeding involving U.S. Patent No. 6,290,991 (Roser et al.), to which the instant application claims priority, 30 pages.
Quadrant Reply on Substantive Motion No. 5 filed on Mar. 13, 2005, submitted in the ongoing interference proceeding involving U.S. Patent No. 6,290,991 (Roser et al.), to which the instant application claims priority, 14 pages.
Quadrant Motion No. 6 filed on Nov. 15, 2004, submitted in the ongoing interference proceeding involving U.S. Patent No. 6,290,991 (Roser et al.), to which the instant application claims priority, 16 pages.
Nektar Opposition to Quadrant Substantive Motion No. 6 filed on Feb. 4, 2005, submitted in the ongoing interference proceeding involving U.S. Patent No. 6,290,991 (Roser et al.), to which the instant application claims priority, 18 pages.
Quadrant Reply on Substantive Motion No. 6 filed on Mar. 13, 2005, submitted in the ongoing interference proceeding involving U.S. Patent No. 6,290,991 (Roser et al.), to which the instant application claims priority, 9 pages.
Quadrant Motion No. 7 filed on Nov. 15, 2004, submitted in the ongoing interference proceeding involving U.S. Patent No. 6,290,991 (Roser et al.), to which the instant application claims priority, 92 pages.
Nektar Opposition to Quadrant Preliminary Motion No. 7 filed on Feb. 4, 2005, submitted in the ongoing interference proceeding involving U.S. Patent No. 6,290,991 (Roser et al.), to which the instant application claims priority, 30 pages.
Quadrant Reply on Substantive Motion No. 7 filed on Mar. 13, 2005, submitted in the ongoing interference proceeding involving U.S. Patent No. 6,290,991 (Roser et al.), to which the instant application claims priority, 13 pages.

Quadrant Motion No. 8 filed on Nov. 15, 2004, submitted in the ongoing interference proceeding involving U.S. Patent No. 6,290,991 (Roser et al.), to which the instant application claims priority, 91 pages.
Nektar Opposition to Quadrant Substantive Motion No. 8 filed on Feb. 4, 2005, submitted in the ongoing interference proceeding involving U.S. Patent No. 6,290,991 (Roser et al.), to which the instant application claims priority, 16 pages.
Quadrant Reply on Substantive Motion No. 8 filed on Mar. 13, 2005, submitted in the ongoing interference proceeding involving U.S. Patent No. 6,290,991 (Roser et al.), to which the instant application claims priority, 9 pages.
Quadrant Responsive Motion No. 1 filed on Dec. 10, 2004, submitted in the ongoing interference proceeding involving U.S. Patent No. 6,290,991 (Roser et al.), to which the instant application claims priority, 76 pages.
Nektar Opposition to Quadrant Responsive Motion No. 1 filed on Feb. 4, 2005, submitted in the ongoing interference proceeding involving U.S. Patent No. 6,290,991 (Roser et al.), to which the instant application claims priority, 35 pages.
Quadrant Reply on Responsive Motion No. 1 filed on Mar. 13, 2005, submitted in the ongoing interference proceeding involving U.S. Patent No. 6,290,991 (Roser et al.), to which the instant application claims priority, 14 pages.
Declaration of David Lechuga-Ballesteros, Ph.D. signed on Nov. 12, 2004, submitted in the ongoing interference proceeding involving U.S. Patent No. 6,290,991 (Roser et al.), to which the instant application claims priority, 16 pages. (Exh: 1015).
Declaration of Geoffrey William James Lee, Ph.D. signed on Nov. 10, 2004, submitted in the ongoing interference proceeding involving U.S. Patent No. 6,290,991 (Roser et al.), to which the instant application claims priority, 44 pages. (Exh: 2005).
Declaration of Richard Dalby, Ph.D. signed on Nov. 8, 2004, submitted in the ongoing interference proceeding involving U.S. Patent No. 6,290,991 (Roser et al.), to which the instant application claims priority, 8 pages. (Exh:2046).
Declaration of Thomas Joseph Anchordoquy, Ph.D. signed on Nov. 11, 2004, submitted in the ongoing interference proceeding involving U.S. Patent No. 6,290,991 (Roser et al.), to which the instant application claims priority, 13 pages. (Exh: 2041).
Quadrant Reply to the Notice of Opposition to European Publication No. 0773781B1, the European equivalent of U.S. Appl. No. 08/349,029 (to which the instant application claims priority), submitted Jun. 27, 2005, 27 pages.
Boehringer Ingelheim Notice of Opposition to European Publication No. 0773781B1, the European equivalent of U.S. Appl. No. 08/349,029 (to which the instant application claims priority), submitted Jul. 19, 2004, 21 pages.
Nektar Notice of Opposition to European Publication No. 0773781B1, the European equivalent of U.S. Appl. No. 08/349,029 (to which the instant application claims priority), submitted Jul. 22, 2004, 17 pages.
Office Action issued for U.S. Appl. No. 10/652,212, mailed Jul. 14, 2004, 5 pages.
Notice of Allowance, Notice of Allowability, Examiner's Amendment and Examiner-Initiated Interview Summary issued for U.S. Appl. No. 10/652,212, mailed Aug. 12, 2005, eight pages.
Office Action issued for U.S. Appl. No. 11/134,573, mailed Dec. 15, 2005, five pages.
Office Action issued for U.S. Appl. No. 11/134,573, mailed Sep. 6, 2006, 10 pages.
Office Action issued for U.S. Appl. No. 11/134,573, mailed Mar. 13, 2007, nine pages.
Interview Summary issued for U.S. Appl. No. 11/134,573, mailed May 11, 2007, two pages.
Office Action issued for U.S. Appl. No. 11/134,700, mailed Jan. 17, 2006, 6 pages.
Office Action issued for U.S. Appl. No. 11/134,700, mailed Sep. 26, 2006, 11 pages.
Interview Summary issued for U.S. Appl. No. 11/134,700, mailed Feb. 27, 2007, two pages.
Office Action issued for U.S. Appl. No. 11/134,700, mailed May 29, 2007, 8 pages.

Office Action issued for U.S. Appl. No. 10/857,100, mailed Dec. 8, 2004, 7 pages.
Office Action issued for U.S. Appl. No. 10/857,100, mailed Aug. 1, 2005, 8 pages.
Office Action issued for U.S. Appl. No. 10/857,100, mailed Apr. 11, 2006, 11 pages.
Office Action issued for U.S. Appl. No. 10/857,100, mailed Sep. 20, 2006, 6 pages.
United States Patent and Trademark Office, Board of Patent Appeals and Interferences, Patent Interference No. 105,219, *Quadrant Drug Delivery Ltd v. Nektar Therapeutics*, Paper No. 140, rendered Dec. 26, 2007, Decision —Bd.R. 125 —on Motions, 44 pages total.
United States Patent and Trademark Office, Board of Patent Appeals and Interferences, Patent Interference No. 105,219, *Quadrant Drug Delivery Ltd v. Nektar Therapeutics*, Paper No. 141, rendered Dec. 26, 2007, Order - Bd. R. 7(a), Bd. R. 128, Expunging Papers -, 2 pages total.
United States Patent and Trademark Office, Board of Patent Appeals and Interferences, Patent Interference No. 105,219, *Quadrant Drug Delivery Ltd v. Nektar Therapeutics*, Paper No. 142, rendered Dec. 26, 2007, Judgment —Bd.R. 127 —, 2 pages total.
Sukenik, C. N. (1975). "Enhancement of a Chemical Reaction Rate by Proper Orientation of Reacting Molecules in the Solid State," *J. Am. Chem. Soc.* 97:5290-5291.
Pikal, M. J. et al. (1977). "Thermal Decomposition of Amorphous Beta Lacam Antibacterials," *Journal of Pharmaceutical Science* 66:1312-1316.
Pearlman et al. "Formulation Strategies for Recombinant Proteins: Human Growth Hormone and Tissue Plasminogen Activator," in *Therapeutic Peptides and Proteins, Formulation, Delivery and Targetting*, Cold Spring Harbour, New York, pp. 23-31.
Iglesias et al. (1997). "Adsorption Isotherm of Amorphous Trehalose," *J. Sci. Food Agric.* 75:183-186.
Fukuoka, E. et al. (1991). "Glassy State of Pharmaceuticals. V. Relaxation During Cooling and Heating of Glass by Diffrnetial Scanning Calorimetry," *Chem. Pharm. Bull.* 39(8):2087-2090.
Hancock, B. C. et al. (1998). "A Pragmatic Test of Simple Calorimetric Method For Determining the Fragility of Some Amorphous Pharmaceutical Materials," *Pharm. Res.* 15(5):762-767.
Moynihan, C. T. et al. (1974). "Dependence of the Glass Transition Temperature on Heating and Cooling Rate," *J. Physical. Chem.* 78(26):2673-2677.
Onodera, et al. (1968). "Glass Transition of Dehydrated Amorphous Solid," *Bull. Chem. Soc. Japan* 41(9):2222.
William and Leopold (1979). "The Glassy State in Corn Embryos" *Plant Physiology* 89:977-981.
Fahy et al. (1984). "Vitrification as an Approach to Cryopreservation"*Cryobiology* 21:407-426.
Parks et al. (1928). "Studies on Glass. II The Transition Between the Glassy and Liquid States in the Case of Glucose," *Journal of Physical Chemistry* 1366-1379.
Schamblin and Zografi. (1998). "Enthalpy Relaxation in Binary Amorphous Mixtures Containing Sucrose," *Pharmaceutical Research* 15(12):1828-1834.
Yu, E. et al. (1995). "Structural Glass Transitions and Thermophysical Processes in Amorphous Carbohydrates and Their Supersaturated Solutions," *J. Chem. Soc. Faraday Trans.* 91(10):1511-1517.

Aldous, B. J. et al. (1995). "The Crystallisation of Hydrates From Amorphous Carbohydrates," *Cryo-Letters* 16:181-186.
To, E. et al. (1978). "Collapse, a Structural Transition in Freeze Dried Carbohydrates," *J. Fd. Technol.* 13:567-581.
Tsourouflis, S. et al. (1976). "Loss of Structure in Freeze-Dried Carbohydrates Solutions: Effect of Temperature, Moisture Content and Composition," *J. Sci. Fd. Agric.* 27:509-519.
Hanes, J. et al. (1997). "Porous Dry-Powder PLGA Microspheres Coated with Lung Surfactant for Systemic Insulin Delivery via the Lung," *Proc. Int'l Symp. Control Rel. Bioactive Matter* 24:57-58.
Health News Daily (Jan. 1995). "Pfizer and Inhale Therapeutic Systems Enter Pulmonary Insulin Collaboration for Dry Powder Aerosol Delivery," vol. 7, No. 13, pp. 4-5.
Franks, F. (Feb. 1989). "Separation, Improved Freeze-Drying, An Analysis of the Basic Scientific Principles," *Process Biochemistry* 24(1):iii-vii.
Gennaro, A. R. ed. (1990). "Chapter 89 —Oral Solid Dosage Forms," In *Remington's Pharmaceutical Science*, 18$^{th}$ edition, Mack Publishing Co, Gennaro, A. R., pp. 1646-1647.
Sciarra, J. J. et al. (1985). "Chapter 93: Aerosols," in Remingon's Pharmaceutical Science, 18$^{th}$ edition, Mack Publishing Co., Gennaro, A. R., pp. 1662-1677.
Malcolm, W. et al. (1955). "The Temperature Dependence of Relaxation Mechanisms in Amorphous Polymers and Other Glass-Forming Liquids," *Temperature Dependence of Relaxation Mechanisms* 77:3701-3707.
Masters, K. (1991). "Introduction," In *Spray Drying Handbook*, 5$^{th}$ edition, Longman Scientific & Technical and John Wiley & Sons, Inc., pp. 1-9 with Table of Contents.
Masters, K. (1991). "Part I —Basic Principles, Definitions §1 Spray Drying Fundamentals: Process Stages," In *Spray Drying Handbook*, 5$^{th}$ edition, Longman Scientific & Technical and John Wiley & Sons, Inc., pp. 32-33.
Masters, K. (1991). "Chapter 2 —Representation of Sprays," In *Spray Drying Handbook*, 5$^{th}$ edition, Longman Scientific & Technical and John Wiley & Sons, Inc., pp. 67-69.
Masters, K. (1991). "Chapter 8 —Drying of Droplets/Sprays," In *Spray Drying Handbook*, 5$^{th}$ edition, Longman Scientific & Technical and John Wiley & Sons, Inc., pp. 309-352.
Masters, K. (1991). "Chapter 16 —Applications in the Pharmaceutical —Biochemical Industry," In *Spray Drying Handbook*, 5$^{th}$ edition, Longman Scientific & Technical and John Wiley & Sons, Inc., pp. 643-662.
Non Final Office Action issued on Dec. 2, 2004, for U.S. Appl. No. 10/215,060, Paper No. 20041201, with PTO-Form 892, 10 pages total.
Final Office Action issued on Jul. 18, 2005, for U.S. Appl. No. 10/215,060, Paper No. 20050713, 9 pages total.
Non Final Office Action issued on Jul. 14, 2004, for U.S. Appl. No. 10/652,212, Paper No. 07082004, with PTO-Form 892, 6 pages total.
Non Final Office Action issued on Dec. 8, 2004, for U.S. Appl. No. 10/857,100, Paper No. 11262004, with PTO-Form 892, 8 pages total.
Non Final Office Action issued on Aug. 1, 2005, for U.S. Appl. No. 10/857,100, Paper No. 07222005, 6 pages total.
US 5,849,884, 12/1998, Woiszwillo et al. (withdrawn)

* cited by examiner

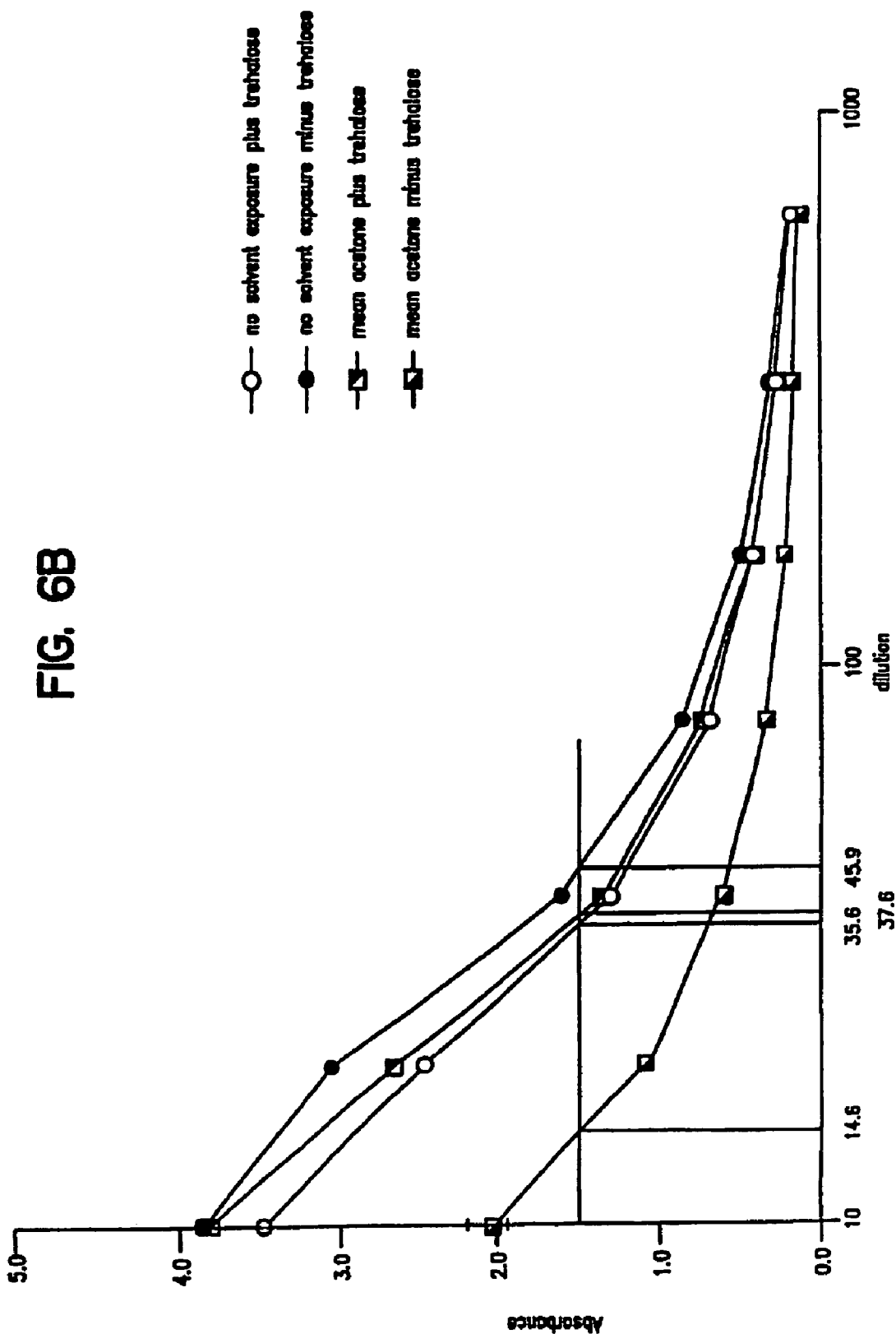

SOLID DOSE DELIVERY VEHICLE AND METHODS OF MAKING SAME

CROSS-REFERENCE TO RELATED APPLICATIONS

This application is a continuation of application Ser. No. 10/652,212, filed Aug. 29, 2003; which is a continuation of application Ser. No. 10/376,136, filed Feb. 27, 2003, now U.S. Pat. No. 6,893,657; which is a continuation of application Ser. No. 09/945,180, filed Aug. 31, 2001, now U.S. Pat. No. 6,565,871; which is a continuation of application Ser. No. 09/628,380, filed Aug. 1, 2000, now U.S. Pat. No. 6,331,310; which is a continuation of application Ser. No. 08/349,029, filed Dec. 2, 1994, now U.S. Pat. No. 6,290,991. The disclosure of each of these is incorporated by reference herein as if put forth below in full.

FIELD OF THE INVENTION

The present invention relates generally to solid dose vehicles for delivery of bioactive materials and, more specifically, to solid dose delivery vehicles comprising a stabilizing polyol and a bioactive material. Methods of their making and uses thereof are also provided.

BRIEF SUMMARY OF THE INVENTION

Solid dose delivery of bioactive materials to mucosal, dermal, ocular, subcutaneous, intradermal and pulmonary tissues offers several advantages over previous methods such as topical applications of liquids, transdermal administration via so-called "patches" and hypodermic injection. In the case of injection, solid dose delivery can reduce the risk of infection by eliminating the use of needles and syringes, provide for more accurate dosing than multidose vials, and minimize or eliminate the discomfort which often attends hypodermic injection. Several solid dose delivery systems have been developed including those utilizing transdermal and ballistic delivery devices.

Topical delivery is utilized for a variety of bioactive materials such as antibiotics for wound healing. These topical ointments, gels, creams, etc. must be frequently reapplied in order to remain effective. This is particularly difficult in the case of burn wounds.

Devices used for administering drugs transdermally usually comprise laminated composites with a reservoir layer of drug with the composite being adhered to the skin, i.e., transdermal patch, such as described in U.S. Pat. No. 4,906,463. However, many drugs are not suitable for transdermal delivery, nor have transdermal drug release rates for those capable of transdermal delivery been perfected.

Subdermal implants have also been formulated for slow release of certain pharmaceutical agents for extended periods of time such as months or years. A well-known example is the Norplant® for delivery of steroid hormones. Such implants are usually constructed of an inner, drug-filled core which is relatively permeable to the drug and an outer matrix which is relatively impermeable to the drug. Both inner core and outer matrix are generally formed from polymers. The implants release drugs by dissolution of the drug in the inner core and slow release across the outer matrix. The inner core may substantially dissolve over time, however, in devices currently in use, the outer matrix does not dissolve. Implants are placed subcutaneously by making an incision in the skin and forcing the implants between the skin and the muscle. At the end on their use, if not dissolved, these implants are surgically removed. U.S. Pat. No. 4,244,949 describes an implant which has an outer matrix of an inert plastic such as polytetrafluoroethylene resin. PCT/GB 90/00497 describes slow release vitreous systems for formation of implantable devices. These implants are bioabsorbable and need not be surgically removed. However, insertion is by surgical means. Moreover, these devices may be limited in the type of bioactive material that can be incorporated. In the case of polymeric implants, bioactive materials that cannot withstand organic solvents are not suitable for use. In the case of vitreous systems, bioactive materials that cannot withstand the elevated temperatures necessary to form the implants are unsuitable for use. In all cases, bioactive materials that are unstable at body temperature, particularly over long time periods, are unsuitable for use.

A variety of formulations have been provided for administration in aerosolized form to mucosal surfaces, particularly "by-inhalation" (naso-pharyngeal and pulmonary). Compositions for by-inhalation pharmaceutical administration generally comprise a liquid formulation of the pharmaceutical agent and a device for delivering the liquid in aerosolized form. U.S. Pat. No. 5,011,678 describes suitable compositions containing a pharmaceutically active substance, a biocompatible amphophilic steroid and a biocompatible (hydro/fluoro) carbon propellant. U.S. Pat. No. 5,006,343 describes suitable compositions containing liposomes, pharmaceutically active substances and an amount of alveolar surfactant protein effective to enhance transport of the liposomes across a pulmonary surface.

One drawback to the use of aerosolized formulations is that maintenance of pharmaceutical agents in aqueous suspensions or solutions can lead to aggregation and loss of activity and bioavailability. The loss of activity can be partially prevented by refrigeration; however, this limits the utility of these formulations. This is particularly true in the case of peptides and hormones. For instance, synthetic gonadotropin releasing hormone (GnRH) analogs, such as the agonist nafarelin or the antagonist ganirelex are designed for high potency, increased hydrophobicity and membrane binding. The compounds have sufficient hydrophobic character to aggregate in aqueous solution and to form an ordered structure that increases in viscosity with time. Thus bioavailability in nasal or pulmonary formulations may be prohibitively low. The use of powdered formulations overcomes many of these drawbacks. The requisite particle size of such powders is 0.5-5 microns in order to attain deep alveolar deposition in pulmonary delivery. Unfortunately, powders of such particle size tend to absorb water and clump and thus diminish deposition of the powder in the deep alveolar spaces. Although powders with larger particle size are suitable for delivery to the naso-pharynx region, the tendency of powders to clump decreases the available particle surface area for contact with, and absorption through, these membranes. Devices which disaggregate clumps formed by electrostatic interactions are currently in use (e.g., the Turbohaler); however, these do not disaggregate moisture induced clumps and it would be advantageous to have powders which do not absorb moisture and clump and thus increase the effective pulmonary concentration of the drug.

Solid dose delivery vehicles for ballistic, transdermal, administration have also been developed. For example, in U.S. Pat. No. 3,948,263, a ballistic animal implant comprised of an exterior polymeric shell encasing a bioactive material is described for veterinary uses. Similarly, in U.S. Pat. No. 4,326,524, a solid dose ballistic projectile comprising bioactive material and inert binder without an exterior casing is disclosed. Delivery is by compressed gas or explosion. Gelatin covered tranquilizing substances carried by ballistic projectiles for implant are also described in U.S. Pat. No. 979,993.

The above-described ballistic devices, however, are suited to large animal veterinary applications due to their relatively large size, on the order of millimeters. Ballistic delivery at the cellular level has also been successful. The general principle of ballistic administration is the use of a supersonic wavefront, created by the release of compressed gas, to propel the particles contained in an adjoining chamber. For example, nucleic acids adsorbed on tungsten microprojectile particles have been successfully delivered to living epidermal plant cells. See Klein, *Nature* 327:70-73 (1987). A better controlled device is the particle inflow gun (PIG). Vain et al. (1993) *Plant Cell, Tissue and Organ Culture* 33:237-246. Devices have been described which fire ampules containing medication using gas pressure. U.S. Pat. No. 4,790,824; and PCT/GB 94/00753. Several devices that inject fluids have also been described. U.S. Pat. Nos. 5,312,335 and 4,680,027. There are few existing formulations suitable for ballistic delivery. Powder formulations of pharmaceuticals in their present form are unsuitable for ballistic administration. Particles of available powder forms are generally irregular, varying in size, shape and density. This lack of uniformity leads to powder deposit and loss at the skin surface during administration, as well as problems in control and consistency of the depth of delivery to subcutaneous and intradermal tissues.

Thus it would be advantageous to provide solid dose drug delivery vehicles of defined size, shape and density, to ensure more uniform distribution. Additional benefits would accrue if the shape of the vehicle could be controlled to facilitate or control penetration of the epidermis and hard layers of the skin. Small delivery vehicle size, preferably coupled with high momentum delivery, would also increase the comfort of administration and minimize tissue damage. The manufacture of such a solid dose delivery vehicle should be such that neither the delivery vehicle nor the bioactive substance being delivered is damaged nor its efficacy decreased. Furthermore, the bioactive substance should remain stable when loaded within or on the vehicle so that efficacious administration can be achieved, and to facilitate storage of the loaded delivery vehicle. Manufacture of the solid dose delivery vehicle and its loading with bioactive material and the administration of the vehicle should also be relatively simple and economical.

All references cited herein are hereby incorporated by reference.

SUMMARY OF THE INVENTION

The present invention encompasses a solid dose delivery vehicle suitable for therapeutic administration of a wide variety of substances, comprising a stabilizing polyol and a bioactive material. Preferred buffers, adjuvants and additional stabilizers are also provided. The delivery vehicle can be sized and shaped for a variety of modes of administration.

The invention further includes a solid dose delivery vehicle comprising an outer portion comprising a water soluble glassy and/or polymeric material having a hollow compartment therein, and an inner portion residing in the compartment, the inner portion comprising at least one stabilizing polyol and a therapeutically effective amount of at least one bioactive substance.

The invention also encompasses methods of delivering a bioactive material by providing a solid dose delivery vehicle described above and administering the vehicle to the tissue. Administration can be by mucosal, oral, topical, subcutaneous, intradermal and by-inhalation.

The invention further encompasses methods of making the solid dose delivery vehicle. The stabilizing polyol, bioactive material and any other components are mixed and processed by a wide variety of methods, including milling, spray drying, freeze drying, air drying, vacuum drying, fluidized-bed drying, coprecipitation and critical fluid extraction. The dried components can be heated to fluidize the glass which can then be drawn or spun into solid or hollow fibers. The dried components can also be mixed in aqueous or organic solutions and dried, such as by spray drying, freeze drying, air-drying, vacuum drying, fluidized-bed drying, co-precipitation and critical fluid extraction.

The invention further provides methods of making vehicles suitable for slow or pulsatile release of bioactive substances. The methods include combining bioactive material in solid solutions in stabilizing glass-forming polyol and other glass formers with dissolution or degradation rates slower than that of the glass-forming polyol, and processing the components as described above. The ratio of materials can be controlled so as to provide a wide range of narrowly defined release rates. The coformulations of stabilizing polyol and other water-soluble and/or biodegradable glasses, plastics and glass modifiers produced thereby are also encompassed by the present invention.

The invention further provides methods of making delivery vehicles of glasses of hydrated carbohydrates hydrates with increased $T_g$ and the compositions obtained thereby. The method comprises adding a modifier, preferably a protein, in an amount sufficient to elevate the $T_g$, to the carbohydrate and processing according to a method described herein. The modifier may be an inert material or may be the bioactive material. The product obtained may be combined with stabilizing polyols with a $T_g$ less than that of the modified carbohydrate to form a slow and/or pulsatile delivery system.

The vehicles and methods of the invention also encompass vehicles which comprise fibers, spheres, particles and needles. Preferably these vehicles are fibers, spheres, particles and needles. The vehicles can be either microscopic or macroscopic.

A wide variety of bioactive materials are suitable for use in accord with the present invention, including, but not limited to, therapeutic and prophylactic agents. The delivery vehicle and methods of the present invention provide for a variety of dosing schemes for delivery of the bioactive material and are suitable for both veterinary and human applications.

BRIEF DESCRIPTION OF THE DRAWINGS

FIG. 6B is a graph depicting the resistance of alkaline phosphatase to acetone effected by drying the enzyme with trehalose.

DETAILED DESCRIPTION OF THE INVENTION

Figure 1:
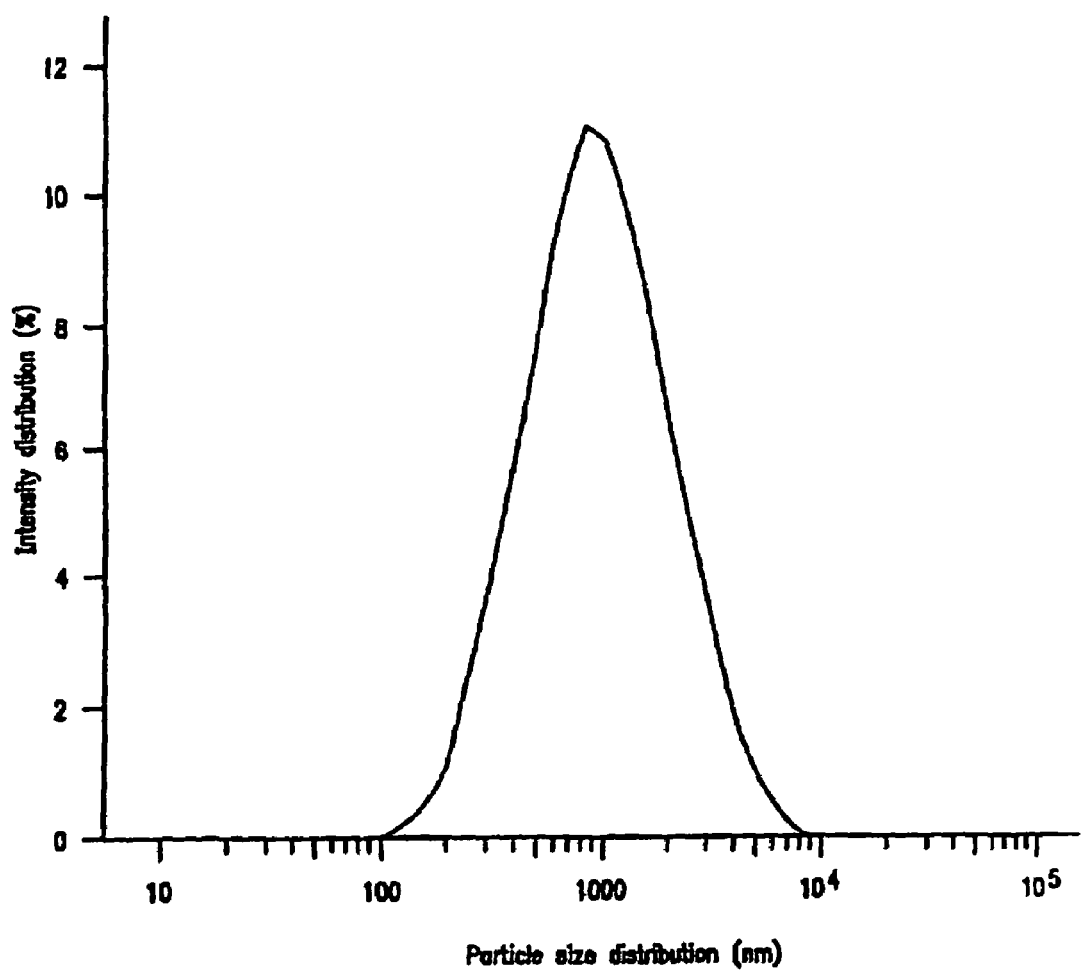
FIG. 1 is a graph depicting typical particle size distribution of micronized trehalose glass powder suitable for administration by inhalation.

The present invention comprises a solid dose delivery vehicle for mucosal, oral, topical, subcutaneous and intradermal and by-inhalation administration comprising a stabilizing polyol and a therapeutically effective amount of a bioactive material. By "solid dose" as used herein, is meant that a bioactive material delivered by the vehicle is in solid rather than liquid or aqueous form. It has now been found that stabilizing polyols can be formulated into solid vehicles suitable for drug delivery. These stabilizing polyols have been found to be particularly useful where otherwise denaturing conditions would render impossible the formulation of solid dosage forms of bioactive materials. In particular, such conditions include elevated temperatures and the presence of organic solvents.

The compositions exist as solid solutions of the bioactive material in stabilizing polyol-glass continuous phases. Previous studies have shown that in this form the product is resistant to high temperatures with the exact temperatures depending on the stabilizing polyol used. Thus, the compositions can be processed as glassy melts for brief periods without being damaged by the processing. In the same way, the stabilizing polyol containing the product would be resistant to damage during sintering with nitrate and/or carboxylate and/or derivatized carbohydrate and/or other glass-forming substances.

Examples of types of bioactive materials that may be used in the vehicle and methods of the invention include any pharmaceutical agents, including, but not limited to, antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs, opioids, and the like.

Suitable bioactive materials also include therapeutic and prophylactic agents. These include, but are not limited to, any therapeutically effective biological modifier. Such modifiers include, but are not limited to, subcellular compositions, cells, bacteria, viruses and molecules including, but not limited to, lipids, organics, proteins and peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids, small molecules and physiologically active analogs thereof. Further, the modifiers may be derived from natural sources or made by recombinant or synthetic means and include analogs, agonists and homologs. As used herein "protein" refers also to peptides and polypeptides. Such proteins include, but are not limited to, enzymes, biopharmaceuticals, growth hormones, growth factors, insulin, monoclonal antibodies, interferons, interleukins and cytokines. Organics include, but are not limited to, pharmaceutically active chemicals with amino, amino and guanidino groups. Suitable steroid hormones include, but are not limited to, estrogen, progesterone, testosterone and physiologically-active analogs thereof. Numerous steroid hormone analogs are known in the art and include, but are not limited to, estradiol, SH-135 and tamoxifen. Many steroid hormones such as progesterone, testosterone and analogs thereof are particularly suitable for use in the present invention as they are not absorbed transdermally and, with the exception of a few analogs, are destroyed upon oral administration by the so-called hepatic first pass mechanism. Therapeutic agents prepared by the methods described herein are also encompassed by the invention. As used herein, "nucleic acids" includes any therapeutically effective nucleic acids known in the art including, but not limited to DNA, RNA and physiologically active analogs thereof. The nucleotides may encode single genes or may be any vector known in the art of recombinant DNA including, but not limited to, plasmids, retroviruses and adeno-associated viruses. Preferably, the nucleotides are administered in the powder form of the solid dose vehicle.

Compositions containing prophylactic bioactive materials and carriers therefore are further encompassed by the invention. Preferable compositions include immunogens such as vaccines. Suitable vaccines include, but are not limited to, live and attenuated viruses, nucleotide vectors encoding antigens, bacteria, antigens, antigens plus adjuvants, haptens coupled to carriers. Particularly preferred are vaccines effective against diphtheria, tetanus, pertussis, botulinum, cholera, Dengue, Hepatitis A, C and E, *hemophilus influenza* b, herpes virus, Hylobacterium pylon, influenza, Japanese encephalitis, meningococci A, B and C, measles, mumps, papilloma virus, pneumococci, polio, rubella, rotavirus, respiratory syncytial virus, *Shigella*, tuberculosis, yellow fever and combinations thereof. Vaccines may also be produced by molecular biology techniques to produce recombinant peptides or fusion proteins containing one or more portions of a protein derived from a pathogen. For instance, fusion proteins containing the antigen of interest and the B subunit of cholera toxin have been shown to induce an immune response to the antigen of interest. Sanchez et al. (1989) *Proc. Natl. Acad. Sci. USA* 86:481-485.

Preferably, the immunogenic composition contains an amount of an adjuvant sufficient to enhance the immune response to the immunogen. Suitable adjuvants include, but are not limited to, aluminum salts, squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873-875. For veterinary use and for production of antibodies in animals, mitogenic components of Freund's adjuvant can be used. As with all immunogenic compositions, the immunologically effective amounts of the immunogens must be determined empirically. Factors to be considered include the immunogenicity, whether or not the immunogen will be complexed with or covalently attached to an adjuvant or carrier protein or other carrier, route of administration and the number of immunizing doses to be administered. Such factors are known in the vaccine art and it is well within the skill of immunologists to make such determinations without undue experimentation.

The present invention encompasses compositions and methods of making the compositions. Although singular forms may be used, more than one polyol, more than one biological substance and more than one inhibitor of the Maillard reaction may be present. Determination of the effective amounts of these compounds is within the skill of one in the art.

As used herein, the term "carbohydrates" includes, but is not limited to, monosaccharides, disaccharides, trisaccharides, oligosaccharides and their corresponding sugar alcohols, polyhydroxy compounds such as carbohydrate derivatives and chemically modified carbohydrates, hydroxymethyl starch and sugar copolymers (Ficoll). Both natural and synthetic carbohydrates are suitable for use herein. Synthetic carbohydrates include, but are not limited to, those which have the glycosidic bond replaced by a thiol or carbon bond. Both D and L forms of the carbohydrates may be used. The carbohydrate may be non-reducing or reducing. Suitable stabilizing polyols are those in which a bioactive material can be dried and stored without losses in activity by denaturation, aggregation or other mechanisms. Prevention of losses of activity can be enhanced by the addition of various additives such as inhibitors of the Maillard reaction as described below. Addition of such inhibitors is particularly preferred in conjunction with reducing carbohydrates.

Reducing carbohydrates suitable for use in the present invention are those known in the art and include, but are not limited to, glucose, maltose, lactose, fructose, galactose, mannose, maltulose, iso-maltulose and lactulose.

Non-reducing carbohydrates include, but are not limited to, non-reducing glycosides of polyhydroxy compounds selected from sugar alcohols and other straight chain polyalcohols. Other useful carbohydrates include raffinose, stachyose, melezitose, dextran, sucrose and sugar alcohols. The sugar alcohol glycosides are preferably monoglycosides, in particular the compounds obtained by reduction of disaccharides such as lactose, maltose, lactulose and maltulose. The glycosidic group is preferably a glucoside or a galactoside and the sugar alcohol is preferably sorbitol (glucitol). Particularly preferred carbohydrates are maltitol (4-O-β-D-glucopyranosyl-D-glucitol), lactitol (4-O-β-D-galactopyranosyl-D-glucitol), iso-maltulose, palatinit (a mixture of GPS, α-D-glucopyranosyl-1-6-sorbitol and GPM), and α-D-glucopyranosyl-1-6-mannitol, and its individual sugar alcohols, components GPS and GPM.

Preferably, the stabilizing polyol is a carbohydrate that exists as a hydrate, including trehalose, lactitol and palatinit. Most preferably, the stabilizing polyol is trehalose. It has now been found that, surprisingly, solid dose compositions containing sugar hydrates like trehalose lack the "stickiness" or "tackiness" of solid dose forms containing other carbohydrates. Thus, for manufacture, packaging and administration, trehalose is the preferred carbohydrate. Trehalose, α-D-glucopyranosyl-a-D-glucopyranoside, is a naturally occurring, non-reducing disaccharide which was initially found to be associated with the prevention of desiccation damage in certain plants and animals' which can dry out without damage and can revive when rehydrated. Trehalose has been shown to be useful in preventing denaturation of proteins, viruses and foodstuffs during desiccation. See U.S. Pat. Nos. 4,891,319; 5,149,653; 5,026,566; Blakeley et al. (1990) *Lancet* 336:854-855; Roser (July 1991) *Trends in Food Sci. and Tech.* 166-169; Colaco et al. (1992) *Biotechnol. Internat.*, 345-350; Roser (1991) *BioPharm.* 4:47-53; Colaco et al. (1992) *Bio/Tech.* 10:1007-1011; and Roser et al. (May 1993) *New Scientist*, pp. 25-28.

It has also now been found, surprisingly, that the glass transition temperature ($T_g$) of trehalose can be elevated by the addition of glass modifiers. Preferably the glass modifiers are proteins that comprise 0.002-50% of the glass modifier-trehalose mixture. Thus, the present invention encompasses the compositions and methods of making the compositions comprised of trehalose and at least one modifier, wherein the compositions have $T_g$s equal to or greater than the same composite glasses of pure trehalose. Suitable active glass modifiers include, but are not limited to, proteins and other hydrated macromolecules. Suitable proteins include any physiologically acceptable protein and may be inert or a protein to be delivered therapeutically, i.e. a bioactive material.

It has also been found that bioactive materials soluble only in organic solvents can be dried in trehalose from an organic/aqueous solvent to give a conformation that is now soluble in aqueous solvents. Methods of making the dried material and compositions obtained thereby are provided by the invention. The bioactive material is dissolved in an organic/aqueous solvent in combination with an effective amount of trehalose and then dried. This gives a solid solution of the bioactive material in a trehalose glass which then readily dissolves in an aqueous solution to give an aqueous suspension of the insoluble bioactive material. It has now been shown that the immunosuppressant cyclosporin A (which is insoluble in water and normally administered as an oil emulsion) in a solution of trehalose in a 1:1 ethanol:water mixture can be dried to give a clear glass of trehalose containing cyclosporin A. This glass can be milled to give a free flowing powder which if added to water dissolves instantaneously to give a suspension of cyclosporin A in water. If the solution dried contained a mixture of trehalose/trehalose octaacetate (insoluble in water), then the glass formed can be tailored for different dissolution rates by varying the ratio of the two.

Preferably, the compositions contain an amount of at least one physiologically acceptable salt which effects a loss of water from the composition so that at ambient humidity the vapor pressure of water of crystallization is at least 14 mm Hg (2000 Pa) at 20° C. (molecular water-pump buffer, hereinafter referred to as "MWPB") and does not interfere with glass formation of the stabilizing polyol. In the case of powders for pulmonary administration, addition of an effective amount of MWPBs is particularly preferred as they have been found to prevent wetting and clumping. An effective amount of an MWPB is one which substantially prevents wetting and clumping. Suitable salts are those described in Spanish pat. no. 2009704. These may constitute a buffer system or may replace a substantial amount of a component of the buffer in a conventional formulation. Suitable salts include, but are not limited to, ammonium chloride, orthophosphate and sulfate; barium chloride dihydrate; calcium lactate pentahydrate; copper sulfate pentahydrate; magnesium salicylate tetrahydrate, magnesium sulfate heptahydrate; potassium bisulfate, bromide, chromate and dihydrogen orthophosphate; sodium acetate trihydrate, bromoiridate dodecahydrate, carbonate decahydrate, fluoride, hydrogen orthophosphate dodecahydrate, metaperiodate trihydrate, metaphosphate trihydrate and hexahydrate, sulfite heptahydrate, sulfate heptahydrate and decahydrate and thiosulfate pentahydrate; and zinc sulfate heptahydrate and combinations thereof.

Preferably, if the bioactive material and/or glass forming polyol contain carboxyl and amino, imino or guanidino groups, the compositions further contain at least one physiologically acceptable inhibitor of the Maillard reaction in an amount effective to substantially prevent condensation of amino groups and reactive carbonyl groups in the composition.

The inhibitor of the Maillard reaction can be any known in the art. The inhibitor is present in an amount sufficient to prevent, or substantially prevent, condensation of amino groups and reactive carbonyl groups. Typically, the amino groups are present on the bioactive material and the carbonyl groups are present on the carbohydrate, or the converse. However, the amino and carbonyl groups may be intramolecular within either the biological substance or the carbohydrate. Various classes of compounds are known to exhibit an inhibiting effect on the Maillard reaction and hence to be of use in the compositions described herein. These compounds are generally either competitive or noncompetitive inhibitors. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known noncompetitive inhibitors. These include, but are not limited to, aminoguanidine and derivatives and amphotericin B.

EP-A-O 433 679 also describes suitable Maillard inhibitors which are 4-hydroxy-5,8-dioxoquinoline derivatives.

As discussed below, the composition may further contain at least one physiologically acceptable glass. Suitable glasses include, but are not limited to, carboxylate, nitrate, sulfate, bisulfate, carbohydrate derivatives and combinations thereof. Carboxylate and carbohydrate derivatives are preferred where water soluble glasses are required as many of these derivatives are slowly soluble in water. Suitable glasses include, but are not limited to, those described in PCT/GB 90/00497.

The composition may also be coated with one or more layers of a phosphate glass having a predetermined solution rate. The composition may further contain other water soluble and biodegradable glass formers. Suitable glass formers include, but are not limited to, lactide and lactide/glycolide copolymers, glucuronide polymers and other polyesters, polyorthoesters, and polyanhydrides.

In one embodiment, the delivery vehicle of the invention is sized and shaped for penetration of the epidermis and is suitable for ballistic delivery. Suitable vehicle size is thus on the order of microns, preferably in the range of 1-5 microns in diameter and 5-150 microns in length, which allows penetration and delivery through the epidermis to subcutaneous and intradermal tissues. It will be appreciated that, at this size, the delivery vehicle may macroscopically appear to be in powder form, regardless of its configuration at the microscopic level.

Preferred configurations of the delivery vehicle of the invention are microneedles and microfibers of a stabilizing polyol glass. The manufacture of microfibers is relatively simple and economical and results in stable delivery vehicles comprised of the stabilizing polyol and the bioactive material. Additional stabilizers, buffers, glasses and polymers may also be added as described herein. Many of the most labile biomolecules can withstand high temperatures (e.g., 60-100° C.) when stabilized by drying in trehalose, provided that the majority of their surface is in contact with the stabilizing polyol. Temperatures of 70° C. can be tolerated for over a month (Colaco et al. (1992) *Bio/Technology* 10:1007-1011) and higher temperatures for shorter periods. The results presented herein show that the fluorescent protein phycoerythrin dried in trehalose can be stored at 100° C. for at least one month with no detectable loss of functional activity. Other stabilizing polyols give protection at lower temperatures than trehalose. The maximum temperature of protection must be determined empirically and is within the skill of one in the art without undue experimentation.

Providing the exposure time is limited, bioactive materials admixed in dry stabilizing polyols can be heated to fluidize the glass which can then be drawn or spun as a fiber without damage to the product. Fibers can either be drawn from a billet and wound onto a drum or they can be spun through fine holes in a rapidly rotating cylinder that is heated above the melting point of the glass. Being inherently brittle, these glass fibers can be readily crushed or chopped into short lengths to form long cylindrical rods or needles. By varying the diameter of the fibers produced, needles can be formed which vary from micro to macro needles, i.e., from thicknesses of a few microns to fractions of a millimeter. It has been found that cotton candy machines are suitable for use in preparing the microfibers. Although the optimal conditions must be determined empirically for each stabilizing polyol, such determinations are well within the skill of one in the art.

The microfibers prepared in accord with the principles of the present invention, have a relatively high aspect ratio, i.e., length compared to diameter, preferably in the range of 1-5 microns in diameter and 5-150 microns in length. This high aspect ratio provides for enhanced "end on" penetration upon ballistic delivery, by the tendency of the microfibers to lineup parallel to the barrel of the ballistic microinjector, described in more detail below. Longer macrofibers may be injected using conventional impact ballistic devices or by trocar.

Alternative preferred embodiments of the delivery vehicle include uniform microspheres, preferably with a narrow size distribution. This configuration is particularly useful when increased control of the depth of penetration of the delivery vehicle is desirable. Such control would be useful, for example, for intradermal delivery of vaccines to the basal layer of the epidermis, to bring antigen into proximity to the Langerhans cells of the skin to induce optimal immune responses.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions. A number of carbohydrates are unsuitable for use in spray drying as the melting points of the carbohydrates are too low causing the dried materials to adhere to the sides of the drying chamber. Generally, carbohydrates with a melting point of less than the spray drying chamber are unsuitable for use in spray drying. For example, palatinit and lactitol are not suitable for use in spray drying under conventional conditions. A determination of suitable carbohydrates can thus be made on known melting points or determined empirically. Such determinations are within the skill of one in the art.

An alternative method for manufacturing microspheres as delivery vehicles in accord with the present invention is to prepare a uniform aqueous/organic phase emulsion of the bioactive material in a solution of the stabilizing polyol as the aqueous phase and the glass former in the organic phase. This is followed by drying of the emulsion droplets to form a solid solution of the bioactive material and stabilizing polyol in an amorphous matrix of the glass former. In a modification of this method, the emulsion may be formed from the bioactive compound in solid solution in the stabilizing polyol and two different polymers dissolved together in one solvent, or dissolved into two separate solvents. The solvent(s) are then removed by evaporation to yield double or multi-walled microspheres. Suitable methods for making multi-walled microspheres are described, for instance, in Pekarek et al. (1994) *Nature* 367:258-260; and U.S. Pat. No. 4,861,627.

The bioactive material can also be dried from an organic solution of the stabilizing polyol and the bioactive material to form a glass containing homogeneously distributed bioactive material in solid solution in the polyol glass. These glasses can then be milled and/or micronized to give microparticles of homogeneous defined sized.

The bioactive material and the stabilizing polyol can also be co-precipitated to give high quality powders. Co-precipitation is performed by spraying, for instance with an air brush, the bioactive material and stabilizing polyol and/or glass former into a liquid in which neither dissolves, such as ice-cold acetone.

The invention also encompasses hollow fibers for delivery of bioactive materials. By drawing down a heated hollow billet, fine hollow needles can be formed. These can be made to contain a finely powdered stabilized compound by introduction of the fine powder during the melting and drawing down process. The hollow fiber can also be made of thermoplastic, organic polymer and/or carbohydrate and/or derivatized carbohydrate glass which may itself be water soluble or biodegradable.

An alternative embodiment of the delivery vehicle in the invention comprises a hollow vehicle comprised of water soluble glass or plastic which is filled and optionally coated with stabilizing polyol glass and the bioactive material. Fine hollow fibers of water-soluble inorganic or organic glasses can be drawn from a hollow billet and a finely powdered stabilizing polyol-bioactive material can be incorporated into the lumen of the billet, and therefore of the fiber, during the process. Alternatively, hollow needles of these glasses may be filled by allowing capillarity to draw up suspensions of the finely powdered bioactive substance in a volatile organic solvent which is subsequently removed by evaporation leaving the needle filled with the bioactive substance. In a modification of this method, incorporation of a soluble glass former in the organic solvent phase will result in the needle being filled with the bioactive substance in solid solution in the glass former.

In another embodiment of the invention, coformulations of stabilizing polyol glass and other water soluble materials are included. For example, coformulations of stabilizing polyol glass with water-soluble glasses such as phosphate glasses (Pilkington Glass Company) or biodegradable plastics such as lactide or lactide/glycolide copolymers will yield a more slowly eroding vehicle for delayed release of the bioactive material. A finely powdered stabilizing polyol glass/bioactive material can be intimately mixed with a finely powdered carboxylate glass and co-sintered. Alternatively, if a metal carboxylate glass has a lower melting point than the stabilized bioactive polyol glass, the latter can be homogeneously embedded as a solution in a carboxylate glass by cooling the melt obtained. This can be milled to give a fine powder with solubilities intermediate between the rapid solubility of the stabilizing polyol and the slow solubility of the carboxylate glass.

Alternate coformulations include the use of a homogeneous suspension of the finely powdered bioactive material/ stabilizing polyol mixture encapsulated in a carboxylate glass by drying from an organic solution of the carboxylate to form the carboxylate glass. This can the ground to give a fine powder which would have the rapidly dissolving stabilizing polyol glass containing the encapsulated bioactive material entrapped within a slow dissolving carboxylate glass (i.e., a conventional slow-release system). Pulsatile release formats can be achieved either by repeated encapsulation cycles using glasses of different dissolution rates, or by mixing powders of a number of coformulations with the desired range of release characteristics. Note that this glass could also be drawn or spun to give microfibers or microneedles which would be slow-release implants. It will be appreciated that any stabilizing polyol formulation should be such that it is capable of releasing the bioactive material upon administration, and should not unduly effect the stability of the material being administered.

As discussed above, glasses of derivatized carbohydrates are also suitable for use herein. Suitable derivatized carbohydrates include, but are not limited to, carbohydrate esters, ethers, imides and other poorly water-soluble derivatives and polymers.

The delivery vehicle is loaded with the bioactive materials to be delivered to the tissue by drying a solution of the bioactive material containing a sufficient quantity of stabilizing polyol to form a glass on drying. This drying can be accomplished by any method known in the art, including, but not limited to, freeze drying, vacuum, spray, belt, air or fluidized-bed drying. The dried material can be milled to a fine powder before further processing the material with the polyol glass or coformulation.

Different dosing schemes can also be achieved depending on the delivery vehicle employed. A stabilizing polyol glass delivery vehicle of the invention can provide for a quick release or flooding dose of the bioactive material after administration, upon the dissolving and release of the bioactive material from the stabilizing polyol glass. Coformulations of stabilizing polyol with water soluble glasses and plastics such as phosphate, nitrate or carboxylate glasses and lactide/glycolide, glucuronide or polyhydroxybutyrate plastics and polyesters, can provide more slowly dissolving vehicles for a slower release and prolonged dosing effect. A booster effect can also be realized by utilizing a hollow water soluble vehicle filled and coated with a stabilizing polyol glass loaded with the bioactive material. The polyol glass coating loaded with the material will dissolve rapidly to give an initial dosing effect. While the hollow outer portion of the vehicle dissolves, there will be no dosing action, followed by a booster effect of the inner filling comprised of a stabilizing polyol and a bioactive material when the hollow outer portion is breached by dissolution. Such pulsatile release format is particularly useful for vaccine delivery. Should multiple effect pulsatile delivery be desirable, delivery vehicles with any combination of layers of water soluble "non-loaded" materials and stabilizing polyol glass loaded with the bioactive material can be constructed.

The delivery of more than one bioactive material can also be achieved using a delivery vehicle comprised of multiple coatings or layers of the stabilizing polyol loaded with different materials or mixtures thereof. Administration of the solid dose delivery vehicle of the present invention can be used in conjunction with other conventional therapies and coadministered with other therapeutic, prophylactic or diagnostic substances.

The invention further encompasses methods of delivery. Suitable delivery methods include, but are not limited to, topical, transdermal, transmucosal, oral, gastrointestinal, subcutaneous, ocular, and by-inhalation (naso-pharyngeal and pulmonary, including transbronchial and transalveolar). Topical administration is, for instance, by a dressing or bandage having dispersed therein the stabilizing polyol glass/bioactive material, or by direct administration into incisions or open wounds. Creams or ointments having dispersed therein slow release beads of bioactive material/stabilizing polyol are suitable for use as topical ointments or wound filling agents.

Compositions for transdermal administration are preferably powders of microneedles or microbeads. Larger, macroscopic needles and beads are also provided for subdermal implantation and extended drug delivery. The particle sizes should be small enough so that they do not cause skin damage upon administration. Preferably, the powders are microneedles of approximately 10-1,000 microns in length and 1-150 microns in diameter. The powders may be prepackaged in single-dose, sealed, sterile formats. Suitable methods of transdermal administration include, but are not limited to, ballistic, trocar and liquid jet delivery. Ballistic administration is preferred as it is relatively painless. Generally the delivery vehicle is accelerated in a shock wave of helium or another gas and fired into the epidermis. A suitable device for ballistic delivery is described in PCT/GB 94/00753. A suitable device for liquid-jet delivery is a Medi-ject device (Diabetes Care (1993) 16, 1479-1484). Such liquid-jet devices are particularly useful with the larger macroneedle delivery vehicles which may also be delivered by the use of conventional impact ballistic devices or by trocar.

Upon transdermal administration, the degree of penetration of the delivery vehicle can be controlled to a certain degree, not only by the ballistic microinjector, described below, but also the shape and size of the powder particles. For example, when a relatively uniform and lesser degree of penetration is desirable, microspheres may be more suitable for the practice of the present invention. When a greater degree of penetration is desirable, a microfiber configuration may be preferred. Because the aspect ratio (i.e., length to diameter) of the microneedles is high they have higher masses than spherical particles with a similar diameter. If they can be induced to impact with the skin "end-on," their higher mass will give them a higher momentum for the same velocity and they will thus penetrate deeper into the tissues. When randomly orientated microneedles are put into a laminar flow of gas, they will align themselves in the direction of the air flow and in the gas-propelled ballistic injector this will ensure that they impact the skin at the right angles and thus penetrate it.

The compositions suitable for transmucosal delivery include, but are not limited to, lozenges for oral delivery, pessaries, and rings and other devices for vaginal or cervical delivery.

Compositions suitable for gastrointestinal administration include, but are not limited to, pharmaceutically acceptable powders and pills for ingestion and suppositories for rectal administration.

Compositions suitable for subcutaneous administration include, but are not limited to, various implants. Preferably the implants are macroscopic spherical or cylindrical shapes for ease of insertion and may be either fast or slow release. Since the entire implant is dissolved in the body fluids, removal of the implant is not necessary. Furthermore, the implants do not contain synthetic polymers and thus are less likely to initiate a separate immune response.

Compositions suitable for ocular administration include, but are not limited to microsphere and macrosphere formulations, and saline drops.

Compositions suitable for by-inhalation administration include, but are not limited to, powders of bioactive material/stabilizing polyol. Preferably the powders are of a particle size 0.1 to 10 microns. More preferably, the particle size is 0.5 to 5 microns. Most preferably, particle size is 1 to 4 microns. In particular for pulmonary administration, the preferred particle size is 2.5-3 microns. Preferably the powders also contain an effective amount of a physiologically acceptable MWPB. An effective amount of an MWPB is one which sufficiently reduces wetting to prevent substantial clumping, for instance, a 50% molar ratio of potassium sulfate. Sodium sulfate and calcium lactate are the preferred salts with potassium sulfate being the most preferred. Atomizers and vaporizers filled with the powders are also encompassed by the invention.

There are a variety of devices suitable for use in by-inhalation delivery of powders. See, e.g., Lindberg (1993) *Summary of Lecture at Management Forum*, Dec. 6-7, 1993 "Creating the Future for Portable Inhalers." Additional devices suitable for use herein include, but are not limited to, those described in WO9413271, WO9408552, WO9309832 and U.S. Pat. No. 5,239,993.

The following examples are provided to illustrate but not limit the present invention.

EXAMPLE 1

Methods of Making Solid Dose Delivery Vehicles a) Carbohydrate Glass Microfiber Formation.

Glasses were formed by drying 20% solutions of either trehalose, lactitol, palatinit or GPS, containing MWPB and 1 mg/ml of the fluorescent algal protein phycoerythrin under vacuum (80 mtorr) for 16 hrs. The glasses were ground in a domestic coffee mill to yield a coarse powder which was used to fill the spinning head of a Kando K1 Kandy Floss cotton candy machine (GB Patent No. 00103/76). The motor was then switched on and the powdered sugar glass heated at element settings between 5 and 9. Residence time in the spinning head was 2-10 min and a continuous process was maintained by constantly topping up the head.

The fibers produced were ground in a domestic coffee grinder and the results obtained are presented in Table 1, which shows an average-of the needles produced. These data indicate that, with all three sugar glasses, reduced element settings result in the production of finer diameter microneedles. With trehalose, setting 6 gave microneedles with a mean diameter of 15 microns, and setting 9, microneedles with a mean diameter of 40 microns. With GPS, setting 9 gave microneedles with a mean diameter of 15 microns. Microneedles formed from glasses containing buffer salts remained dry at ambient temperatures and humidities. Microneedles containing phycoerythrin showed retention of biological activity as assessed by fluorescence.

TABLE 1

| Microneedle size analysis | Length (μm) | Width (μm) |
|---|---|---|
| Mean | 192.60 | 43.35 |
| Standard Error | 12.53 | 2.33 |
| Median | 167.5 | 37.5 |
| Mode | 137.5 | 47.5 |
| Standard Deviation | 123.44 | 22.91 |
| Sample Variance | 15237.75 | 524.72 |
| Kurtosis | 16.17 | 2.55 |
| Skewness | 3.35 | 1.45 |
| Range | 862.5 | 115 |

TABLE 1-continued

| Microneedle size analysis | Length (μm) | Width (μm) |
|---|---|---|
| Minimum | 67.5 | 10 |
| Maximum | 930 | 125 |
| Sum | 18682.5 | 4205 |
| Count | 97 | 97 |
| Confidence Level (95.000%) | 24.57 | 4.56 | b) Binary Carbohydrate/Organic Mixture Glass Microfiber Formation.

Glasses were formed by drying a 5:1:1 mixture of trehalose, sodium octanoate and water under vacuum (80 mTorr) for 16 hrs. The glasses were ground in a domestic coffee mill to yield a coarse powder which was used to fill the spinning head of a Kando K1 Kandy Floss machine. The motor was then switched on and the powdered binary carbohydrate/organic glass heated at element settings between 5 and 9. As with pure trehalose glasses, reduced element settings resulted in the production of finer diameter microneedles. The binary mixture glasses can be tailored to yield glasses with significantly different tensile properties compared to the corresponding pure trehalose glasses. Residence time in the spinning head was again 2-10 min and a continuous process was maintained by constantly topping up the head. The results obtained indicate that variations of the melting points and dissolution times of the glasses and the resulting physical properties of the microfibers can be achieved by varying both the carbohydrate/organic molecules and ratios used.

EXAMPLE 2

Methods of Making Solid Dose Delivery Vehicles a) Micronized Powder Preparation.

Figure 2A:
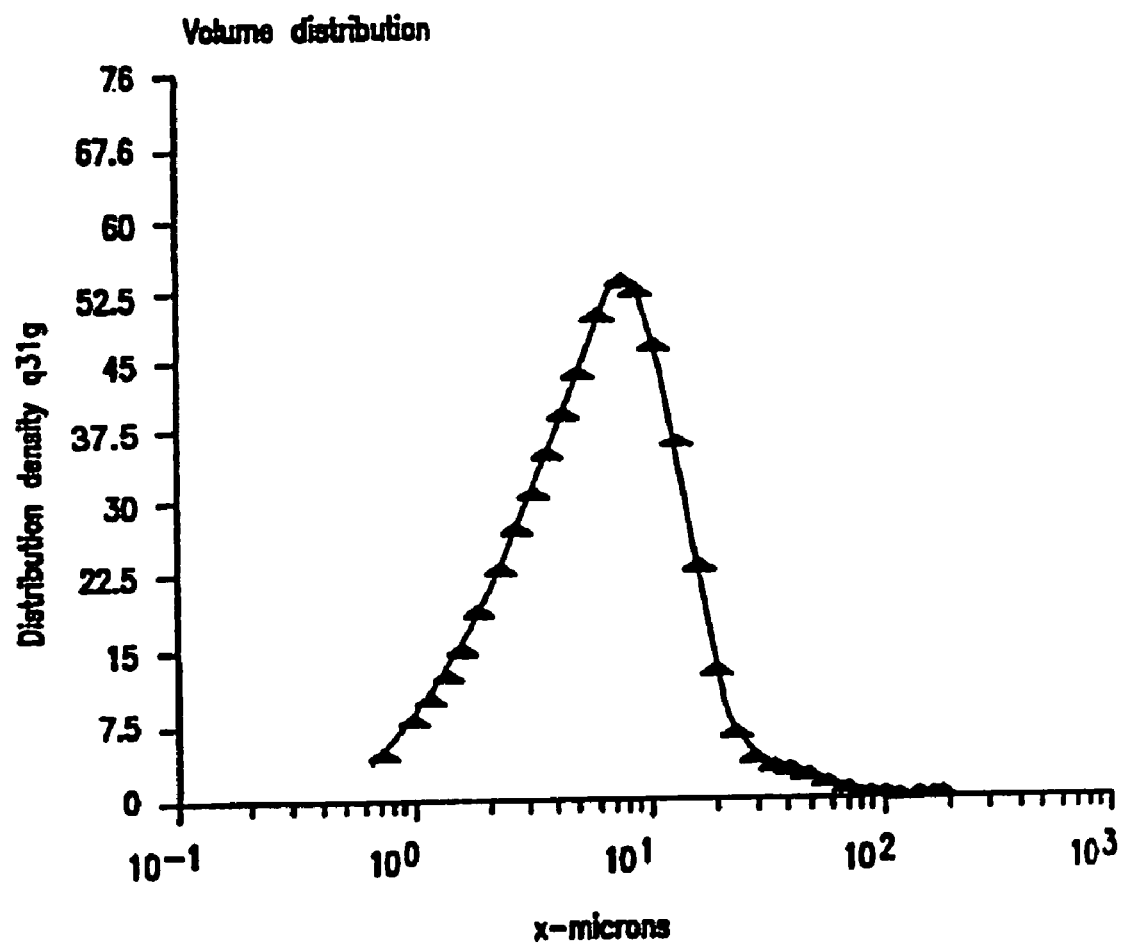
FIG. 2A is a graph depicting the sharp particle size distribution for trehalose/MWPB glass powder.
Figure 2B:
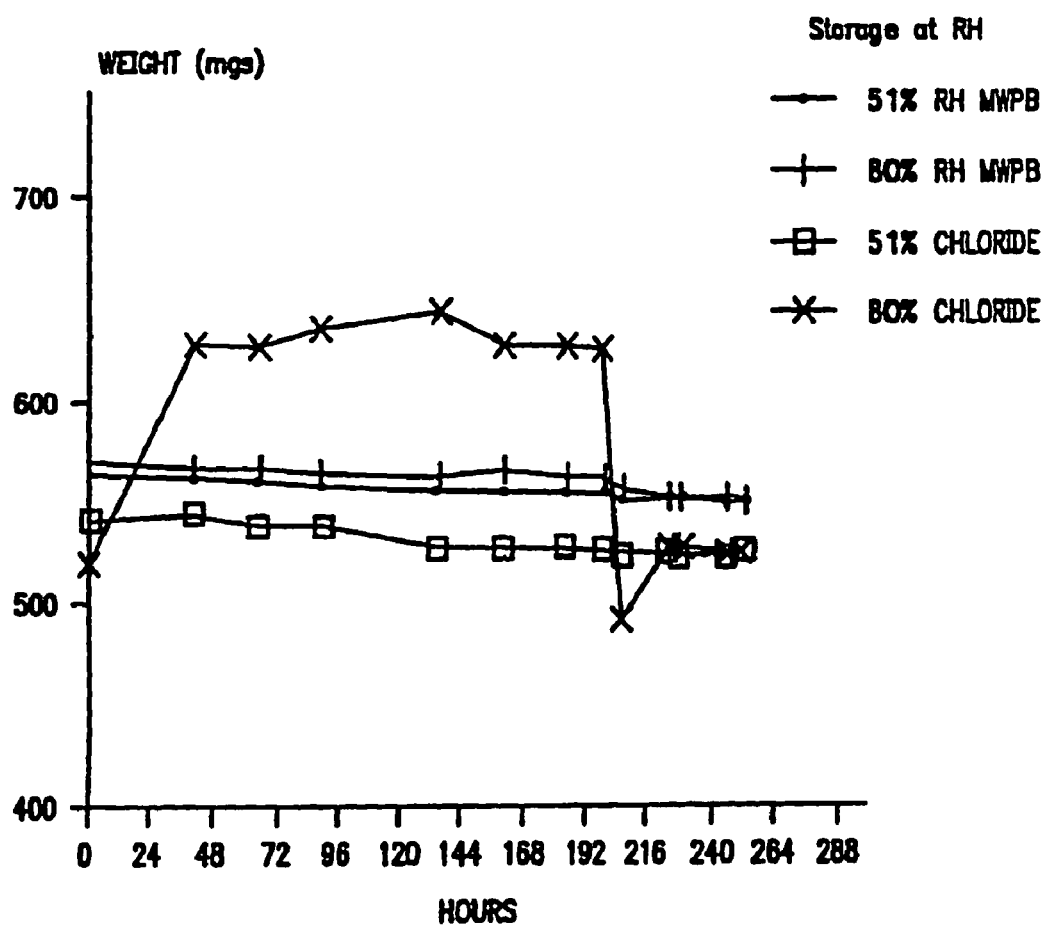
FIG. 2B is a graph depicting the wetting of various trehalose/MWPB glass powders after storage at ambient temperature and relative humidities.

Glasses were formed by drying 20% solutions of either trehalose, lactitol, palatinit, GPM or GPS, containing an equimolar ratio of MWPB and protein, by freeze-drying under vacuum (80 mTorr) for 16 hrs. The glasses were powdered using a Trost air-jet mill. Particle size in the micronized powders were measured using a Malvern Mastersizer laser particle sizer. The results obtained with micronized powders obtained from an original solution of 0.5 M trehalose and 0.5 M calcium lactate showed a monodisperse particle distribution with mean particle diameters of 1.1 microns (FIG. 1). The powders containing MWPB remained a free-flowing powder and showed no change in particle size or clumping and uptake of water on extended exposure to ambient temperatures and humidities (FIGS. 2A and 2B).

b) Spray-Dried Powder Preparation.

Figure 3:
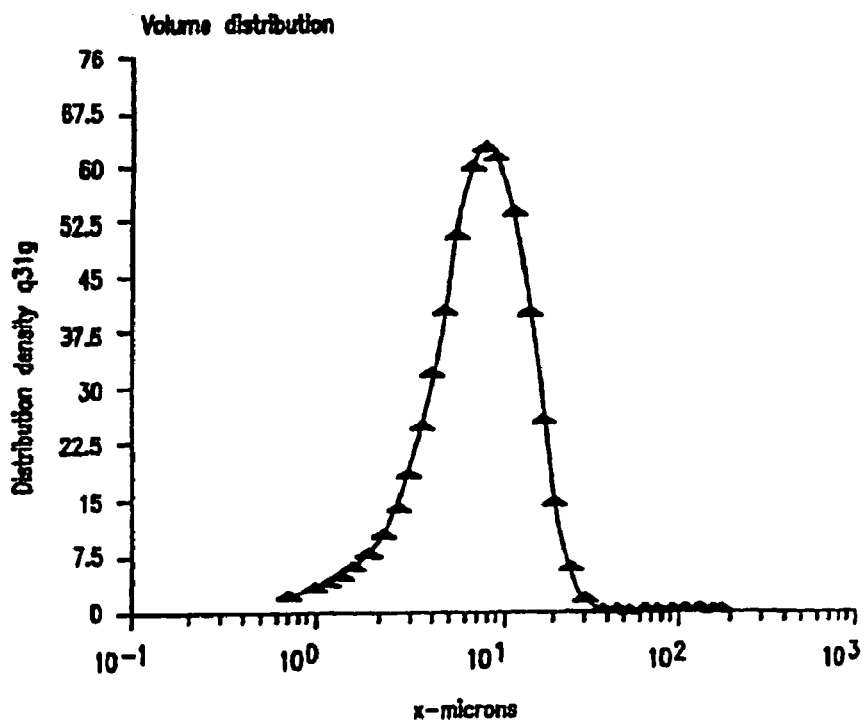
FIG. 3 is a graph depicting the sharp particle size distribution for trehalose glass powder obtained by spray-drying in a Lab-plant spray dryer.
Figure 4:
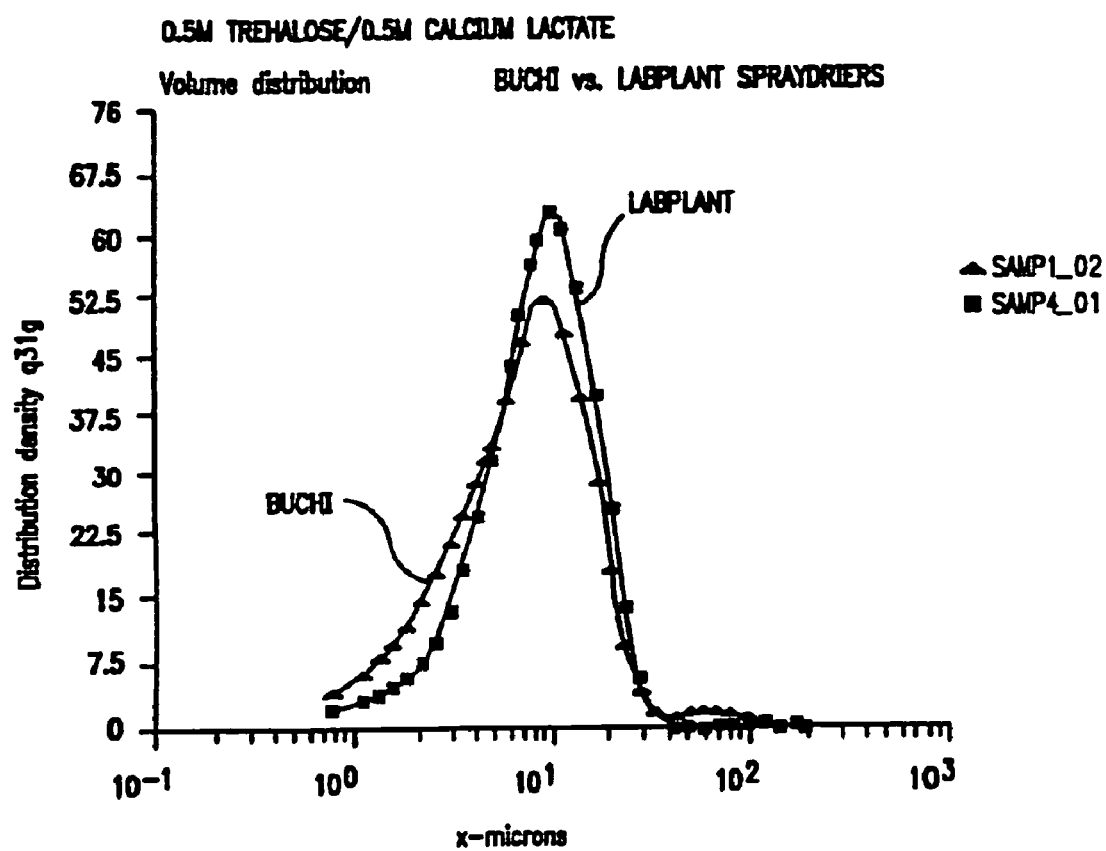
FIG. 4 is a graph depicting a comparison of the sharp particle size distribution for trehalose glass powders prepared with two different spray-dryers (Lab-plant and Buchi, as indicated).

20% solutions of trehalose containing MWPB salts and protein (phycoerythrin) were dried in a Buchi or Lab-Plant spray drier at a pump speed of 500-550 ml/hr and an inlet temperature of 180° C. Particle size was again measured using a SympaTec laser particle sizer. The spray-dried powders showed a monodisperse particle distribution with a sufficiently narrow peak size distribution for effective use as particles in a powder ballistic device. In the results shown in FIG. 3, particle size analysis of a spray-dried powder produced by spray drying a mixture of 0.5 M trehalose and 0.5 M calcium lactate on a Lab-Plant spray drier showed a mean particle diameter of 8.55 microns and illustrates the tight peak distribution obtained. Variation of the mean particle size can be achieved by varying either the composition of the mixture to be spray dried or the characteristics of the spray drier nozzle assembly used. The results shown in FIG. 4 provide a comparison of the particle-size analysis of the spray-dried powder as in FIG. 3 with a spray-dried powder produced by drying the same mixture on the Buchi spray drier which uses a different nozzle assembly. The peak distribution shown in FIG. 4 shows an equally narrow range but the mean particle size is now 7.55 microns. These data show that the particles obtained by different spray-drying processes are equally suitable to provide compositions for ballistic delivery. Note that the ability to vary particle size results in compositions with different penetrative characteristics. This is particularly important for determining intradermal or intramuscular delivery as the penetration is a function of particle momentum and the distribution is a function of the scatter of particle size.

c) Drying from Organic Solvents

A 50 mg/ml solution of cyclosporin A in a 1.1 mixture of ethanol:water, containing 20% trehalose, was air-dried at ambient temperature to form a clear trehalose glass containing cyclosporin A in solid solution. The glass was ground to give a powder, according to the method described in Example 1, and remained a free-flowing powder at ambient temperature and humidities. Addition of the powder to water resulted in the dissolution of the trehalose and the formation of a uniform aqueous suspension of cyclosporin A.

d) Co-Precipitation Powder Preparation

20% solutions of trehalose, lactitol, palatinit, GPM or GPS, containing MWPB and protein (phycoerythrin) were dried by spraying into an acetone-solid carbon dioxide freezing bath. The precipitated powders were separated by centrifugation or filtration and air dried to remove residual solvent. The powders again showed a monodisperse particle distribution and those containing buffer formulation salts remained dry at ambient temperatures and humidities.

EXAMPLE 3

Variable Solubility of Glasses of Carbohydrate/Carbohydrate Ester Coformulations Various ratios of trehalose and trehalose octaacetate (TOAC) or two different carbohydrate esters were dissolved in pyridine with sufficient water added to give a clear solution. The solutions were dried rapidly to give clear transparent monophasic glasses of the carbohydrate and/or carbohydrate ester mixes. TOAC is almost insoluble in water and increased amounts of the ester in the mixture resulted in the increased dissolution times of the coformulated glass formed.

Figure 5:
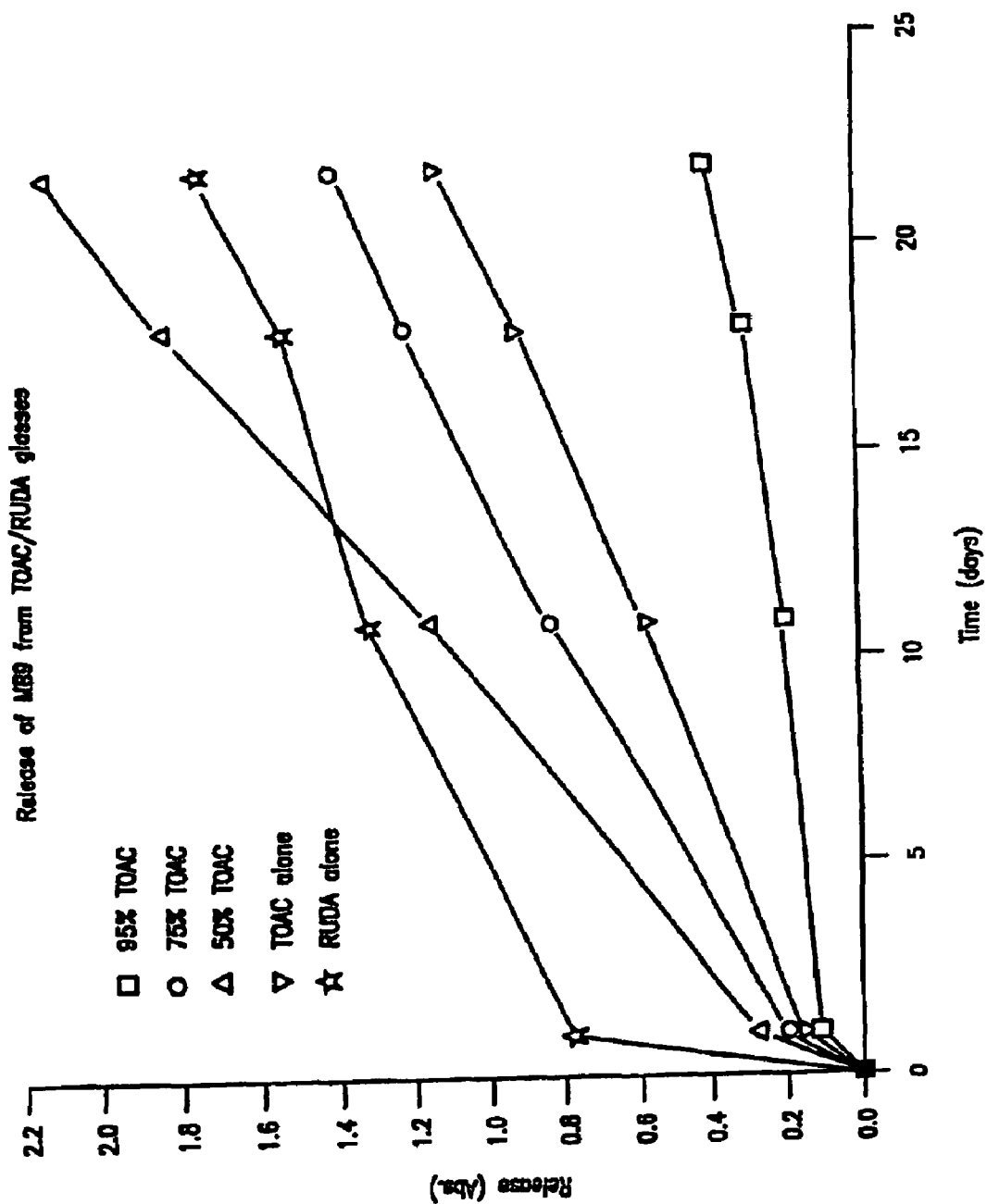
FIG. 5 is a graph depicting the release of a dye (Mordant Blue 9) from coformulated melt glasses of trehalose octaacetate (TOAC) and raffinose undecaacetate (RUDA).

Coformulations of TOAC and raffinose undecaacetate containing 1-2% Mordant Blue (MB9) dye were prepared as described above. The release rates of MB9 were measured by absorbance quantitated spectrophoto-metrically and the results are depicted in FIG. 5. These results indicate that glasses of two carbohydrate derivatives provide different release characteristics and that the use of two or more carbohydrate derivatives results in glasses tailored to provide desired release characteristics.

EXAMPLE 4

Figure 6A:
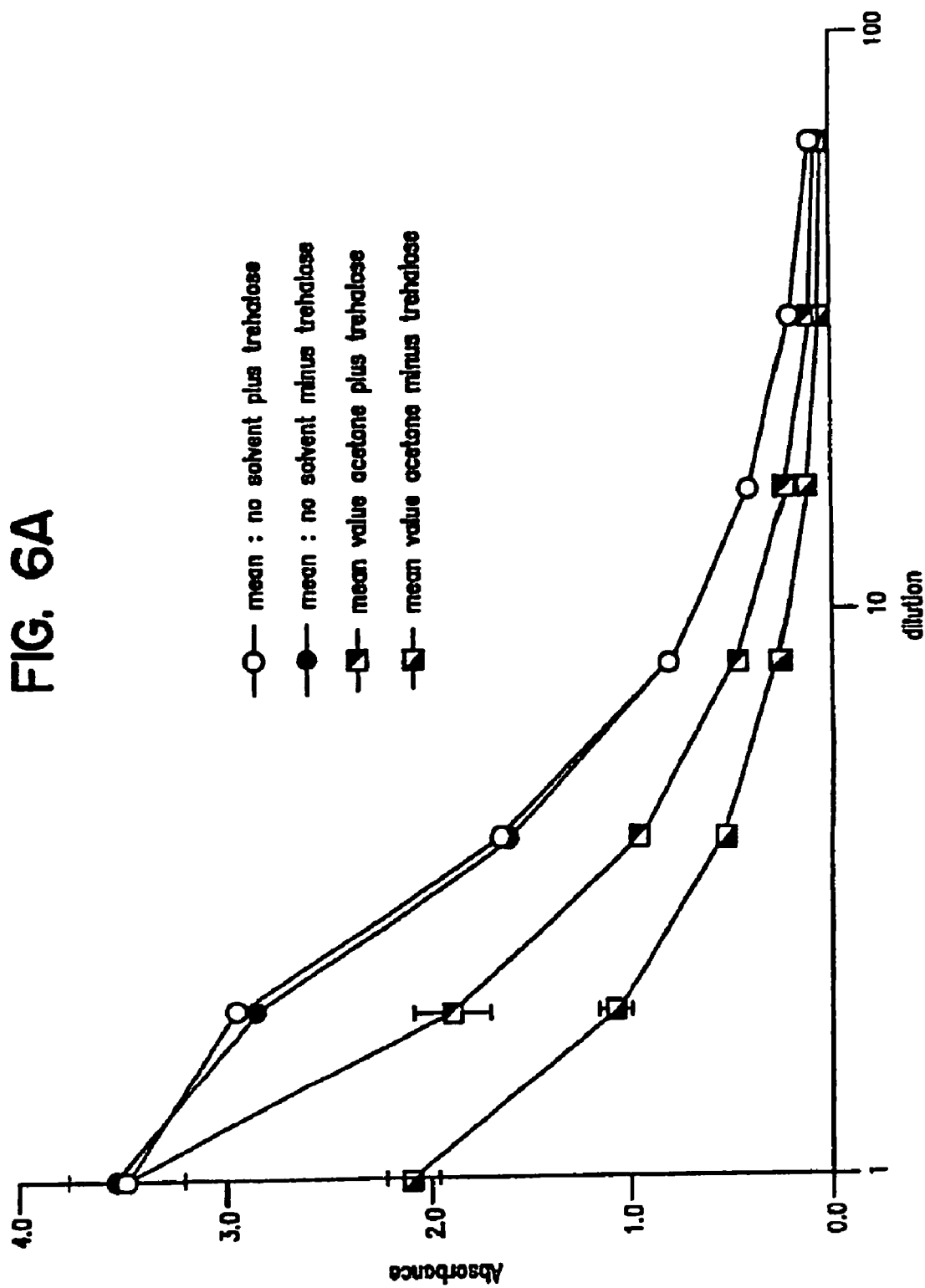
FIG. 6A is a graph depicting the resistance of horseradish peroxidase to acetone effected by drying the enzyme with trehalose.

Protection of Proteins Against an Organic Solvent and Elevated Temperatures Effected by Drying in Trehalose a) Protection of Horseradish Peroxidase and Alkaline Phosphatase Against Acetone Effected by Drying in Trehalose A 0.1 mg/ml horseradish peroxidase solution or a 1 mg/ml alkaline phosphatase/4 mg/ml bovine serum albumin Solution was dried in an FTS Systems freeze drier with or without 50% trehalose. The drier was used as a vacuum drier and the mixtures dried without freezing. Four times the volume of solvent was added and the solution was allowed to evaporate to dryness. The contents were redissolved in 5 milliliters of water, and enzyme activity was assessed, in serial dilution, by commercial 'kit' reagents. The alkaline phosphatase kit was obtained from Sigma Chemical Co. and the horseradish peroxidase kit was obtained from Kirkegaard & Perry Laboratories, Inc. As shown in FIGS. 6A and 6B, the enzymes dried with trehalose were more resistant to acetone than the enzymes dried without trehalose.

b) Protection of Phycoerythrin Against Organic Solvents Afforded by Drying In Trehalose A 400 μg/ml phycoerythrin solution was freeze-dried in a Labconco freeze-drier with or without 20% trehalose. The dried protein powder was exposed to a number of organic solvents for 72 hrs. The phycoerythrin remained fluorescent in acetone, acetonitrile chloroform and methanol. In pyridine, the phycoerythrin remained fluorescent for 24-48 hr but began wetting and lost fluorescence by 72 hrs. In dimethylsulfoxide, the powder solubilized but the phycoerythrin remained fluorescent.

c) Protection of Phycoerythrin Against 100° C. Afforded by Drying in Trehalose

A 400 μg/ml phycoerythrin solution was freeze-dried in the FTS drier with or without 20% trehalose. The dried protein was stored at 100° C. for one month with no loss of functional activity.

d) Effect of Protein on $T_g$ of Trehalose

Figure 7:
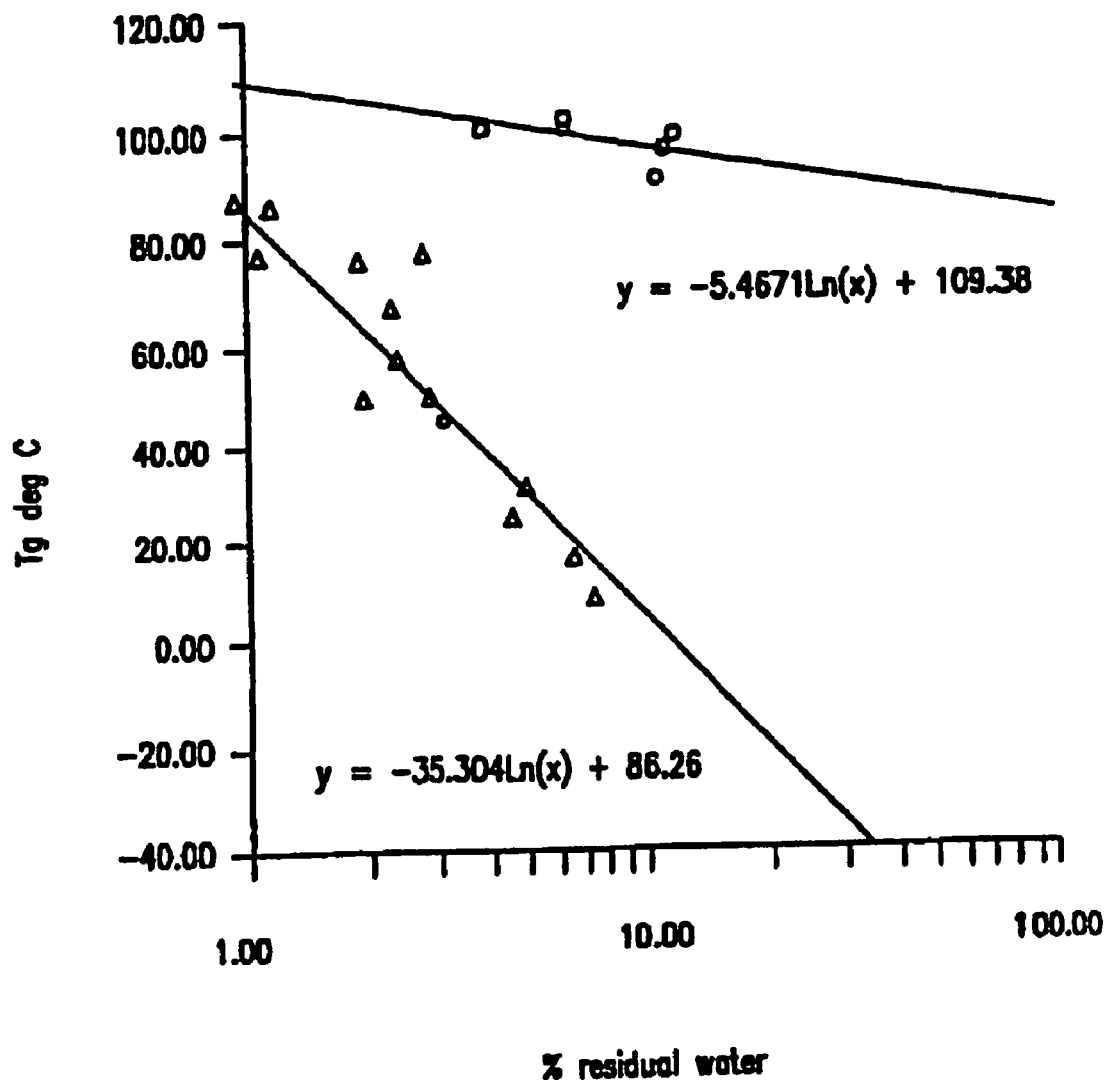
FIG. 7 is a graph depicting the effect of a glass modifier on the $T_g$ of Trehalose.
Figure 8:
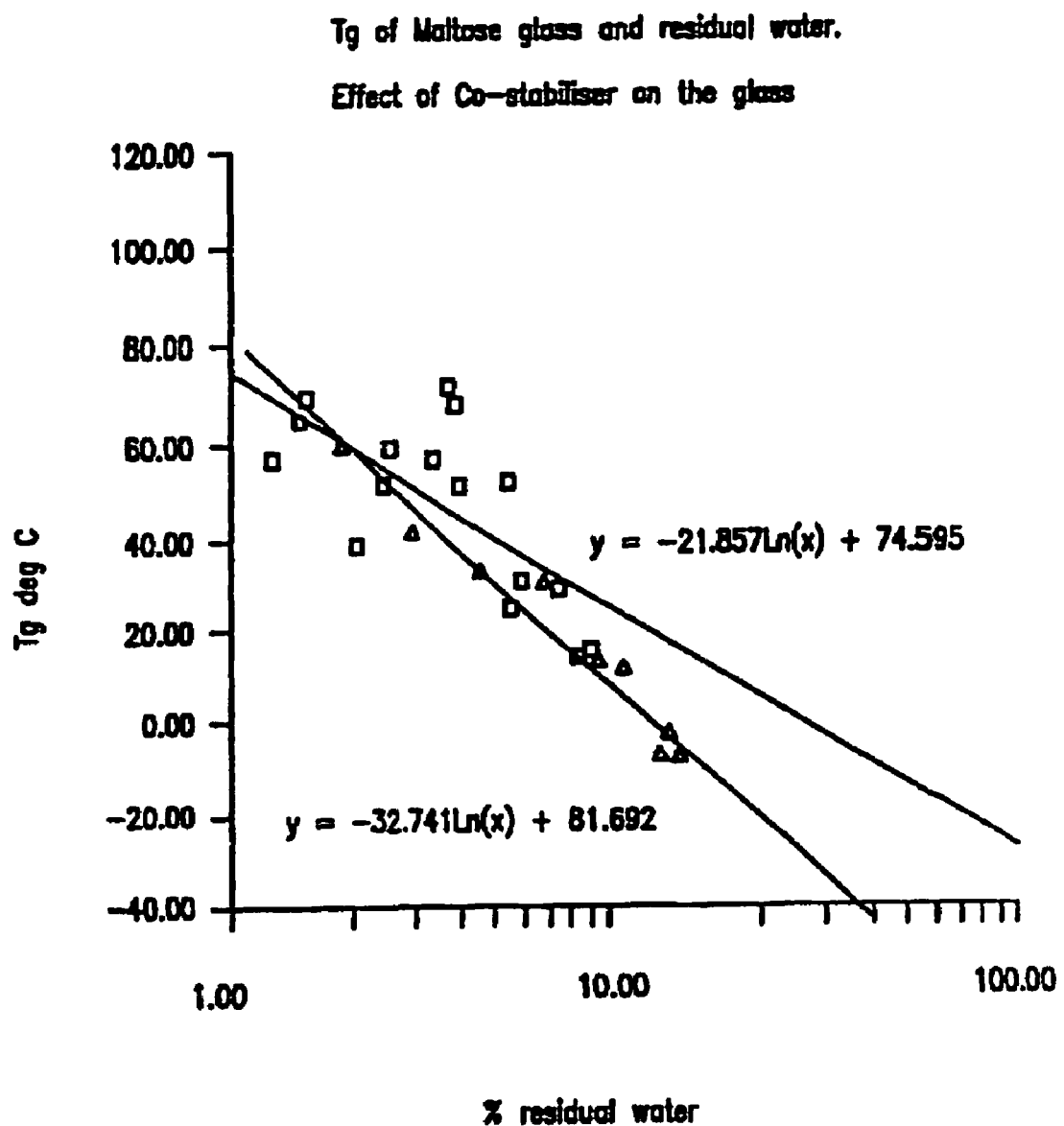
FIG. 8 is a graph depicting the effect of a glass modifier on the $T_g$ of maltose.

The presence of protein in a powdered trehalose glass has now been found to stabilize the glass against the plasticizing effected by water on pure trehalose glasses. This is illustrated by the results depicted in FIG. 7, which show the effect of water on the glass transition temperature of trehalose glasses with (solid line) or without (broken line) bovine serum albumin at concentrations of from 0.002-50%. This effect is not seen or is seen only partially with other carbohydrates, as illustrated by the results depicted in FIG. 8 utilizing maltose.

This elevation of $T_g$ by protein is utilized to formulate trehalose stabilized protein in a pure trehalose glass. A powdered protein-containing trehalose glass is prepared as described in Example 1, added to the melt of a pure trehalose glass and the mixture immediately quenched to give the trehalose-stabilized protein powder in a solid solution in a pure trehalose glass. This glass can then be further processed as described in Examples 1 and 2. A similar embedded glass can be formed if an alternative stabilizing polyol with a $T_g$ lower than that of trehalose is used to form the pure sugar glass, which again allows this glass to be melted and used below the melting point of the powdered, stabilized-protein glass to be embedded. For example, palatinit glasses melt at 60-70° C. at which temperature the protein-stabilized powder is still a glass and the trehalose-stabilized protein glass can thus be encapsulated in the palatinit glass melt by simply mixing and quenching.

EXAMPLE 5

Preparation of Bioactive Material/Stabilizing Polyol Compositions a) Microparticles of trehalose containing MB9 were prepared by spray drying as described in Example 2b. The solution dried contained 0.39 M trehalose and 0.14 M calcium lactate and 0.5% MB9. These particles were coated by adding them to a saturated solution of zinc palmitate ($ZnCl_{16}$) in toluene and cooling from 60° C. to 30° C. This deposited a layer of $ZnCl_{16}$ on the particles which were then filtered under pressure to remove the excess $ZnCl_{16}$, washed with acetone and air-dried. The resulting powder remained unwetted in water for at least three days (the particles floated in the water without sinking or releasing MB9 and thereafter slowly released dye into the water). Thus, otherwise water soluble powders may be made water impermeable by coating with metal carboxylates such as $ZnCl_{16}$ to yield slow release formats. Note that the coating material is most likely in crystalline form and not a glass; therefore, the solid phase in which the bioactive materials are suspended need not be in the glass phase to be impermeable.

b) Coformulation of Carbohydrate and Organic Glasses by Evaporation

A powdered trehalose glass containing phycoerythrin was added to a 1:1 mixture of sodium octanoate and zinc ethylhexanoate dissolved in an excess of chloroform and evaporated under a stream of $N_2$ at room temperature to yield a carboxylate glass containing phycoerythrin powder in solid solution. The coformulated glass remained insoluble in water for at least 48 hrs. The phycoerythrin powder remained fluorescent both in the initial organic solution and in the final glass.

c) Coformulation of Carbohydrate and Organic Glasses by Co-Melting

A preformed organic glass formed by quenching a melt of 1:1 mixture of sodium octanoate and zinc ethylhexanoate was melted at 95° C. and a powdered trehalose glass containing phycoerythrin was added to the melt. The resultant mixture was immediately quenched on an aluminum block precooled to 15° C. A clear carboxylate glass formed containing encapsulated phycoerythrin powder which retained its biological functionality as assayed by its ability to fluoresce. Varying the nature and ratios of the carbohydrate and organic moieties in the coformulated glasses results in glasses with a range of slow-release characteristics as assessed from their variable dissolution times in water.

d) Coformulation of Carbohydrate Glasses and Plastics by Evaporation

A powdered trehalose glass containing phycoerythrin prepared according to Example 1 was added to a solution of perspex filings dissolved in an excess of chloroform and evaporated under a stream of $N_2$ at room temperature to yield a solid perspex block containing the phycoerythrin powder in solid solution. The phycoerythrin powder remained fluorescent both in the initial organic solution and in the reformed solid perspex which was impermeable to water even after 4 weeks. Similar results were obtained with polyester dissolved in dichloromethane and polyurethane dissolved in dimethylsulfoxide.

EXAMPLE 6

Preparation of Hollow Needles Filled with Bioactive Materials

The end of a billet of a trehalose glass tubes with a central cavity filled with a powdered trehalose glass containing phycoerythrin prepared according to Example 1 was melted in a zone furnace and the fiber drawn by winding onto a metal drum rotated at constant speed. The hollow fibers formed contain the finely powdered trehalose-stabilized compound and can be cut to any desired size. The hollow fiber can also be made of thermoplastic, organic glass or carbohydrate which may itself be water soluble, and by varying the diameter of the fibers produced, the filled needles can be formed which vary from micro to macro needles, i.e. from thicknesses of microns to fractions of a millimeter. The hollow needles may be filled with any solid dose vehicle described herein.

EXAMPLE 7

Ballistic Delivery of Solid Dosage Delivery Vehicle

Powdered glasses were injected into the skin by propulsion at hypersonic speeds using a pressure shock wave created by the release of compressed gas. The powder was held in the chamber attached to the large end of a funnel-shaped cavity to the smaller end of which was attached a cartridge of compressed gas sealed by a mylar film and the hypersonic shock wave was generated by rupture of the mylar membrane. Alternatively, a timer relay-driven solenoid can be used to control the helium release which would allow functioning at lower helium pressures. This is the principle used in the particle inflow gun (PIG) developed by Finer for transforming plant tissues. Vain et al. (1993) *Plant Cell Tissue and Organ Culture* 33:237-246.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

What is claimed is:

1. A therapeutic composition in solid dose form comprising a bioactive material and a carbohydrate, wherein
   a) the bioactive material is a protein,
   b) the carbohydrate stabilizes the bioactive material in the presence of an organic solvent,
   c) the therapeutic composition comprises therapeutic particles which contain said protein homogeneously distributed in solid solution in said carbohydrate in a glassy state,
   d) the therapeutic composition is a powder having a particle size distribution suitable for pulmonary administration,
   e) the therapeutic particles containing said protein and said carbohydrate in the solid solution remain in the glassy state when stored at 60° C. for one month,
- f) the carbohydrate is selected from the group consisting of monosaccharides, disaccharides and sugar alcohols, and
- g) the therapeutic particles have a mean particle size of 0.5 to 5 μm.

2. The therapeutic composition according to claim 1, said therapeutic particles further comprising a physiologically acceptable inhibitor of the Maillard reaction.

3. The therapeutic composition according to claim 1, said therapeutic particles additionally comprising a biodegradable glass.

4. The therapeutic composition according to claim 1, wherein the particles have a mean particle size of 1 to 4 μm.

5. The therapeutic composition according to claim 1, wherein the carbohydrate is a sugar alcohol.

6. The therapeutic composition according to claim 1, wherein the carbohydrate is trehalose.

7. The therapeutic composition according to claim 1, wherein the protein is insulin.

8. The therapeutic composition according to claim 7, wherein the particles have a mean particle size of 1 to 4 μm.

9. The therapeutic composition according to claim 1, wherein the protein is insulin and the carbohydrate is trehalose.

10. The therapeutic composition according to claim 9, wherein the particles have a mean particle size of 1 to 4 μm.

11. The therapeutic composition according to claim 1, said therapeutic particles further comprising an amino acid that is capable of inhibiting the Maillard reaction.

12. The therapeutic composition according to claim 1, wherein the organic solvent is selected from the group consisting of ethanol, acetone, chloroform, acetonitrile, dichloromethane, and methanol.

13. The therapeutic composition according to claim 1, wherein the therapeutic composition is suitable for delivering the bioactive material by transalveolar administration.

14. A therapeutic composition in solid dose form comprising a bioactive material and a carbohydrate, wherein
- a) the bioactive material is a protein,
- b) the bioactive material of the therapeutic composition is stabilized in the presence of an organic solvent,
- c) the therapeutic composition comprises therapeutic particles which contain said protein homogeneously distributed in solid solution in said carbohydrate in a glassy state,
- d) the therapeutic composition is a powder having a particle size distribution suitable for pulmonary administration,
- e) the therapeutic composition further comprises a glass modifier, wherein the glass modifier is not the bioactive material,
- f) the therapeutic particles containing the protein and the carbohydrate in the solid solution remain in the glassy state when stored at 60° C. for one month,
- g) the carbohydrate is selected from the group consisting of monosaccharides, disaccharides and sugar alcohols, and
- h) the therapeutic particles have a mean particle size of 0.5 to 5 μm.

15. The therapeutic composition according to claim 14, wherein the glass modifier is a protein.

16. The therapeutic composition according to claim 14, said therapeutic particles further comprising a physiologically acceptable inhibitor of the Maillard reaction.

17. The therapeutic composition according to claim 14, said therapeutic particles additionally comprising a biodegradable glass.

18. The therapeutic composition according to claim 14, wherein the particles have a mean particle size of 1 to 4 μm.

19. The therapeutic composition according to claim 14, wherein the carbohydrate is a sugar alcohol.

20. The therapeutic composition according to claim 14, wherein the carbohydrate is trehalose.

21. The therapeutic composition according to claim 14, wherein the protein is insulin.

22. The therapeutic composition according to claim 21, wherein the particles have a mean particle size of 1 to 4 μm.

23. The therapeutic composition according to claim 14, wherein the protein is insulin and the carbohydrate is trehalose.

24. The therapeutic composition according to claim 23, wherein the particles have a mean particle size of 1 to 4 μm.

25. The therapeutic composition according to claim 14, said therapeutic particles further comprising an amino acid that is capable of inhibiting the Maillard reaction.

26. The therapeutic composition according to claim 14, wherein the organic solvent is selected from the group consisting of ethanol, acetone, chloroform, acetonitrile, dichloromethane, and methanol.

27. The therapeutic composition according to claim 14, wherein the therapeutic composition is suitable for delivering the bioactive material by transalveolar administration.

28. The therapeutic composition according to claim 1, said therapeutic particles additionally comprising a water soluble glass.

29. The therapeutic composition according to claim 28 wherein the organic solvent is dichloromethane or chloroform.

30. The therapeutic composition according to claim 7, said therapeutic particles additionally comprising a water soluble glass.

31. The therapeutic composition according to claim 1, said therapeutic particles additionally comprising a water soluble glass.

32. The therapeutic composition according to claim 31 wherein the organic solvent is dichloromethane or chloroform.

33. The therapeutic composition according to claim 1, said therapeutic particles additionally comprising a water soluble glass.

34. The therapeutic composition according to claim 1, wherein the therapeutic composition is suitable for delivering the bioactive material by transalveolar administration.

35. The therapeutic composition according to claim 34, wherein the carbohydrate is a sugar alcohol.

36. The therapeutic composition according to claim 35, said therapeutic particles further comprising an amino acid that is capable of inhibiting the Maillard reaction 37. The therapeutic composition according to claim 14, wherein the therapeutic composition is suitable for delivering the bioactive material by transalveolar administration.

38. The therapeutic composition according to claim 37, wherein the carbohydrate is a sugar alcohol.

39. The therapeutic composition according to claim 38, said therapeutic particles further comprising and amino acid that is capable of inhibiting the Maillard reaction.

\* \* \* \* \*